US008092807B2

(12) United States Patent
Jakobsen et al.

(10) Patent No.: US 8,092,807 B2
(45) Date of Patent: Jan. 10, 2012

(54) MODIFIED LEUKOCYTE IG-LIKE RECEPTOR FAMILY MEMBERS (LIRS) WITH INCREASED AFFINITY FOR CLASS 1 MHC AND THEIR USES IN MODULATING T-CELL ACTIVATION

(75) Inventors: Bent Karsten Jakobsen, Abingdon (GB); Yi Li, Abingdon (GB); Ruth Karen Moysey, Abingdon (GB)

(73) Assignee: MediGene AG, Martinsried (DE)

( * ) Notice: Subject to any disclaimer, the term of this patent is extended or adjusted under 35 U.S.C. 154(b) by 777 days.

(21) Appl. No.: 11/914,175

(22) PCT Filed: May 19, 2006

(86) PCT No.: PCT/GB2006/001860
§ 371 (c)(1),
(2), (4) Date: Jun. 12, 2008

(87) PCT Pub. No.: WO2006/125963
PCT Pub. Date: Nov. 30, 2006

(65) Prior Publication Data
US 2009/0208447 A1    Aug. 20, 2009

(30) Foreign Application Priority Data

May 25, 2005   (GB) .................................. 0510627.3

(51) Int. Cl.
*A61K 39/00*   (2006.01)
(52) U.S. Cl. ............... 424/185.1; 424/192.1; 424/193.1; 435/70.1; 435/325
(58) Field of Classification Search ........................ None
See application file for complete search history.

(56) References Cited

U.S. PATENT DOCUMENTS 6,384,203 B1 * 5/2002 Anderson et al. ............ 536/23.5

FOREIGN PATENT DOCUMENTS

| EP | 1 024 822 | 4/2002 |
|---|---|---|
| EP | 1 772 515 | 4/2007 |
| JP | 2001-507219 | 6/2001 |
| JP | 2004-524001 | 3/2005 |
| WO | WO 98/48017 | 10/1998 |
| WO | WO 9921576 | 5/1999 |
| WO | WO 99/60119 | 11/1999 |
| WO | WO 0068383 | 11/2000 |
| WO | WO 03/041650 | 5/2003 |
| WO | WO 2004/041170 | 5/2004 |
| WO | WO 2005/058953 | 6/2005 |
| WO | WO 2005/073383 | 8/2005 |
| WO | WO 2005/116646 | 12/2005 |
| WO | WO 2006/033811 | 3/2006 |
| WO | WO 2008/062147 | 5/2008 |
| WO | WO 2008062147 | 5/2008 |

OTHER PUBLICATIONS

Skolnick et al., Trends in Biotechnology, 18(1):34-39, 2000.*

Whisstock et al., Quarterly Reviews of Biophysics, 2003, 36:307-340.*
Borges et al., J. Immunol., 1997, 159:5192-5196.*
Borges et al., "A Family of Lymphoid and Myeloid Ig-Like Receptors, Some of Which Bind to MHC Class 1 Molecules," *Journal of Immunology*, vol. 159, 1997, pp. 5192-5196.
Casey et al., "Improved Tumor Targeting of di-Fab Fragments Modified with Polyethylene," *Tumor Targeting*, vol. 4, 2000, pp. 235-244.
Cella et al., "A Novel Inhibitory Receptor (ILT3) Expressed on Monocytes, Macrophages, and Dendritic Cells Involved in Antigen Processing," *J. Exp. Med.*, vol. 185, No. 10, 1997, pp. 1743-1751.
Chapman et al., "The Inhibitory Receptor LIR-1 Uses a Common Binding Interaction to Recognize Class I MHC molecules and the Viral Homolog UL18," *Immunity*, vol. 11, 1999, pp. 603-613.
Chapman et al., "Crystal Structure and Ligand Binding Properties of the D1D2 Region of the Inhibitory Receptor LIR-1 (ILT2)," *Immunity*, vol. 13, 2000, pp. 727-282.
Colonna et al., "A Common Inhibitory Receptor for Major Histocompatibility Complex Class I Human Molecules on Lymphoid and Myelmonocytic Cells," *J. Exp. Med.*, vol. 186, No. 11, 1997, pp. 1809-1818.
Colonna et al., "Human Myelmonocytic Cells Express an Inhibitory Receptor for Classical and Nonclassical MHC Class I Molecules," *Journal of Immunology*, vol. 160, 1998, pp. 3096-3100.
Cosman et al., "A Novel Immunoglobulin Superfamily Receptor for Cellular and Viral MHC Class I Molecules," *Immunity*, vol. 7, 1997, pp. 273-282.
Cosman et al., "Human Cytomegalovirus, MHC Class I and Inhibitory Signaling Receptors: More Questions than Answers," *Immunological Reviews*, vol. 168, 1999, pp. 177-185.
Garboczi et al., "HLA-A2-peptide complexes: Refolding and crystallization of molecules expressed *Escherichia coli* and complexed with single antigenic peptides," *PNAS USA*, vol. 89, 1992, pp. 3429-3433.
Kuroki et al., "Extensive polymorphisms of *LILRB* (*ILT2, LIR1*) and their association with *HLA-DRB1* shared epitope negative rheumatoid arthritis," *Human Molecular Genetics*, vol. 14, No. 16, 2005, pp. 2469-2480.
Li et al., "Directed evolution of human T-cell receptors with picomolar affinities by phage display," *Nature Biotechnology*, vol. 23, No. 3, 2005, pp. 349-354.
O'Callaghan et al., "BirA Enzyme: Production and Application in the Study of Membrane Receptor-Ligand Interactions by Site-Specific Biotinylation," *Anal. Biochem.*, vol. 266, 1999, pp. 9-15.
Pan et al., "Reduced Background Expression and Improved Plasmid Stability with pET Vectors in BL21 (DE3)," *Biotechniques*, vol. 29, vol. 6, 2000, pp. 1234-1238.

(Continued)

*Primary Examiner* — Michael Szperka
(74) *Attorney, Agent, or Firm* — Banner & Witcoff, Ltd.

(57) ABSTRACT

The present invention provides polypeptides having the property of binding to a given Class I pMHC CHARACTERISED IN THAT said polypeptide has a $K_D$ for the said given Class I pMHC of less than or equal to 1 µM and/or has an off-rate ($k_{off}$) for the said given Class I pMHC molecule of 2 $S^{-1}$ or slower AND said polypeptide has at least a 45% identity and/or 55% similarity to a defined high-affinity ILT-like molecule AND said polypeptide inhibits CD8 binding to the given pMHC to a greater extent than a soluble truncated variant of Wild-Type ILT-2. Such high-affinity ILT-like molecules are useful, either alone or associated with a therapeutic agent, for the inhibition of cytotoxic T cell (CTL) responses.

16 Claims, 33 Drawing Sheets

OTHER PUBLICATIONS

Figure 7:
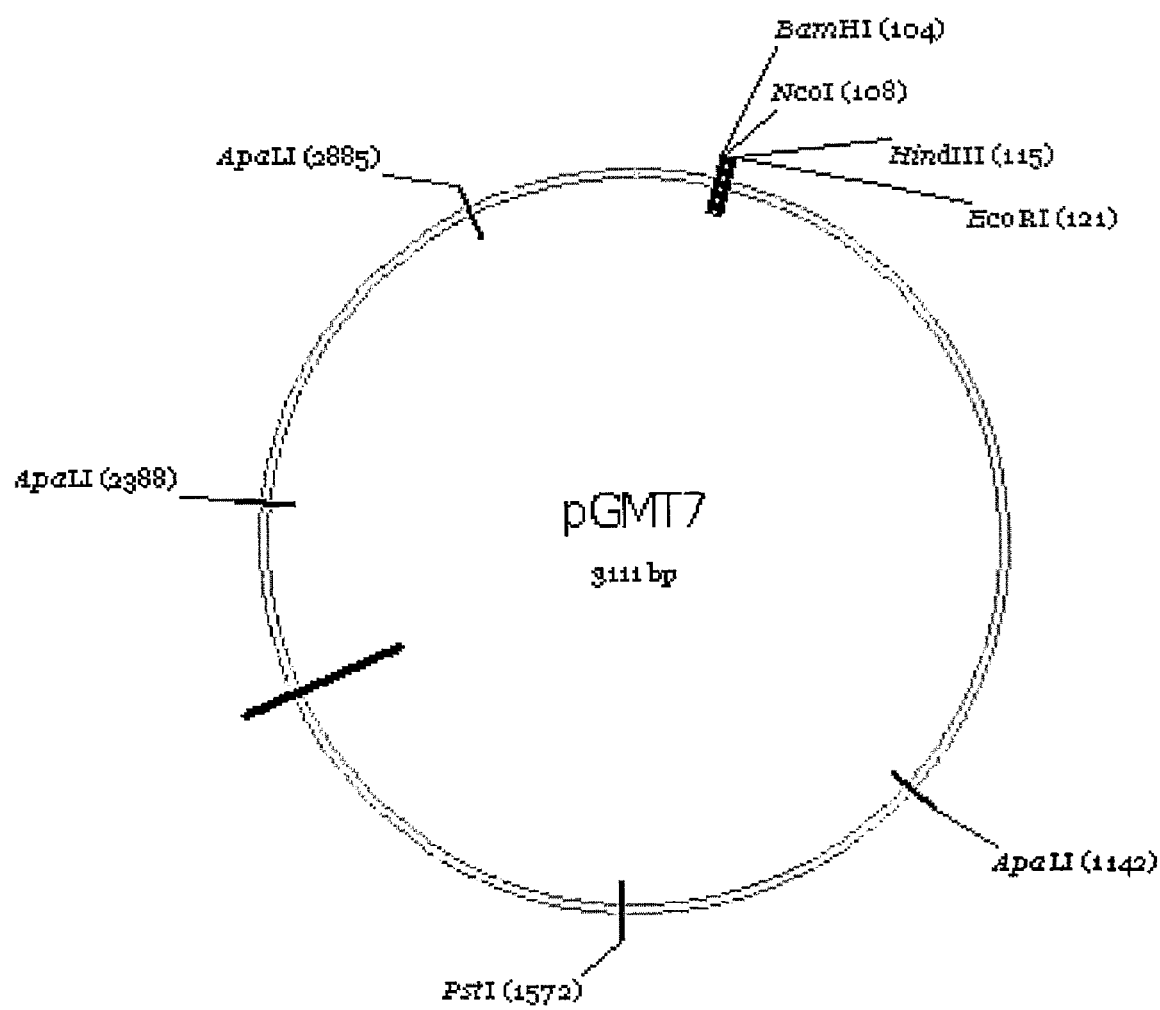

Pearson et al., "Improved tools for biological sequence comparisons," *PNAS*, vol. 85, 1988, pp. 2444-2448.

Rashtchian, "Novel methods for cloning and engineering genes using polymerase interactions," *Curr. Opin. Biotechol.*, vol. 6, No. 1, 2000, pp. 30-36.

Riteau et al., "HLA-G1 co-expression boosts the HLA class I-mediated NK lysis inhibition," *Int. Immunol.*, vol. 13, No. 2, 2001, p. 193.

Samaridis et al., "Cloning of novel immunoglobulin superfamily receptors expressed on human myeloid and lymphoid cells: structural evidence for new stimulatory and inhibitory pathways," *Eur. J. Immunol.*, vol. 27, 1997, pp. 660-665.

Schatz, "Use of Peptide Libraries to Map the Substrate Specificity of a Peptide-Modifying Enzyme: A 13 Residue Consensus Peptide Specifies Biotinylation in *Escherichia coli*," *Bio/Technology*, vol. 11, 1993, pp. 1138-1143.

Shiroishi et al., "Human inhibitory receptors lg-like transcript 2 (ILT2) and ILT4 compete with CD8 for MHC class I binding and bind preferentially to HLA-G," *PNAS*, vol. 100, No. 15, 2003, pp. 8856-8861.

Vales-Gomez et al., "Genetic Variability of the Major Histocompatibility Complex Class I Homologue Encoded by Human Cytomegalovirus Leads to Different Binding to the Inhibitory Receptor ILT2," *Journal of Virology*, vol. 79, No. 4, 2005, pp. 2251-2260.

Willcox et al., "Crystal structure of LIR-2 (ILT4) at 1.8 A: differences from LIR-1 (ILT2) in regions indicated in the binding of the Human Cytomegalovirus class I MHC homolog UL18," *BMC Structural Biology*, vol. 2, No. 6, 2002, pp. 1-9.

Willcox et al., "Crystal structure of HLA-A2 bound to LIR-1, a host and viral histocompatibility complex receptor," *Nature Immunology*, vol. 4, No. 9, 2003, pp. 913-919.

Willuda et al., "Tumor Targeting of Mono-, Di-, and Tetravalent Anti-p185$^{HER-2}$ Miniantibodies Multimerized by Self-Associating Peptides," *J. Biol. Chem.*, vol. 276, No. 17, 2001, pp. 14385-14392.

Database EMBL ebi; Oct. 3, 2003, "(Immunoglobulin-like transcript 2 (ILT-2)" XP002478010 Database accession No. Q8NHL6.

Hinton et al., "Engineered human IgG antibodies with longer serum half-lives in primates," *J. Biol. Chem.* 279(8): 6213-6216 (2004).

Hinton et al., "An Engineered Human IgG1 Antibody with Longer Serum Half-Life," *J. Immunol.* 176: 346-356 (2005).

Boulter, J. M. et al., "Potent T cell agonsim mediated by a very rapid TGR/pMHC interaction." *Eur. J. Immunol.* 37: 798-806 (2007).

Canavez, F. C. et al., "Comparison of Chimpanzee and human leukocyte Ig-like receptor genes reveals framework and rapidly evolving genes." *J. Immunol.* 167: 5786-5794 (2001).

Database UniProt [Online] Oct. 1, 2002, "Leukocyte immunoglobulin-like receptor c." XP002437420 retrieved from EBI accession No. UNIPROT:Q8MJZ4 Database accession No. Q8MJZ4.

Database UniProt [Online] Oct. 1, 2002, "Leukocyte immunoglobulin-like receptor a." XP002437424 retrieved from EBI accession No. UNIPROT:Q8MJZ6 Database accession No. Q8MJZ6 (identical to XP002437420).

Rudolph, M. G. et al., "How TCRs Bind MHCs, peptides, and coreceptors" *Ann. Rev. Immunol.* 24: 419-466 (2006).

Slukvin, I. I. et al., "Cloning of rhesus monkey LILRs." *Tissue Antigens* 67: 331-337 (2006).

Tissot et al., "Characterizing the functionality of recombinant T-cell receptors in vitro: a pMHC tetramer based approach," *J. Immunol. Methods* 236(1-2): 147-165 (2000).

Adema et al., "Isolated Mammalian Monocytic Cell Gene and Reagent Relating Thereto," Geneseq, EBI Accession No. BD509402, 2002.

Clark et al., "PRO Polypeptide SEQ ID No. 1560," Geneseq EBI Accession No. ADP24382, 2004.

Kuroki et al., "Extensive polymorphisms of *LILRB1* (*ILT2, LIR1*) and their association with *HLA-DRB1* shared epitope negative rheumatoid arthritis," Hum. Mol. Gen. 14, 2469-80, 2005.

Liu et al., "Methods and Materials Relating Leukocyte Immunoglobulin Receptor-Like (LIR-Like) Polypeptides and Polynucleotides," JPO Proteins Online EBI Accession No. BD780097, 2004.

* cited by examiner

Figure 1a

```
M T P I L T V L I C L G L S L G P R T H V Q A G H L P K P
T L W A E P G S V I T Q G S P V T L R C Q G G Q E T Q E Y
R L Y R E K K T A P W I T R I P Q E L V K K G Q F P I P S
I T W E H A G R Y R C Y Y G S D T A G R S E S S D P L E L
V V T G A Y I K P T L S A Q P S P V V N S G G N V I L Q C
D S Q V A F D G F I L C K E G E D E H P Q C L N S Q P H A
R G S S R A I F S V G P V S P S R R W W Y R C Y A Y D S N
S P Y E W S L P S D L L E L L V L G V S K K P S L S V Q P
G P I V A P E E T L T L Q C G S D A G Y N R F V L Y K D G
E R D F L Q L A G A Q P Q A G L S Q A N F T L G P V S R S
Y G G Q Y R C Y G A H N L S S E W S A P S D P L D I L I A
G Q F Y D R V S L S V Q P G P T V A S G E N V T L L C Q S
Q G W M Q T F L L T K E G A A D D P W R L R S T Y Q S Q K
Y Q A E F P M G P V T S A H A G T Y R C Y G S Q S S K P Y
L L T H P S D P L E L V V S G P S G G P S S P T T G P T S
T S G P E D Q P L T P T G S D P Q S G L G R H L G V V I G
I L V A V I L L L L L L L L F L I L R H R R Q G K H W T
S T Q R K A D F Q H P A G A V G P E P T D R G L Q W R S S
P A A D A Q E E N L Y A A V K H T Q P E D G V E M D T R S
P H D E D P Q A V T Y A E V K H S R P R R E M A S P P S P
L S G E F L D T K D R Q A E E D R Q M D T E A A A S E A P
Q D V T Y A Q L H S L T L R R K A T E P P P S Q E G P S P
A V P S I Y A T L A I H
```
(SEQ ID NO: 1)

Figure 1b

```
GAGGAGGAACAGAAAAGAAAAGAAAAGAAAAAGTGGGAAACAAATAATCTAAGAATGA
GGAGAAAGCAAGAAGAGTGACCCCCTTGTGGGCACTCCATTGGTTTTATGGCGCCTCT
ACTTTCTGGAGTTTGTGTAAAACAAAAATATTATGGTCTTTGTGCACATTTACATCAA
GCTCAGCCTGGGCGGCACAGCCAGATGCGAGATGCGTCTCTGCTGATCTGAGTCTGCC
TGCAGCATGGACCTGGGTCTTCCCTGAAGCATCTCCAGGGCTGGAGGGACGACTGCCA
TGCACCGAGGGCTCATCCATCCACAGAGCAGGGCAGTGGGAGGAGACGCCATGACCCC
CATCCTCACGGTCCTGATCTGTCTCGGGCTGAGTCTGGGCCCCGGACCCACGTGCAG
GCAGGGCACCTCCCCAAGCCCACCCTCTGGGCTGAACCAGGCTCTGTGATCACCCAGG
GGAGTCCTGTGACCCTCAGGTGTCAGGGGGCCAGGAGACCCAGGAGTACCGTCTATA
TAGAGAAAAGAAAACAGCACCCTGGATTACACGGATCCCACAGGAGCTTGTGAAGAAG
GGCCAGTTCCCCATCCCATCCATCACCTGGGAACATGCAGGGCGGTATCGCTGTTACT
ATGGTAGCGACACTGCAGGCCGCTCAGAGAGCAGTGACCCCTGGAGCTGGTGGTGAC
AGGAGCCTACATCAAACCCACCCTCTCAGCCCAGCCCAGCCCCGTGGTGAACTCAGGA
GGGAATGTAACCCTCCAGTGTGACTCACAGGTGGCATTTGATGGCTTCATTCTGTG
TAAGGAAGGAGAAGATGAACACCCACAATGCCTGAACTCCCAGCCCCATGCCCGTGGG
TCGTCCCGCGCCATCTTCTCCGTGGGCCCCGTGAGCCCGAGTCGCAGGTGGTGGTACA
GGTGCTATGCTTATGACTCGAACTCTCCCTATGAGTGGTCTCTACCCAGTGATCTCCT
GGAGCTCCTGGTCCTAGGTGTTTCTAAGAAGCCATCACTCTCAGTGCAGCCAGGTC
CTATCGTGGCCCCTGAGGAGACCCTGACTCTGCAGTGTGGCTCTGATGCTGGCTACAA
CAGATTTGTTCTGTATAAGGACGGGGAACGTGACTTCCTTCAGCTCGCTGGCGCACAG
CCCCAGGCTGGGCTCTCCCAGGCCAACTTCACCCTGGGCCCTGTGAGCCGCTCCTACG
GGGGCCAGTACAGATGCTACGGTGCACACAACCTCTCCTCCGAGTGGTCGGCCCCAG
CGACCCCCTGGACATCCTGATCGCAGGACAGTTCTATGACAGAGTCTCCCTCTCGGTG
CAGCCGGGCCCCACGGTGGCCTCAGGAGAGAACGTGACCCTGCTGTGTCAGTCACAGG
GATGGATGCAAACTTTCCTTCTGACCAAGGAGGGGGCAGCTGATGACCCATGGCGTCT
AAGATCAACGTACCAATCTCAAAATACCAGGCTGAATTCCCCATGGGTCCTGTGACC
TCAGCCCATGCGGGGACCTACAGGTGCTACGGCTCACAGAGCTCCAAACCCTACCTGC
TGACTCACCCCAGTGACCCCCTGGAGCTCGTGGTCTCAGGACCGTCTGGGGGCCCCAG
CTCCCCGACAACAGGCCCCACCTCCACATCTGGCCCTGAGGACCAGCCCCTCACCCCC
ACCGGGTCGGATCCCCAGAGTGGTCTGGGAAGGCACCTGGGGGTTGTGATCGGCATCT
TGGTGGCCGTCATCCTACTGCTCCTCCTCCTCCTCCTCTTCCTCATCCTCCGACA
TCGACGTCAGGGCAAACACTGGACATCGACCCAGAGAAAGGCTGATTTCCAACATCCT
GCAGGGGCTGTGGGCCAGAGCCCACAGACAGAGGCCTGCAGTGGAGGTCCAGCCCAG
CTGCCGATGCCCAGGAAGAAAACCTCTATGCTGCCGTGAAGCACACACAGCCTGAGGA
TGGGGTGGAGATGGACACTCGGAGCCCACACGATGAAGACCCCAGGCAGTGACGTAT
GCCGAGGTGAAACACTCCAGACCTAGGAGAGAAATGGCCTCTCCTCCTTCCCCACTGT
CTGGGGAATTCCTGGACACAAAGGACAGACAGGCGGAAGAGGACAGGCAGATGGACAC
TGAGGCTGCTGCATCTGAAGCCCCCAGGATGTGACCTACGCCCAGCTGCACAGCTTG
ACCCTTAGACGGAAGGCAACTGAGCCTCCTCCATCCCAGGAAGGGCCCTCTCCAGCTG
TGCCCAGCATCTACGCCACTCTGGCCATCCACTAGCCCAGGGGGGGACGCAGACCCCA
```

Figure 1b (Cont.)

CACTCCATGGAGTCTGGAATGCATGGGAGCTGCCCCCCCAGTGGACACCATTGGACCC
CACCCAGCCTGGATCTACCCCAGGAGACTCTGGGAACTTTTAGGGGTCACTCAATTCT
GCAGTATAAATAACTAATGTCTCTACAATTTTGAAATAAAGCAACAGACTTCTCAATA
ATCAATGAAGTAGCTGAGAAAACTAAGTCAGAAAGTGCATTAAACTGAATCACAATGT
AAATATTACACATCAAGCGATGAAACTGGAAAACTACAAGCCACGAATGAATGAATTA
GGAAAGAAAAAAGTAGGAAATGAATGATCTTGGCTTTCCTATAAGAAATTTAGGGCA
GGGCACGGTGGCTCACGCCTGTAATTCCAGCACTTTGGGAGGCCGAGGCGGGCAGATC
ACGAGTTCAGGAGATCGAGACCATCTTGGCCAACATGGTGAAACCCTGTCTCTCCTAA
AAATACAAAAATTAGCTGGATGTGGTGGCAGTGCCTGTAATCCCAGCTATTTGGGAGG
CTGAGGCAGGAGAATCGCTTGAACCAGGGAGTCAGAGGTTTCAGTGAGCCAAGATCGC
ACCACTGCTCTCCAGCCTGGCGACAGAGGGAGACTCCATCTCAAATTAAAAAAAAAA
AAAAAAGAAAGAAAAAAAAAAAAAAAAA
(SEQ ID NO: 2)

190
               *
N  S  P  Y  E  W  S  L  P  S  D  L  L  E  L  L  V  L
```
(SEQ ID NO: 3)

Figure 2b

ATGGGGCACCTCCCCAAGCCCACCCTCTGGGCTGAACCAGGCTCTGTGATCACCCAGG
GGAGTCCTGTGACCCTCAGGTGTCAGGGGGGCCAGGAGACCCAGGAGTACCGTCTATA
TAGAGAAAAGAAAACAGCACCCTGGATTACACGGATCCCACAGGAGCTTGTGAAGAAG
GGCCAGTTCCCCATCCCATCCATCACCTGGGAACATGCAGGGCGGTATCGCTGTTACT
ATGGTAGCGACACTGCAGGCCGCTCAGAGAGCAGTGACCCCCTGGAGCTGGTGGTGAC
AGGAGCCTACATCAAACCCACCCTCTCAGCCCAGCCCAGCCCCGTGGTGAACTCAGGA
GGGAATGTAACCCTCCAGTGTGACTCACAGGTGGCATTTGATGGCTTCATTCTGTGTA
AGGAAGGAGAAGATGAACACCCACAATGCCTGAACTCCCAGCCCCATGCCCGTGGGTC
GTCCCGCGCCATCTTCTCCGTGGGCCCCGTGAGCCCGAGTCGCAGGTGGTGGTACAGG
TGCTATGCTTATGACTCGAACTCTCCCTATGAGTGGTCTCTACCCAGTGATCTCCTGG
AGCTCCTGGTCCTAGCGGCCGCAGGTGGCGGTACTAGTACTGTTGAAAGTTGTTTAGC
AAAACCCCATACAGAAAATTCATTTACTAACGTCTGGAAAGACGACAAAACT
(SEQ ID NO: 4)

Figure 3

TATA<u>CATATG</u>GGTCATCTTCCAAAACCAACTCTCTGGGCTGAACCAGGCTC
TGTGATCACCCAGGGGAGTCCTGTGACCCTCAGGTGTCAGGGGGGCCAGG
AGACCCAGGAGTACCGTCTATATAGAGAAAAGAAAACAGCACCCTGGATT
ACACGGATCCCACAGGAGCTTGTGAAGAAGGGCCAGTTCCCCATCCCATC
CATCACCTGGGAACATGCAGGGCGGTATCGCTGTTACTATGGTAGCGACA
CTGCAGGCCGCTCAGAGAGCAGTGACCCCCTGGAGCTGGTGGTGACAGGA
GCCTACATCAAACCCACCCTCTCAGCCCAGCCCAGCCCCGTGGTGAACTCA
GGAGGGAATGTAACCCTCCAGTGTGACTCACAGGTGGCATTTGATGGCTTC
ATTCTGTGTAAGGAAGGAGAAGATGAACACCCACAATGCCTGAACTCCCA
GCCCCATGCCCGTGGGTCGTCCCGCGCCATCTTCTCCGTGGGCCCCGTGAG
CCCGAGCCGCAGGTGGTGGTACAGGTGCTATGCTTATGACTCGAACTCTCC
CTATGAGTGGTCTCTACCCAGTGATCTCCTGGAGCTCCTGGTCCTAT<u>AAGC
TT</u>GAATTCC
(SEQ ID NO: 5)

Figure 4a

MGHLPKPTLWAEPGSVITMGQPVTLRCQGGQETQEYRLYREKKTAPWITRIP
QELVKKGQFPIPSITWEHAGRYRCYYGSDTAGRSESSDPLELVVTGAYIKPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 6)

Figure 4b

MGHLPKPTLWAEPGSVITMDQPVTLRCQGGQETQEYRLYREKKTAPWITRIP
QELVKKGQFPIPSITWEHAGRYRCYYGSDTAGRSESSDPLELVVTGVYIKPTLS
AQPSPVVNSGGNVTLQCDSQVAFDGFILCKEGEDEHPQCLNSQPHARGSSRAI
FSVGPVSPGRRWWYRCYAYDSNSPYEWSLPSDLLELLVL
(SEQ ID NO: 7)

Figure 4c

MGHLPKPTLWAEPGSVITLMQPVTLRCQGGQETQEYRLYREKKTAPWITRIPQ
ELVKKGQFPIPSITWEHAGRYRCYYGSDTAGRSESSDPLELVVTGAYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 8)

Figure 4d

MGHLPKPTLWAEPGSVITMQRPVTLRCQGGQETQEYRLYRERKTAPWITRIPQ
ELVKKGQFPIPSITWEHAGRYRCYYGSDTAGRSESSDPLELVVTGAYIKPTLSA
QPSPVVNSGGNVTLQCDSQVAFDGFILCKEGEDEHPQCLSSQPHARGSSRAIFS
VGPVSPSRRWWYRCYAYDSNSPYEWSLPSDLLELLVL
(SEQ ID NO: 9)

Figure 5a

TATA<u>CATATG</u>GGTCATCTTCCAAAACCAACTCTCTGGGCTGAACCAGGCTC
TGTGATCACC`ATGGGGCAG`CCTGTGACCCTCAGGTGTCAGGGGGGCCAGG
AGACCCAGGAGTACCGTCTATATAGAGAAAAGAAAACAGCACCCTGGATT
ACACGGATCCCACAGGAGCTTGTGAAGAAGGGCCAGTTCCCCATCCCATC
CATCACCTGGGAACATGCAGGGCGGTATCGCTGTTACTATGGTAGCGACA
CTGCAGGCCGCTCAGAGAGCAGTGACCCCTGGAGCTGGTGGTGACAGGA
GCCTACATCAAACCCACCCTCTCAGCCCAGCCCAGCCCCGTGGTGAACTCA
GGAGGGAATGTAACCCTCCAGTGTGACTCACAGGTGGCATTTGATGGCTTC
ATTCTGTGTAAGGAAGGAGAAGATGAACACCCACAATGCCTGAACTCCCA
GCCCCATGCCCGTGGGTCGTCCCGCGCCATCTTCTCCGTGGGCCCCGTGAG
CCCGAGTCGCAGGTGGTGGTACAGGTGCTATGCTTATGACTCGAACTCTCC
CTATGAGTGGTCTCTACCCAGTGATCTCCTGGAGCTCCTGGTCCTAT<u>AAGC</u>
<u>TT</u>GAATTCC
(SEQ ID NO: 10)

Figure 5b

TATA<u>CATATG</u>GGTCATCTTCCAAAACCAACTCTCTGGGCTGAACCAGGCTC
TGTGATCACC`ATGGATCAA`CCTGTGACCCTCAGGTGTCAGGGGGGCCAGG
AGACCCAGGAGTACCGTCTATATAGAGAAAAGAAAACAGCACCCTGGATT
ACACGGATCCCACAGGAGCTTGTGAAGAAGGGCCAGTTCCCCATCCCATC
CATCACCTGGGAACATGCAGGGCGGTATCGCTGTTACTATGGTAGCGACA
CTGCAGGCCGCTCAGAGAGCAGTGACCCCTGGAGCTGGTGGTGACAGGA
`GTC`TACATCAAACCCACCCTCTCAGCCCAGCCCAGCCCCGTGGTGAACTCA
GGAGGGAATGTAACCCTCCAGTGTGACTCACAGGTGGCATTTGATGGCTTC
ATTCTGTGTAAGGAAGGAGAAGATGAACACCCACAATGCCTGAACTCCCA
GCCCCATGCCCGTGGGTCGTCCCGCGCCATCTTCTCCGTGGGCCCCGTGAG
CCC`GGGT`CGCAGGTGGTGGTACAGGTGCTATGCTTATGACTCGAACTCTCC
CTATGAGTGGTCTCTACCCAGTGATCTCCTGGAGCTCCTGGTCCTAT<u>AAGC</u>
<u>TT</u>GAATTCC
(SEQ ID NO: 11)

Figure 5c

TATA<u>CATATG</u>GGTCATCTTCCAAAACCAACTCTCTGGGCTGAACCAGGCTC
TGTGATCACC̲C̲T̲G̲A̲T̲G̲C̲A̲A̲CCTGTGACCCTCAGGTGTCAGGGGGGCCAGG
AGACCCAGGAGTACCGTCTATATAGAGAAAAGAAAACAGCACCCTGGATT
ACACGGATCCCACAGGAGCTTGTGAAGAAGGGCCAGTTCCCCATCCCATC
CATCACCTGGGAACATGCAGGGCGGTATCGCTGTTACTATGGTAGCGACA
CTGCAGGCCGCTCAGAGAGCAGTGACCCCTGGAGCTGGTGGTGACAGGA
GCCTACATCAAACCCACCCTCTCAGCCCAGCCCAGCCCCGTGGTGAACTCA
GGAGGGAATGTAACCCTCCAGTGTGACTCACAGGTGGCATTTGATGGCTTC
ATTCTGTGTAAGGAAGGAGAAGATGAACACCCACAATGCCTGAACTCCCA
GCCCCATGCCCGTGGGTCGTCCCGCGCCATCTTCTCCGTGGGCCCCGTGAG
CCCGAGCCGCAGGTGGTGGTACAGGTGCTATGCTTATGACTCGAACTCTCC
CTATGAGTGGTCTCTACCCAGTGATCTCCTGGAGCTCCTGGTCCTAT<u>AAGC
TT</u>GAATTCC
(SEQ ID NO: 12)

Figure 5d

TATA<u>CATATG</u>GGTCATCTTCCAAAACCAACTCTCTGGGCTGAACCAGGCTC
TGTGATCACC̲A̲T̲G̲C̲A̲G̲C̲G̲G̲CCTGTGACCCTCAGGTGTCAGGGGGGCCAGG
AGACCCAGGAGTACCGTCTATATAGAGAA̲A̲G̲G̲AAAACAGCACCCTGGATT
ACACGGATCCCACAGGAGCTTGTGAAGAAGGGCCAGTTCCCCATCCCATC
CATCACCTGGGAACATGCAGGGCGGTATCGCTGTTACTATGGTAGCGACA
CTGCAGGCCGCTCAGAGAGCAGTGACCCCTGGAGCTGGTGGTGACAGGA
GCCTACATCAAACCCACCCTCTCAGCCCAGCCCAGCCCCGTGGTGAACTCA
GGAGGGAATGTAACCCTCCAGTGTGACTCACAGGTGGCATTTGATGGCTTC
ATTCTGTGTAAGGAAGGAGAAGATGAACACCCACAATGCCTG̲A̲G̲C̲TCCCA
GCCCCATGCCCGTGGGTCGTCCCGCGCCATCTTCTCCGTGGGCCCCGTGAG
CCCGAGTCGCAGGTGGTGGTACAGGTGCTATGCTTATGACTCGAACTCTCC
CTATGAGTGGTCTCTACCCAGTGATCTCCTGGAGCTCCTGGTCCTAT<u>AAGC
TT</u>GAATTCC
(SEQ ID NO: 13)

Figure 6

GATCTCGATCCCGCGAAATTAATACGACTCACTATAGGGAGACCACAACG
GTTTCCCTCTAGAAATAATTTTGTTTAACTTTAAGAAGGAGATATACATAT
GGGATCCATGGTAAGCTTGAATTCCGATCCGGCTGCTAACAAAGCCCGAA
AGGAAGCTGAGTTGGCTGCTGCCACCGCTGAGCAATAACTAGCATAACCC
CTTGGGGCCTCTAAACGGGTCTTGAGGGGTTTTTGCTGAAAGGAGGAACT
ATATCCGGATAATTCTTGAAGACGAAAGGGCCTCGTGATACGCCTATTTTT
ATAGGTTAATGTCATGATAATAATGGTTTCTTAGACGTCAGGTGGCACTTT
TCGGGGAAATGTGCGCGGAACCCCTATTTGTTTATTTTTCTAAATACATTC
AAATATGTATCCGCTCATGAGACAATAACCCTGATAAATGCTTCAATAATA
TTTTGTTAAAATTCGCGTTAAATTTTGTTAAATCAGCTCATTTTTTAACCA
ATAGGCCGAAATCGGCAAAATCCCTTATAAATCAAAAGAATAGACCGAGA
TAGGGTTGAGTGTTGTTCCAGTTTGGAACAAGAGTCCACTATTAAAGAACG
TGGACTCCAACGTCAAAGGGCGAAAAACCGTCTATCAGGGCGATGGCCCA
CTACGTGAACCATCACCCTAATCAAGTTTTTGGGGTCGAGGTGCCGTAAA
GCACTAAATCGGAACCCTAAAGGGAGCCCCGATTTAGAGCTTGACGGGG
AAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCA
CACCCGCCGCGCTTAATGCGCCGCTACAGGGCGCGTCAGGTGGCACTTTTC
GGGGAAATGTGCGCGGAACCCCTATTTGTTTATTTTTCTAAATACATTCAA
ATATGTATCCGCTCATGAGACAATAACCCTGATAAATGCTTCAATAATATT
GAAAAAGGAAGAGTATGAGTATTCAACATTTCCGTGTCGCCCTTATTCCCT
TTTTTGCGGCATTTTGCCTTCCTGTTTTGCTCACCCAGAAACGCTGGTGAA
AGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGTT
TTCCAATGATGAGCACTTTTAAAGTTCTGCTATGTGGCGCGGTATTATCCC
GTGTTGACGCCGGGCAAGAGCAACTCGGTCGCCGCATACACTATTCTCAG
AATGACTTGGTTGAGTACTCACCAGTCACAGAAAAGCATCTTACGGATGG
CATGACAGTAAGAGAATTATGCAGTGCTGCCATAACCATGAGTGATAACA
CTGCGGCCAACTTACTTCTGACAACGATCGGAGGACCGAAGGAGCTAACC
GCTTTTTTGCACAACATGGGGGATCATGTAACTCGCCTTGATCGTTGGGAA
CCGGAGCTGAATGAAGCCATACCAAACGACGAGCGTGACACCACGATGCC
TGCAGCAATGGCAACAACGTTGCGCAAACTATTAACTGGCGAACTACTTA
CTCTAGCTTCCCGGCAACAATTAATAGACTGGATGGAGGCGGATAAAGTT
GCAGGACCACTTCTGCGCTCGGCCCTTCCGGCTGGCTGGTTTATTGCTGAT
AAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCA
GGCAACTATGGATGAACGAAATAGACAGATCGCTGAGATAGGTGCCTCAC
TGATTAAGCATTGGTAACTGTCAGACCAAGTTTACTCATATATACTTTAGA
TTGATTTAAAACTTCATTTTAATTTAAAAGGATCTAGGTGAAGATCCTTTT
TGATAATCTCATGACCAAAATCCCTTAACGTGAGTTTTCGTTCCACTGAGC
GTCAGACCCCGTAGAAAAGATCAAAGGATCTTCTTGAGATCCTTTTTTTCT

Figure 6 (Cont)

GCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTAG
GCCACCACTTCAAGAACTCTGTAGCACCGCCTACATACCTCGCTCTGCTAA
TCCTGTTACCAGTGGCTGCTGCCAGTGGCGATAAGTCGTGTCTTACCGGGT
TGGACTCAAGACGATAGTTACCGGATAAGGCGCAGCGGTCGGGCTGAACG
GGGGGTTCGTGCACACAGCCCAGCTTGGAGCGAACGACCTACACCGAACT
GAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCG
CACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGG
GCGGAGCCTATGGAAAAACGCCAGCAACGCGGCCTTTTTACGGTTCCTGG
CCTTTTGCTGGCCTTTTGCTCACATGTTCTTTCCTGCGTTATCCCTGATTCT
GTGGATAACCGTATTACCGCCTTTGAGTGAGCTGATACCGCTCGCCGCAGC
CGAACGACCGAGCGCAGCGAGTCAGTGAGCGAGGAAGCGGAAGAGCGCC
TGATGCGGTATTTTCTCCTTACGCATCTGTGCGGTATTTCACACCGCAATGG
TGCACTCTCAGTACAATCTGCTCTGATGCCGCATAGTTAAGCCAGTATACA
CTCCGCTATCGCTACGTGACTGGGTCATGGCTGCGCCCCGACACCCGCCAA
CACCCGCTGACGCGCCCTGACGGGCTTGTCTGCTCCCGGCATCCGCTTACA
GACAAGCTGTGACCGTCTCCGGGAGCTGCATGTGTCAGAGGTTTTCACCGT
CATCACCGAAACGCGCGAGGCAG
(SEQ ID NO: 14)

Figure 8a

MGHLPKPTLWAEPGSVITMDQPVTLRCQGGQETQEYRLYREKKTAPWITRIP
QELVKKGQFPIPSITWEHAGRYRCYYGSDTSQWSASSDPLELVVTGVYIKPTL
SAQPSPVVNSGGNVTLQCDSQVAFDGFILCKEGEDEHPQCLNSQPHARGSSRA
IFSVGPVSPSRRWWYRCYAYDSNSPYEWSLPSDLLELLVL
(SEQ ID NO: 16)

Figure 8b

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 17)

Figure 8c

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDGC
(SEQ ID NO: 18)

Figure 9a

```
tacgtaatgggtcatcttccaaaaccaactctctgggctgaaccaggctctgtgatca
ccatggatcagcctgtgaccctcaggtgtcaggggggccaggagacccaggagtaccg
tctatatagagaaaagaaaacagcaccctggattacacggatcccacaggagcttgtg
aagaagggccagttccccatcccatccatcacctgggaacatgcagggcggtatcgct
gttactatggtagcgacactagtcaatggtcggcgagcagtgaccccctggagctggt
ggtgacaggagtctacatcaaacccaccctctcagcccagcccagcccgtggtgaac
tcaggagggaatgtaaccctccagtgtgactcacaggtggcatttgatggcttcattc
tgtgtaaggaaggagaagatgaacacccacaatgcctgaactcccagccccatgcccg
tgggtcgtcccgcgccatcttctccgtgggccccgtgagcccgagtcgcaggtggtgg
tacaggtgctatgcttatgactcgaactctccctatgagtggtctctacccagtgatc
tcctggagctcctggtcctatgttaagcggccgc
```
(SEQ ID NO: 19)

Figure 9b

MGHLPKPTLWAEPGSVITMDQPVTLRCQGGQETQEYRLYREKKTAPWITRIP
QELVKKGQFPIPSITWEHAGRYRCYYGSDTSQWSASSDPLELVVTGVYIKPTL
SAQPSPVVNSGGNVTLQCDSQVAFDGFILCKEGEDEHPQCLNSQPHARGSSRA
IFSVGPVSPSRRWWYRCYAYDSNSPYEWSLPSDLLELLVLC
(SEQ ID NO: 20)

Figure 13a

MGHLPKPTLWAEPGSVITLFQPVTLRCQGGQETQEYRLYREKKTAPWITRIPQ
ELVKKGQFPIPSITWEHAGRYRCYYGSDTAGRSESSDPLELVVTGAYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 21)

Figure 13b

MGHLPKPTLWAEPGSVITLSQPVTLRCQGGQETQEYRLYREKKTAPWITRIPQ
ELVKKGQFPIPSITWEHAGRYRCYYGSDTAGRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 22)

Figure 13c

MGHLPKPTLQAEPGSVITQGSPVTLRCQGGQETQEYRLYREKKTAPWITRIPQ
ELVKKGQFPIPSITWEHAGRYRCVIQRGTAGRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 23)

Figure 13d

MGHLPKPTLWAEPGSVITQGSPVTLRCQGGQETQEYRLYREKKTAPWITRIPQ
ELVKKGQFPIPSITWEHAGRYRCYYGSQGGLRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 24)

Figure 13e

MGHLPKPTLWAEPGSVITQGSPVTLRCQGGQETQEYRLYREKKTAPWITRIPQ
ELVKKGQFPIPSITWEHAGRYRCYYGTQTAGRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 25)

Figure 13f

MGHLPKPTLWAEPGSVITQGSPVTLRCQGGQETQEYRLYREKKTAPWITRIPQ
ELVKKGQFPIPSITWEHAGRYRCMQYTLTAGRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 26)

Figure 13g

MGHLPKPTLWAEPGSVITQGSPVTLRCQGGQETQEYRLYREKKTAPWITRIPQ
ELVKKGQFPIPSITWEHAGRYRCYYGSDTSQWSASSDPLELVVTGVYIKPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 27)

Figure 13h

MGHLPKPTLWAEPGSVITQGSPVTLRCQGGQETQEYRLYREKKTAPWITRIPQ
ELVKKGQFPIPSITWEHAGRYRCYYGSQGGLRSESSDPLELVVTGAYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 28)

Figure 13i

MGHLPKPTLWAEPGSVITQGSPVTLRCQGGQETQEYRLYREKKTAPWITRIPQ
ELVKKGQFPIPSITWEHAGRYRCYYGTQTAGRSESSDPLELVVTGAYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 29)

Figure 13j

MGHLPKPTLWAEPGSVITQGSPVTLRCQGGQETQEYRLYREKKTAPWITRIPQ
ELVKKGQFPIPSITWEHAGRYRCMQYTLTAGRSESSDPLELVVTGAYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 30)

Figure 13k

MGHLPKPTLWAEPGSVITMDQPVTLRCQGGQETQEYRLYREKKTAPWITRIP
QELVKKGQFPIPSITWEHAGRYRCYYGSQGGLRSESSDPLELVVTGVYIKPTLS
AQPSPVVNSGGNVTLQCDSQVAFDGFILCKEGEDEHPQCLNSQPHARGSSRAI
FSVGPVSPGRRWWYRCYAYDSNSPYEWSLPSDLLELLVL
(SEQ ID NO: 31)

Figure 13l

MGHLPKPTLWAEPGSVITMDQPVTLRCQGGQETQEYRLYREKKTAPWITRIP
QELVKKGQFPIPSITWEHAGRYRCYYGTQTAGRSESSDPLELVVTGVYIKPTLS
AQPSPVVNSGGNVTLQCDSQVAFDGFILCKEGEDEHPQCLNSQPHARGSSRAI
FSVGPVSPGRRWWYRCYAYDSNSPYEWSLPSDLLELLVL
(SEQ ID NO: 32)

Figure 13m

MGHLPKPTLWAEPGSVITMDQPVTLRCQGGQETQEYRLYREKKTAPWITRIP
QELVKKGQFPIPSITWEHAGRYRCVIQRGTAGRSESSDPLELVVTGVYIKPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 33)

Figure 13n

MGHLPKPTLWAEPGSVITMDQPVTLRCQGGQETQEYRLYREKKTAPWITRIP
QELVKKGQFPIPSITWEHAGRYRCMQYTLTAGRSESSDPLELVVTGVYIKPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 34)

Figure 13o

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYRQPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 35)

Figure 13p

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYLAPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 36)

Figure 13q

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYKAPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 37)

Figure 13r

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYQAPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 38)

Figure 13s

MGHLPKPTLWAEPGSVITQGAPVTLRCQGGQETQEYRLYREKKTAPWITRIPQ
ELVKKGQFPIPSITWEHAGRYRCYYGSDTAGRSESSDPLELVVTGVYIKPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 39)

Figure 13t

MGHLPKPTLWAEPGSVITQGRPVTLRCQGGQETQEYRLYREKKTAPWITRIPQ
ELVKKGQFPIPSITWEHAGRYRCYYGSDTAGRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 40)

Figure 13u

MGHLPKPTLWAEPGSVITVGQPVTLRCQGGQETQEYRLYREKKTAPWITRIPQ
ELVKKGQFPIPSITWEHAGRYRCYYGSDTAGRSESSDPLELVVTGVYIKPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 41)

Figure 13v

MGHLPKPTLWAEPGSVITLGQPVTLRCQGGQETQEYRLYREKKTAPWITRIPQ
ELVKKGQFPIPSITWEHAGRYRCYYGSDTAGRSESSDPLELVVTGVYIKPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 42)

Figure 13w

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGVYIKPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 43)

Figure 13x

MGHLPKPTLWAEPGSVITQGSPVTLRCQGGQETQEYRLYREKKTAPWITRIPQ
ELVKKGQFPIPSVTWEHAGRYRCYYGSDTAGRSESSDPLELVVTGVYIKPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 44)

Figure 13y

MGHLPKPTLWAEPGSVITQGSPVTLRCQGGQETQEYRLYREKKTAPWITRIPQ
ELVKKGQFPIPSITWEHAGRYRCVGWAVTAGRSESSDPLELVVTGVYIKPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 45)

Figure 13z

MGHLPKPTLWAEPGSVITQGSPVTLRCQGGQETQEYRLYREKKTAPWITRIPQ
ELVKKGQFPIPSITWEHAGRYRCIGRSQTAGRSESSDPLELVVTGVYIKPTLSA
QPSPVVNSGGNVTLQCDSQVAFDGFILCKEGEDEHPQCLNSQPHARGSSRAIFS
VGPVSPSRXWWYRCYAYDSNSPYEWSLPSDLLELLVL
(SEQ ID NO: 46)

Figure 13aa

MGHLPKPTLWAEPGSVITQGSPVTLRCQGGQETQEYRLYREKKTAPWITRIPQ
ELVKKGQFPIPSITWEHAGRYRCYYGQEGARSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 47)

Figure 13ab

MGHLPKPTLWAEPGSVITQGSPVTLRCQGGQETQEYRLYREKKTAPWITRIPQ
ELVKKGQFPIPSITWEHAGRYRCQGVSQTAGRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 48)

Figure 13ac

MGHLPKPTLWAEPGSVITQGSPVTLRCQGGQETQEYRLYREKKTAPQITRIPQ
ELVKKGQFPIPSITWEHAGRYRCYYGSDTAGRSESSDPLELVVTGVYVAPTLS
AQPSPVVNSGGNVTLQCDSQVAFDGFILCKEGEDEHPQCLNSQPHARGSSRAI
FSVGPVSPGRRWWYRCYAYDSNSPYEWSLPSDLLELLVL
(SEQ ID NO: 49)

Figure 13ad

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYKAPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 50)

Figure 13ae

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYQRPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 51)

Figure 13af

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYQAPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 52)

Figure 13ag

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYLQPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 53)

Figure 13ah

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYKQPTLSA
QPSPVVNSGGNVTLQCDSQVAFDGFILCKEGEDEHPQCLNSQPHARGSSRAIFS
VGPVSPGRRWWYRCYAYDSNSPYEWSLPSDLLELLVL
(SEQ ID NO: 54)

Figure 13ai

MGHLPKPTLWAEPGSVITQGSPVTLRCQGGQETQEYRLYREKKTAPWITRIPQ
ELVKKGQFPIPSITWEHAGRYRCYYGSDTAGRSESSDPLELVVTGIYQKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 55)

Figure 13aj

MGHLPKPTLWAEPGSVITMDQPVTLRCQGGQETQEYRLYREKKTAPWITRIP
QELVKKGQFPIPSITWEHAGRYRCYYGSDTAGRSESSDPLELVVTGIYLAPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 56)

Figure 13ak

MGHLPKPTLWAEPGSVITLGQPVTLRCQGGQETQEYRLYREKKTAPWITRIPQ
ELVKKGQFPIPSITWEHAGRYRCYYGSDTAGRSESSDPLELVVTGIYLAPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 57)

Figure 13al

MGHLPKPTLWAEPGSVITMDQPVTLRCQGGQETQEYRLYREKKTAPWITRIP
QELVKKGQFPIPSITWEHAGRYRCYYGSDTSQWSASSDPLELVVTGIYLAPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 58)

Figure 13am

MGHLPKPTLWAEPGSVITLGQPVTLRCQGGQETQEYRLYREKKTAPWITRIPQ
ELVKKGQFPIPSITWEHAGRYRCYYGSDTSQWSASSDPLELVVTGIYLAPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 59)

Figure 13an

MGHLPKPTLWAEPGSVITMDQPVTLRCQGGQETQEYRLYREKKTAPWITRIP
QELVKKGQFPIPSITWEHAGRYRCIGRSQTSQWSASSDPLELVVTGIYLAPTLS
AQPSPVVNSGGNVTLQCDSQVAFDGFILCKEGEDEHPQCLNSQPHARGSSRAI
FSVGPVSPSRRWWYRCYAYDSNSPYEWSLPSDLLELLVL
(SEQ ID NO: 60)

Figure 13ao

MGHLPKPTLWAEPGSVITLGQPVTLRCQGGQETQEYRLYREKKTAPWITRIPQ
ELVKKGQFPIPSITWEHAGRYRCIGRSQTSQWSASSDPLELVVTGIYLAPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELLVL
(SEQ ID NO: 61)

Figure 13ap

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 62)

Figure 13aq

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWRYRCYAYDSNSPYEWSLPSDLLELDVDG
(SEQ ID NO: 63)

Figure 13ar

MHLPKPTLWAEPGSVITMDQPVTLRCQGGQETQEYRLYREKKTAPWITLIPQE
LVKKGQFPIPSITWEHAGRYRCYYGSDTSQWSASSDPLELVVTGVYIKPTLSA
QPSPVVNSGGNVTLQCDSQVAFDGFILCKEGEDGHPQCLNSQPHARGSSRAIF
SVGPVSPSRRWWYWCYAYDSNSPYEWSLPSDLLELDVDG
(SEQ ID NO: 64)

Figure 13as

MHLPKPTLWAEPGSVITMDQPVTLRCQGGQETQEYRLYERKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 65)

Figure 13at

MHLPKPTLWAEPGSVITLGQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 66)

Figure 13au

MHLPKPTLWAEPGSVITLGSPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 67)

Figure 13av

MHLPKPTLWAEPGSVITLRSPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 68)

Figure 13aw

MHLPKPTLWAEPGSVITLQSPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 69)

Figure 13ax

MHLPKPTLWAEPGSVITLESPVTLRCQGGQETQEYRLYREKKTAPWITRIPQEL
VKKGQFPIPSITWEHAGRYRCYYGSDTSQWSASSDPLELVVTGVYIKPTLSAQ
PSPVVNSGGNVTLQCDSQVAFDGFILCKEGEDEHPQCLNSQPHARGSSRAIFSV
GPVSPSRRWWYRCYAYDSNSPYEWSLPSDLLELDVDG
(SEQ ID NO: 70)

Figure 13ay

MHLPKPTLWAEPGSVITMDQPVTLRCQGGQETQEYRLYREKKTAPWITRIPQE
LVKKGQFPIPSITWEHAGRYRCYYGTQTAGRSESSDPLELVVTGVYIKPTLSAQ
PSPVVNSGGNVTLQCDSQVAFDGFILCKEGEDEHPQCLNSQPHARGSSRAIFSV
GPVSPSRRWWYRCYAYDSNSPYEWSLPSDLLELDVDG
(SEQ ID NO: 71)

Figure 13az

MHLPKPTLWAEPGSVITMDQPVTLRCQGGQETQEYRLYREKKTAPWITRIPQE
LVKKGQFPIPSITWEHAGRYRCMQYTLTAGRSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 72)

Figure 13ba

MHLPKPTLWAEPGSVITMDQPVTLRCQGGQETQEYRLYREKKTAPWITRIPQE
LVKKGQFPIPSITWEHAGRYRCVIQRGTAGRSESSDPLELVVTGVYIKPTLSAQ
PSPVVNSGGNVTLQCDSQVAFDGFILCKEGEDEHPQCLNSQPHARGSSRAIFSV
GPVSPSRRWWYRCYAYDSNSPYEWSLPSDLLELDVDG
(SEQ ID NO: 73)

Figure 13bb

MHLPKPTLWAEPGSVITMDQPVTLRCQGGQETQEYRLYREKKTAPWITRIPQE
LVKKGQFPIPSITWEHAGRYRCYYGGQEGARSESSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 74)

Figure 13bc

MHLPKPTLWAEPGSVITMDQPVTLRCQGGQETQEYRLYREKKTAPWITRIPQE
LVKKGQFPIPSITWEHAGRYRCYYGTQTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSLPSDLLELDVDG
(SEQ ID NO: 75)

Figure 13bd

MGHLPKPTLWAEPGSVITMDQPVTLRCQGGQETQQYRLYREKKTAPWITRIP
QELVKKGQFPIPSITWEHAGRYRCYYGSDTRQWSASSDPLELVVTGVYIKPTL
SAQPSPVVNSGGNVTLQCDSQVAFDGFILCKEGEDDHPQCLNSQPHARGSSRA
IFSVGPVSPSRRWRYRCYAYDSNSPYEWSLPSDLLELDVDG
(SEQ ID NO: 76)

Figure 13be

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCDNSQPHARGSSRAIF
SVGPVSPSRRWWYRCYAYDSNSPYEWSLPSDLLELDVDG
(SEQ ID NO: 77)

Figure 13bf

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAEF
SVGPVSPSRRWWYRCYAYDSNSPYEWSLPSDLLELDVDG
(SEQ ID NO: 78)

Figure 13bg

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILCKEGEDEHPQCLNSQPHARGSSRAIFS
VGPVSPSRRWWYRCYAYDSNSPYEWSDPSDLLELDVDG
(SEQ ID NO: 79)

Figure 13bh

MHLPKPTLWAEPGSVITMDQPVTLRCQGGQETQEYRLYREKKTAPWITRIPQE
LVKKGQFPIPSITWEHAGRYRCYYGSDTSQWSASSDPLELVVTGVYIKPTLSA
QPSPVVNSGGNVTLQCDSQVAFDGFILSKEGEDEHPQSLNSQPHARGSSRAIFS
VGPVSPSRRWWYRCYAYDSNSPYEWSLPSDLLELDVDG
(SEQ ID NO: 80)

といった

MODIFIED LEUKOCYTE IG-LIKE RECEPTOR FAMILY MEMBERS (LIRS) WITH INCREASED AFFINITY FOR CLASS 1 MHC AND THEIR USES IN MODULATING T-CELL ACTIVATION

This application is a national phase application of PCT/GB2006/001860 filed May 19, 2006, which was published in English under PCT Article 21(2) on Nov. 30, 2006 and which claims the benefit of GB 0510627.3 filed May 25, 2005.

The present invention relates to polypeptides having the property of binding to a given Class I pMHC CHARACTERISED IN THAT said polypeptide has a $K_D$ for the said given Class I pMHC of less than or equal to 1 μM and/or has an off-rate ($k_{off}$) for the said given Class I pMHC molecule of 2 $S^{-1}$ or slower AND said polypeptide has at least a 45% identity and/or 55% similarity to SEQ ID NO: 7 AND said polypeptide inhibits CD8 binding to the given pMHC to a greater extent than the polypeptide SEQ ID NO: 3. Also provided are multivalent complexes of said polypeptides, cells presenting said polypeptides, said polypeptides associated with therapeutic agents and methods for using these polypeptides.

BACKGROUND TO THE INVENTION

Immunoglobulin-like transcripts (ILTs) are also known as Leukocyte Immunoglobulin-like receptors (LIRs), monocyte/macrophage immunoglobulin-like receptors (MIRs) and CD85. This family of immunoreceptors form part of the immunoglobulin superfamily. The identification of ILT molecules was first published in March 1997 in a study (Samaridis et al., (1997) *Eur J Immunol* 27 660-665) which detailed the sequence of LIR-1 (ILT-2), noted their similarity to bovine FCγ2R, human killer cell inhibitory receptors (KIRs), human FcαR, and mouse gp49. This study also noted that LIR-1, unlike KIRs, is predominately expressed on monocytic and B lymphoid cells.

Soluble polypeptides with the pMHC binding characteristics of ILT molecules and multivalent complexes thereof provide a means of blocking the CD8 binding site on pMHC molecules, for example for the purpose of inhibiting CD8+ T cell-mediated automimmune disease. However, for that purpose it would be desirable if these polypeptides had a higher affinity and/or a slower off-rate for the target pMHC molecules than native ILT molecules.

BRIEF DESCRIPTION OF THE INVENTION

The present invention relates to polypeptides having the property of binding to a given Class I pMHC CHARACTERISED IN THAT said polypeptide has a $K_D$ for the said given Class I pMHC of less than or equal to 1 μM and/or has an off-rate ($k_{off}$) for the said given Class I pMHC molecule of 2 $S^{-1}$ or slower AND said polypeptide has at least a 45% identity and/or 55% similarity to SEQ ID NO: 7 AND said polypeptide inhibits CD8 binding to the given pMHC to a greater extent than the polypeptide SEQ ID NO: 3. Also provided are multivalent complexes of said polypeptides, cells presenting said polypeptides, said polypeptides associated with therapeutic agents and methods for using these polypeptides.

DETAILED DESCRIPTION OF THE INVENTION

As noted above ILT molecules are also known as LIRs, MIRs and CD85. The term ILT as used herein is understood to encompass any polypeptide within this family of immunoreceptors.

ILTs

The ILT family of immunoreceptors are expressed on the surface of lymphoid and myeloid cells. The ILT molecules share 63-84% homology in their extracellular regions and all except the soluble LIR-4 are type I transmembrane proteins. All the currently identified ILT molecules have either two or four immunoglobulin superfamily domains in their extracellular regions. (Willcox et al., (2003) 4 (9) 913-919) Individual ILT molecules may also be expressed as a number of distinct variants/isoforms. (Colonna et al., (1997) *J Exp Med* 186 (11) 1809-1818) and (Cosman et al., (1997) *Immunity* 7 273-282)

There are a number of scientific papers detailing the structure and function of ILT molecules including the following: (Samaridis et al., (1997) *Eur J Immunol* 27 660-665), (Cella, et al., (1997) *J Exp Med* 185 (10) 1743-1751), (Cosman et al., (1997) Immunity 7 273-282), (Borges et al., (1997) *J Immunol* 159 5192-5196), (Colonna et al., (1997) J Exp Med 186 (11) 1809-1818), (Colonna et al., (1998) *J Immunol* 160 3096-3100), (Cosman et al., (1999) *Immunological Revs* 168 177-185), (Chapman et al., (1999) *Immunity* 11 603-613), (Chapman et al., (2000) *Immunity* 12 727-736), (Willcox et al., (2002) *BMC Structural Biology* 2 6), (Shiroshi et al., (2003) *PNAS* 100 (5) 8856-8861) and (Willcox et al., (2003) 4 (9) 913-919).

WO9848017 discloses the genetic sequences encoding ILT family members and their deduced amino acid sequences. This application classified LIR molecules into three groups. The first group containing polypeptides with a transmembrane region including a positively charged residue and a short cytoplasmic tail. The second group comprising polypeptides having a non-polar transmembrane region and a long cytoplasmic tail. And finally a third group containing a polypeptide expressed as a soluble polypeptide having no transmembrane region or cytoplasmic tail. Also disclosed were processes for producing polypeptides of the LIR family, and antagonistic antibodies to LIR family members. This application discussed the possible use of LIR family members to treat autoimmune diseases and disease states associated with suppressed immune function. In this regard, it was noted that the use of soluble forms of an LIR family member is advantageous for certain applications. These advantages included the ease of purifying soluble forms of ILTs/LIRs from recombinant host cells, that they are suitable for intravenous administration and their potential use to block the interaction of cell surface LIR family members with their ligands in order to mediate a desirable immune function. The possible utility of soluble LIR fragments that retain a desired biological activity, such as binding to ligands including MHC class I molecules was also noted.

Another study (Shiroishi et al (2003) *PNAS* 100 (15) 8856-8861) discussed soluble (truncated) forms of ILT-2 and ILT-4 molecules. Their ability to compete with soluble CD8 for binding to MHC molecules in Biacore studies was noted and it was postulated that this may be one of the mechanisms by which ILT-2 modulates CD8+ T cell activation. In relation to pMHC binding this study states "The higher affinity of ILT versus CD8 binding suggests that ILTs may effectively block CD8 binding at the cell surface. This study noted that ILT2 binds to the α3 domain of Class I MHC and that the crystal structure of an ILT2 fragment containing domains 1 and 2 had been reported.

(Colonna et al., (1998) *J. Immunol.* 160 3096-3100) which focussed on ILT-4, contains a summary of the tissue distribution and specificity of ILTs 2-5. Of these ILT molecules, ILT-2 and ILT-4 are noted to bind Class I MHC molecules. This study analysed the binding of soluble ILT-4 to cells transfected with various Class I MHCs. The study concluded that ILT-4 binds to HLAs-A, B and G, but not HLA-Cw3 or HLA-Cw5.

WO03041650 discloses a method of treating Rheumatoid Arthritis (RA) using modulators of LIR-2 and/or LIR-3/LIR-7 activity. The modulators disclosed include both agonists and antagonists of LIR activity. WO2006033811 discloses the use of ILT-3 polypeptides and fusions thereof as therapeutic agents for the inhibition of graft rejection.

The affinity for various soluble analogues of Wild-Type ILT molecules for different pMHC targets has been determined. For example, (Chapman et al., (1999) Immunity 11 603-613) used Biacore-based methods to determine that LIR-1 (ILT-2) bound to a range of HLA-A, HLA-B, HLA-C, HLA-E and HLA-G molecules. The determined $K_D$ values for these interactions ranged from $1\times10^{-4}$ M (for HLA-G1) to $2\times10^{-5}$ M (for HLA-Cw*0702). This study also noted that the $K_D$ of the interaction between ILT-2 had an affinity for UL18, a viral analogue of Class I MHC, in the nM range.

A further study (Chapman et al., (2000) *Immunity* 12 727-736) reported the crystal structure of a truncated LIR-1 (ILT-2) polypeptide comprising the D1 and D2 domains. LIR-1 was known to bind to the UL18 viral class I MHC analogue with much higher affinity than the similar LIR-2. The authors used the crystal structure of the truncated LIR-1 polypeptide to identify differences between LIR-1 and LIR-2 that occurred in solvent-exposed residues. Site-directed mutagenesis of these two peptides was the used to confirm which residues were involved in UL18 binding. This was carried out by substituting WT residues from LIR-1 in to the corresponding amino acid positions of LIR-2. The study concluded that residue 38Y, and at least one of 76Y, 80D or 83R of LIR-1 were involved in UL18 binding. The authors stated that "Because the affinity of LIR-1 for class I MHC proteins is much lower than for UL18 we were unable to derive accurate affinities for the binding of the LIR-1 and LIR-2 mutants to class I MHC."

The full amino acid and DNA sequences of a Wild-Type human ILT-2 are shown in FIGS. 1*a* (SEQ ID NO:1) and 1*b* (SEQ ID NO:2) respectively. The DNA sequence provided corresponds to that given accession number NM_006669 on the NCBI nucleotide database.

High Affinity ILT-Like Polypeptides

The present invention provides polypeptides having the property of binding to a given Class I pMHC CHARACTERISED IN THAT said polypeptide has a $K_D$ for the said given Class I pMHC of less than or equal to 1 μM and/or has an off-rate ($k_{off}$) for the said given Class I pMHC molecule of 2 $S^{-1}$ or slower AND said polypeptide has at least a 45% identity and/or 55% similarity to SEQ ID NO: 7 AND said polypeptide inhibits CD8 binding to the given pMHC to a greater extent than the polypeptide SEQ ID NO: 3.

Polypeptides which meet the above homology and Class I pMHC-binding criteria may be regarded as high affinity ILT-like molecules and may be referred to herein as such.

As stated above, naturally occurring ILT polypeptides have either two or four immunoglobulin superfamily domains in their extracellular regions. The high affinity ILT-like polypeptides of the invention may be expressed in forms having four, three or two of said domains. The currently preferred embodiments of the invention have two immunoglobulin superfamily domains corresponding to the two N-terminal domains of human ILT-2 containing one or more mutation(s) which confer high affinity for Class I pMHC. These N-terminal domains are domains one and two using the notation of Cosman et al., (1999) *Immunol Revs* 168: 177-185. ILT-like polypeptides having those two N-terminal domains generally have a sequence corresponding to amino acids 1-195 of SEQ ID NO: 3.

Preferably, the polypeptide is CHARACTERISED IN THAT said polypeptide has at least a 60% identity and/or 75% similarity to SEQ ID NO: 7

Preferably, the polypeptide is CHARACTERISED IN THAT said polypeptide has at least a 75% identity and/or 85% similarity to SEQ ID NO: 7.

Preferably, the polypeptide is CHARACTERISED IN THAT said polypeptide has at least a 90% identity and/or 95% similarity to SEQ ID NO: 7.

Sequence identity as used herein means identical amino acids at corresponding positions in the two sequences which are being compared. Similarity in this context includes amino acids which are identical and those which are similar (functionally equivalent). For example a single substitution of one hydrophobic amino acid present at a given position in a polypeptide with a different hydrophobic amino acid would result in the formation of a polypeptide which was considered similar to the original polypeptide but not identical). The parameters "similarity" and "identity" as used herein to characterise polypeptides of the invention are determined by use of the FASTA algorithm as implemented in the FASTA programme suite available from William R. Pearson, Department of Biological Chemistry, Box 440, Jordan Hall, Charlottesville, Va. The settings used for determination of those parameters via the FASTA programme suite are as specified in Example 6 herein.

As will be obvious to those skilled in the art there are a number of sources of FASTA protein: protein comparisons which could be used for this analysis. (Pearson et al., (1988) *PNAS* 85 2444-2448) provides further details of the FASTA algorithm. The relative inhibitory activities of the polypeptide of SEQ ID NO 3 and any given putative polypeptide of the invention may be determined by any conventional assay from which the read-out is related to the binding affinity of CD8 for the given pMHC. In general the read-out will be an $IC_{50}$ value. The test polypeptide and that of SEQ ID NO: 3 will be assessed at comparable concentrations and their respective $IC_{50}$'s determined by reference to the inhibition curves plotted from the individual results. A suitable assay is that described in Example 5.

Preferably, the polypeptide is CHARACTERISED IN THAT said polypeptide has a $K_D$ for the said given Class I pMHC of less than or equal to 100 nM and/or has an off-rate ($k_{off}$) for the said given Class I pMHC of 0.1 $S^{-1}$.

As will be known to those skilled in the art there are a number of means by which said affinity and/or off-rate can be determined. For example, said affinity ($K_D$) and/or off-rate ($k_{off}$) may be determined by Surface Plasmon Resonance. Example 4 herein provides a Biacore-based assay suitable for carrying out such determinations For comparison the interaction of a soluble truncated variant of the Wild-Type ILT-2 molecule (see FIG. 2*a* (SEQ ID NO: 3) for the amino acid sequence of this soluble polypeptide) and HLA-A*0201 loaded with the Carcinoembryonic antigen (CEA)-derived YLSGANLNL (SEQ ID NO: 13) peptide has a $K_D$ of 6 μM, and an off-rate ($k_{off}$) of 2.4 $S^{-1}$ as measured by the Biacore-based method of Example 4. This soluble ILT-2 molecule is a truncated form of a variant of isoform 1 of Wild Type human ILT-2 which contains only extracellular domains D1 and D2. The amino acid residues which differ between this ILT-2 variant molecule and those of isoform 1 of ILT-2 are highlighted in FIG. 1*a*.

FIG. 2*b* (SEQ ID NO: 4) details the native DNA sequence encoding this polypeptide. In order to improve the efficiency of recombinant expression and to facilitate cloning of this polypeptide a number of mutations were introduced into the DNA encoding this polypeptide. These mutations do not alter the amino acid sequence of the expressed polypeptide. The DNA sequence used for recombinant expression is shown in FIG. 3 (SEQ ID NO: 5)

One embodiment of the invention is provided wherein the polypeptide is a mutated human ILT molecule. For example, the DNA encoding human ILT-2, or soluble fragments thereof, can be used as a template into which the various mutations that cause high affinity and/or a slow off-rate for the interaction between the high affinity ILT-like polypeptides of the invention and the target pMHC complex can be introduced. Thus the invention includes ILT-2 variants which are mutated relative to the native sequence.

As will be obvious to those skilled in the art the mutation(s) in such human ILT-2 amino acid sequence may be one or more of substitution(s), deletion(s) or insertion(s). These mutations can be carried out using any appropriate method including, but not limited to, those based on polymerase chain reaction (PCR), restriction enzyme-based cloning, or ligation independent cloning (LIC) procedures. These methods are detailed in many of the standard molecular biology texts. For further details regarding polymerase chain reaction (PCR) mutagenesis and restriction enzyme-based cloning see (Sambrook & Russell, (2001) Molecular Cloning—A Laboratory Manual ($3^{rd}$ Ed.) CSHL Press) Further information on LIC procedures can be found in (Rashtchian, (1995) *Curr Opin Biotechnol* 6 (1): 30-6)

Further embodiments of the invention include polypeptides wherein one or more of amino acids corresponding to 10W, 19Q, 20G, 21S, 42K, 47W, 50R, 66I, 77Y, 78Y, 79G, 80S, 81D, 82T, 83A, 84G, 85R, 87E, 99A, 101I, 102K, 141E, 146L, 147N, 159I, 168S, 172W, 174R and 188L of SEQ ID NO: 3 is/are mutated. For example, polypeptides of the invention may comprise one or more of the following mutations: 10W→L, 19Q→M, 19Q→L, 19Q→V, 20G→D, 20G→M, 20G→Q, 20G→F, 20G→S, 20G→E, 20G→R, 21S→Q, 21S→R, 21S→A, 21S→S, 42K→R, 47W→Q, 50R→L, 66L→V, 77Y→V, 77Y→M, 77Y→I, 77Y→Q, 78Y→Q, 78Y→I, 78Y→G, 79G→Q, 79G→Y, 79G→W, 79G→R, 79G→V, 80S→R, 80S→T, 80S→G, 81D→G, 81D→Q, 81D→L, 81D→V, 82T→G, 82T→E, 83A→S, 83A→G, 83A→R, 84G→L, 84G→Q, 84G→A, 85R→W, 87E→A, 99A→I, 99A→Y, 101I→L, 101I→K, 101I→Q, 101I→V, 102K→Q, 102K→A, 102K→R, 141E→G, 141E→D, 146L→D, 147N→S, 159I→E, 168S→G, 172W→R, 174R→W or 188L→D.

For example, polypeptides comprising at least two, three, four, five, six, seven, eight, nine or ten of the above mutations will often be suitable.

The numbering used is the same as that shown in FIG. 2a (SEQ ID No: 3).

One embodiment provides a polypeptide of the invention comprising mutations corresponding to amino acids 19Q→M and 21 S→Q using the numbering of SEQ ID NO: 3.

Another embodiment provides a polypeptide of the invention comprising mutations corresponding to 19Q→M, 20G→D, 21S→Q, 99A→V and 168S→G using the numbering of SEQ ID NO: 3.

Another embodiment provides a polypeptide of the invention comprising mutations corresponding to 19Q→L, 20G→M, and 21S→Q using the numbering of SEQ ID NO: 3.

Another embodiment provides a polypeptide of the invention mutations corresponding to 19Q→M, 20G→Q, 21S→R, 42K→R, and 146L→S using the numbering of SEQ ID NO: 3.

Another embodiment provides a polypeptide of the invention comprising mutations corresponding to 19Q→M, 20G→D, 21S→Q, 83A→S, 84G→Q, 85R→W, 87E→A and 99A→V using the numbering of SEQ ID NO: 3.

A further embodiment is provided by a polypeptide wherein amino acids corresponding to one or both of 135C or 145C using the numbering of SEQ ID NO: 3. is/are mutated to S.

Another embodiment is provided by a polypeptide of the invention comprising amino acids corresponding to at least amino acids 1-195 of SEQ ID No: 3. Such polypeptides are two-domain embodiments comprising domains corresponding to the two N-terminal immunoglobulin superfamily domains of human ILT-2.

Further specific embodiments of the invention are provided by polypeptides which consist of or include any of SEQ ID Nos: 6 to 9, or 21 to 61. Of course, although these preferred embodiments are expressed as consisting of or including SEQ ID Nos: 6 to 9, 16, or 21 to 61 those skilled in the art will appreciate that it is inevitable that there will be minor amino acid substitutions, deletions and insertions which do not affect the overall identity and properties of the embodiment. Such minor variations may be regarded as phenotypically silent variations of such polypeptides. Looked at another way, such variations result in a polypeptide which has the same function as the parent and achieves that function in the same way, A preferred embodiment of the invention is provided by a polypeptide which consists of or includes SEQ ID No: 16.

High Affinity ILT-Like Polypeptides with Enhanced Solubility

The polypeptides of the invention may be used as soluble therapeutics. In such instances is desirable to increase the solubility of these polypeptides. The invention encompasses polypeptides which comprise one or more mutation(s) which increase the solubility of the polypeptide relative to a corresponding polypeptide lacking said mutations. As will be known to those skilled in the art when increased solubility of a polypeptide is sought it is generally preferable to mutate amino acids which are solvent exposed. These solvent exposed amino acids can be identified by reference to the crystal structure of ILT-2. (See Chapman et al., (2000) *Immunity* 12 727-736) The invention encompasses polypeptides wherein one or more solvent-exposed amino acid(s) are mutated. For example, polypeptides of the invention comprising at least one mutation wherein a solvent exposed hydrophobic amino acid is substituted by a charged amino acid.

Preferably, such solubility enhancing mutations are in within the C-terminal 6 amino acids of the polypeptides of the invention.

Another embodiment is provided by a polypeptide of the invention wherein amino acids corresponding to 196L and/or 198L of SEQ ID NO: 3 are mutated to 196D and 198D respectively.

A further embodiment is provided by a polypeptide of the invention comprising mutations corresponding to 19Q→M, 20G D, 21S→Q, 83A→S, 84G→Q, 85R→W, 87E→A, 99A→V, 196L→D and 198L→D using the numbering of SEQ ID NO: 3.

Another embodiment is provided by a polypeptide of the invention consisting of or including any of SEQ ID Nos: 63 to 80.

Another embodiment is provided by a polypeptide of the invention consisting of or including SEQ ID Nos: 17 or 62.

"Tagged" High Affinity ILT-Like Polypeptides

The polypeptides of the invention may be used in multimeric forms or in association with other moieties. In this regard it is desirable to produce polypeptides of the invention which comprising a means of attaching other moieties thereto.

Therefore, one embodiment is provided by a polypeptide of the invention which comprises comprising a "tag" to facilitate the attachment of other moieties. This tag may be on the C-terminal of the polypeptides.

As will be known to those skilled in the art there are many tags which are suitable for this purpose. These include, but are not limited to, cysteine residues, hexahistidine peptides, biotin and chemically reactive groups. The presence of such tags may also facilitate purification of the polypeptides.

PEGylated High Affinity ILT-Like Polypeptides

In one particular embodiment a polypeptide of the invention is associated with at least one polyalkylene glycol chain(s). This association may be caused in a number of ways known to those skilled in the art. In a preferred embodiment the polyalkylene chain(s) is/are covalently linked to the polypeptides. In a further embodiment the polyethylene glycol chains of the present aspect of the invention comprise at least two polyethylene repeating units.

Multivalent High Affinity ILT-Like Complexes

One aspect of the invention provides a multivalent complex comprising at least two polypeptides of the invention, said multivalent complex having a $K_D$ for a given Class I pMHC of less than or equal to 1 μM and/or has an off-rate ($k_{off}$) for the said Class I pMHC of 2 $S^{-1}$ or slower.

In one embodiment of this aspect, at least two polypeptides of the invention are linked via linker moieties to form multivalent complexes.

One aspect is provided wherein the polypeptides of the invention are linked by a non-peptidic polymer chain or a peptidic linker sequence. Preferably the multivalent complexes are water soluble, so the linker moiety should be selected accordingly. Furthermore, it is preferable that the linker moiety should be capable of attachment to defined positions on the polypeptides, so that the structural diversity of the complexes formed is minimised. One embodiment of the present aspect is provided by a multivalent complex of the invention wherein the polymer chain or peptidic linker sequence extends between amino acid residues of each polypeptide which are not located in the Class I pMHC binding domain of the polypeptides.

Since the complexes of the invention may be for use in medicine, the linker moieties should be chosen with due regard to their pharmaceutical suitability, for example their immunogenicity.

Examples of linker moieties which fulfil the above desirable criteria are known in the art, for example the art of linking antibody fragments.

There are two classes of linker that are preferred for use in the production of multivalent complexes of the present invention. A multivalent complex of the invention in which the polypeptides are linked by a polyalkylene glycol chain or a peptidic linker derived from a human multimerisation domain provide certain embodiments of the invention.

Suitable hydrophilic polymers include, but are not limited to, polyalkylene glycols. The most commonly used polymers of this class are based on polyethylene glycol or PEG, the structure of which is shown below.

HOCH$_2$CH$_2$—O—(CH$_2$CH$_2$O)$_n$—CH$_2$CH$_2$OH

Wherein n is greater than two.

However, others are based on other suitable, optionally substituted, polyalkylene glycols include polypropylene glycol, and copolymers of ethylene glycol and propylene glycol.

Such polymers may be used to treat or conjugate therapeutic agents, particularly polypeptide or protein therapeutics, to achieve beneficial changes to the pharmaco-kinetic (PK) profile of the therapeutic, for example reduced renal clearance, improved plasma half-life, reduced immunogenicity, and improved solubility. Such improvements in the PK profile of the PEG-therapeutic conjugate are believe to result from the PEG molecule or molecules forming a 'shell' around the therapeutic which sterically hinders the reaction with the immune system and reduces proteolytic degradation. (Casey et al, (2000) Tumor Targeting 4 235-244) The size of the hydrophilic polymer used may in particular be selected on the basis of the intended therapeutic use of the high affinity ILT-like polypeptides. There are numerous review papers and books that detail the use of PEG and similar molecules in pharmaceutical formulations. For example, see (Harris (1992) *Polyethylene Glycol Chemistry—Biotechnical and Biomedical Applications*, Plenum, New York, N.Y.) or (Harris & Zalipsky (1997) *Chemistry and Biological Applications of Polyethylene Glycol* ACS Books, Washington, D.C.).

The polymer used can have a linear or branched conformation. Branched PEG molecules, or derivatives thereof, can be induced by the addition of branching moieties including glycerol and glycerol oligomers, pentaerythritol, sorbitol and lysine.

Usually, the polymer will have a chemically reactive group or groups in its structure, for example at one or both termini, and/or on branches from the backbone, to enable the polymer to link to target sites in the high affinity ILT-like polypeptide. This chemically reactive group or groups may be attached directly to the hydrophilic polymer, or there may be a spacer group/moiety between the hydrophilic polymer and the reactive chemistry as shown below:

Reactive chemistry-Hydrophilic polymer-Reactive chemistry

Reactive chemistry-Spacer-Hydrophilic polymer-Spacer-Reactive chemistry

The spacer used in the formation of constructs of the type outlined above may be any organic moiety that is a non-reactive, chemically stable, chain, Such spacers include, by are not limited to the following:

—(CH$_2$)$_n$— wherein n=2 to 5

—(CH$_2$)$_3$NHCO(CH$_2$)$_2$

A multivalent complex of the invention in which a divalent alkylene spacer radical is located between the polyalkylene glycol chain and its point of attachment to a polypeptide molecule of the complex provides a further embodiment of the present aspect.

A multivalent complex of the invention in which the polyalkylene glycol chain comprises at least two polyethylene glycol repeating units provides a further embodiment of the present aspect.

There are a number of commercial suppliers of hydrophilic polymers linked, directly or via a spacer, to reactive chemistries that may be of use in the present invention. These suppliers include Nektar Therapeutics (CA, USA), NOF Corporation (Japan), Sunbio (South Korea) and Enzon Pharmaceuticals (NJ, USA).

Commercially available hydrophilic polymers linked, directly or via a spacer, to reactive chemistries that may be of use in the present invention include, but are not limited to, the following:

| PEG linker Description | Source of PEG | Catalogue Number |
|---|---|---|
| ILT-like Monomer attachment | | |
| 5K linear (Maleimide) | Nektar | 2D2MOHO1 |
| 20K linear (Maleimide) | Nektar | 2D2MOPO1 |
| 20K linear (Maleimide) | NOF Corporation | SUNBRIGHT ME-200MA |
| 20K branched (Maleimide) | NOF Corporation | SUNBRIGHT GL2-200MA |
| 30K linear (Maleimide) | NOF Corporation | SUNBRIGHT ME-300MA |
| 40K branched PEG (Maleimide) | Nektar | 2D3XOTO1 |
| 5K-NP linear (for Lys attachment) | NOF Corporation | SUNBRIGHT MENP-50H |
| 10K-NP linear (for Lys attachment) | NOF Corporation | SUNBRIGHT MENP-10T |
| 20K-NP linear (for Lys attachment) | NOF Corporation | SUNBRIGHT MENP-20T |
| ILT-like dimer linkers | | |
| 3.4K linear (Maleimide) | Nektar | 2D2DOFO2 |
| 5K forked (Maleimide) | Nektar | 2D2DOHOF |
| 10K linear (with orthopyridyl ds-linkers in place of Maleimide) | Sunbio | |
| 20K forked (Maleimide) | Nektar | 2D2DOPOF |
| 20K linear (Maleimide) | NOF Corporation | |
| 40K forked (Maleimide) | Nektar | 2D3XOTOF |
| Higher order ILT-like multimers | | |
| 15K, 3 arms, Mal₃ (for trimer) | Nektar | OJOONO3 |
| 20K, 4 arms, Mal₄ (for tetramer) | Nektar | OJOOPO4 |
| 40K, 8 arms, Mal₈ (for octamer) | Nektar | OJOOTO8 |

A wide variety of coupling chemistries can be used to couple polymer molecules to protein and peptide therapeutics. The choice of the most appropriate coupling chemistry is largely dependant on the desired coupling site. For example, the following coupling chemistries have been used attached to one or more of the termini of PEG molecules (Source: Nektar Molecular Engineering Catalogue 2003):

N-maleimide
Vinyl sulfone
Benzotriazole carbonate
Succinimidyl proprionate
Succinimidyl butanoate
Thio-ester
Acetaldehydes
Acrylates
Biotin
Primary amines As stated above non-PEG based polymers also provide suitable linkers for multimerising the polypeptides of the present invention. For example, moieties containing maleimide termini linked by aliphatic chains such as BMH and BMOE (Pierce, products Nos. 22330 and 22323) can be used.

Peptidic linkers are the other class of multivalent complex linkers. These linkers are comprised of chains of amino acids, and function to produce simple linkers or multimerisation domains onto which the polypeptides of the present invention can be attached. The biotin/streptavidin system has previously been used to produce tetramers of TCRs and pMHC molecules (see WO 99/60119) for in-vitro binding studies. However, streptavidin is a microbially-derived polypeptide and as such not ideally suited to use in a therapeutic.

Multivalent complexes of the invention in which the polypeptides are linked by a peptidic linker derived from a human multimerisation domain provide one embodiment of the present aspect. There are a number of human proteins that contain a multimerisation domain that could be used in the production of multivalent high affinity ILT-like polypeptide complexes. For example, the tetramerisation domain of p53 has been utilised to produce tetramers of scFv antibody fragments which exhibited increased serum persistence and significantly reduced off-rate compared to the monomeric scFv fragment. (Willuda et al. (2001) *J. Biol. Chem.* 276 (17) 14385-14392) Haemoglobin also has a tetramerisation domain that could potentially be used for this kind of application.

In a specific embodiment the multivalent complexes of the invention may be dimers or tetramers. Examples 9 and 10 herein provide detailed methodologies for the production of dimeric and tetrameric PEG-linked high affinity ILT-like complexes of the invention respectively. Example 11 herein provides data on the ability of such multivalent complexes to inhibit cytotoxic T cell activation.

A multivalent complex of the invention comprising at least two polypeptides of the invention, wherein at least one of said polypeptide is associated with a therapeutic agent provides a further embodiment of this aspect.

A further aspect is provided by a polypeptide of the invention or multivalent complex thereof wherein said polypeptide or multivalent complex is soluble.

A further aspect is provided by an isolated cell or a particle presenting at least one polypeptide of the invention. As will be obvious to those skilled in the art such polypeptides require a means of attachment to the surface of the said cells or particles. There are a number of means of facilitating such attachment. For example, particularly in the case of cells, this means of attachment may conveniently be provided by producing "full-length" versions of the chosen polypeptides which incorporate at least the transmembrane domain of human ILT-2. The transmembrane domain of human ILT-2 is underlined in FIG. 1a (SEQ ID NO: 1). However, this is not the only means of attaching such polypeptides to the surface of cells. For example, fusions proteins comprising a polypeptide of the invention or fragments thereof linked to the transmembrane domains of other polypeptides may be produced. In the case of attaching the polypeptides of the invention to particles this can conveniently be achieved by contacting polypeptides of the invention which comprise a C-terminal tag, such as biotin, with particles coated with a binding moiety specific for said tag, such as streptavidin.

Diagnostic and Therapeutic Use

In one aspect the polypeptides of the invention or multivalent complexes thereof may be labelled with an imaging compound, for example a label that is suitable for diagnostic purposes. Such labelled polypeptides are useful in a method for detecting target pMHC molecules which method comprises contacting the pMHC with a polypeptide of the invention or a multivalent complex thereof bind to the pMHC; and detecting said binding. In tetrameric complexes formed for example, using biotinylated polypeptide molecules, fluorescent streptavidin can be used to provide a detectable label. Such a fluorescently-labelled tetramer is suitable for use in FACS analysis, for example to detect antigen presenting cells. Another manner in which the soluble peptides of the present invention may be detected is by the use of antibodies, in particular monoclonal antibodies.

ILT-specific antibodies have been described in the literature. For example, IGH/75 is an ILT-2 specific IgG that was produced at the Basel Institute for Immunology, Basel, Switzerland. (Riteau et al., (2001) *Int. Immunol.* 13 (2) 193).

In a further aspect a polypeptide of the present invention or a multivalent complex thereof may alternatively or additionally be associated with (e.g. covalently or otherwise linked to) a therapeutic agent.

In a specific embodiment of the invention the therapeutic agent is covalently linked to the C terminus of the polypeptide.

There are a number of therapeutic agents which could be associated with the polypeptides of the invention. For example, the therapeutic agent may be an immune effector molecule. A specific embodiment of this aspect is provided wherein the immune effector molecule is a cytokine. As is known to those skilled in the art there are a number of cytokines which generally act to "suppress" immune responses. Polypeptides of the invention associated with such immunosuppressive cytokines form preferred embodiments of the invention. Polypeptides of the invention associated with IL-4, IL-10 or IL-13 or a phenotypically silent variant or fragment of these cytokines provide specific embodiments of the present invention.

A multivalent complex of the invention may have enhanced binding capability for a given pMHC compared to a non-multimeric wild-type ILT or the corresponding high affinity ILT-like polypeptide of the invention. Thus, the multivalent complexes according to the invention are particularly useful for tracking or targeting cells presenting particular antigens in vitro or in vivo, and are also useful as intermediates for the production of further multivalent complexes having such uses.

Pharmaceutical compositions comprising a polypeptide of the invention, or a multivalent complex thereof, or a plurality of cells expressing such polypeptides, together with a pharmaceutically acceptable carrier therefore provide a further aspect of the invention. A related embodiment is provided by the therapeutic use of a polypeptide of the invention, or a multivalent complex thereof, or a plurality of cells expressing such polypeptides.

Pharmaceutical compositions comprising a polypeptide of the invention or a multivalent complex thereof associated with a therapeutic agent together with a pharmaceutically acceptable carrier therefore provide a further aspect of the invention. A related embodiment is provided by the therapeutic use of a polypeptide of the invention or a multivalent complex thereof associated with a therapeutic agent.

Another aspect of the invention is provided by the use of a polypeptide of the invention, or a multivalent complex thereof, or a plurality of cells or particles expressing such polypeptides, in the manufacture of a medicament for the treatment of autoimmune disease, said medicament being adapted for parenteral administration. Suitable parenteral routes of administration include subcutaneous, intradermal or intramuscular routes.

A further aspect of the inventions is provided by the use of a polypeptide of the invention or a multivalent complex thereof associated with a therapeutic agent, in the manufacture of a medicament for the treatment of autoimmune disease, said medicament being adapted for parenteral administration. Suitable parenteral routes of administration include subcutaneous, intradermal or intramuscular routes.

The invention also provides a method for delivering a therapeutic agent to a target cell, which method comprises contacting potential target cells with a polypeptide or multivalent complex in accordance with the invention under conditions to allow attachment of the polypeptide or multivalent complex to the target cell, said polypeptide or multivalent complex capable of binding to a given Class I pMHC molecule and having the therapeutic agent associated therewith.

A therapeutic agent could be delivered such that it would exercise its effect locally, not only on the cell it has directly bound. Thus, one particular strategy envisages "immunesuppressor" molecules linked to a polypeptide or multivalent complex according to the invention specific for tumour antigens.

Soluble polypeptides or multivalent complexes of the invention may be linked to an enzyme capable of converting a prodrug to a drug. This allows the prodrug to be converted to the drug only at the site where it is required (i.e. targeted by the said polypeptide or multivalent complex).

It is expected that the polypeptides and multivalent complexes disclosed herein may be used in methods for the diagnosis and treatment of autoimmune disease.

The invention also provides a method of treatment of autoimmune disease comprising administering to a subject suffering such autoimmune disease an effective amount of a polypeptide of the invention or multivalent complex thereof, or a plurality of cells or particles presenting at least one such polypeptide. In a related embodiment the invention provides for the use of a polypeptide of the invention or multivalent complex thereof, or a plurality of cells or particles presenting at least one such polypeptide, in the preparation of a composition for the treatment of autoimmune disease.

The invention also provides a method of treatment of autoimmune disease comprising administering to a subject suffering such autoimmune disease an effective amount of a polypeptide of the invention or a multivalent complex thereof associated with a therapeutic agent. In a related embodiment the invention provides for the use of a polypeptide of the invention or a multivalent complex thereof, associated with a therapeutic agent, in the preparation of a composition for the treatment of autoimmune disease.

Therapeutic or imaging polypeptides in accordance with the invention will usually be supplied as part of a sterile, pharmaceutical composition which will normally include a pharmaceutically acceptable carrier. This pharmaceutical composition may be in any suitable form, (depending upon the desired method of administering it to a patient). It may be provided in unit dosage form, will generally be provided in a sealed container and may be provided as part of a kit. Such a kit would normally (although not necessarily) include instructions for use. It may include a plurality of said unit dosage forms.

The pharmaceutical composition may be adapted for administration by any appropriate route, for example parenteral, transdermal or via inhalation, preferably a parenteral (including subcutaneous, intramuscular, or, most preferably intravenous) route. Such compositions may be prepared by any method known in the art of pharmacy, for example by mixing the active ingredient with the carrier(s) or excipient(s) under sterile conditions.

Dosages of the substances of the present invention can vary between wide limits, depending upon the disease or disorder to be treated, the age and condition of the individual to be treated, etc. and a physician will ultimately determine appropriate dosages to be used.

Additional Aspects

A polypeptide or multivalent complex of the present invention may be provided in substantially pure form, or as a purified or isolated preparation. For example, it may be provided in a form which is substantially free of other proteins.

Further embodiments are provided by an isolated nucleic acid encoding the polypeptides of the invention, vectors incorporating said nucleic acid and cells containing said vectors. The nucleic acid encoding the polypeptide of the invention may be one which has been adapted for high level expression in a host cell. There are a number of companies which offer such nucleic acid optimisation as a service, for example GeneArt, Germany.

The invention also provides a method of identifying a high affinity variant of a given ILT molecule having the property of binding to a given Class I pMHC CHARACTERISED IN THAT said polypeptide has a $K_D$ for the said given Class I pMHC of less than or equal to 1 µM and/or has an off-rate ($k_{off}$) for the said given Class I pMHC molecule of 2 $S^{-1}$ or slower AND said polypeptide has at least a 45% identity and/or 55% similarity to SEQ ID NO: 7 AND said polypeptide inhibits CD8 binding to the given pMHC to a greater extent than the polypeptide SEQ ID NO: 3 said method comprising:

(a) The production of a library of ILT molecules comprising in one or more mutations in the amino acid sequence compared to the corresponding Wild-Type ILT molecule; and
(b) Contacting said mutated ILT molecules with the target Class I pMHC under conditions suitable to allow the binding of the mutated ILT molecule to the target Class I pMHC; and
(c) Measuring the $K_D$ and/or $k_{off}$ of the interaction; and
(d) Selecting the polypeptide(s) with the desired binding characteristics.

Phage display of ILT polypeptides and/or ILT-like polypeptides provides one method of generating a library of polypeptides suitable for use in the above method.

A final aspect is provided by a method of producing a polypeptide of the invention comprising:

(i) transforming a host cell with a vector incorporating nucleic acid encoding a polypeptide of the invention; and
(ii) culturing the transformed cells under conditions suitable for the expression of a polypeptide of the invention; and
(iii) recovering the expressed polypeptide.

Specific embodiments of the present aspect are provided wherein the host cells are *E. coli* cells or yeast cells, for example *Pichia pastoris* cells. Examples 1 to 3, and 7 to 8 herein provide detailed methodologies for the production of polypeptides of the invention in *E. coli* and *Pichia Pastoris* cells respectively.

Preferred features of each aspect of the invention are as for each of the other aspects *mutatis mutandis*. The prior art documents mentioned herein are incorporated to the fullest extent permitted by law.

EXAMPLES

The invention is further described in the following examples, which do not limit the scope of the invention in any way.

Reference is made in the following to the accompanying drawings in which:

FIG. 1*a* provides the full amino acid sequence of a wild type human ILT-2. (SEQ ID No: 1) The highlighted amino acids show residues of this polypeptide which differ from the corresponding residues of isoform 1 of Wild-type human ILT-2. The amino acids of the transmembrane domain are underlined.

FIG. 1*b* provides the full DNA sequence of a wild type human ILT-2 (SEQ ID No: 2) which encodes the amino acid sequence of FIG. 1*a*. The DNA sequence corresponds to that given NCIMB Nucleotide accession NO: NM_006669.

FIGS. 2*a* and 2*b* respectively provide the amino acid and DNA sequence of a soluble two domain form of the wild-type ILT-2 sequences provided in FIGS. 1*a* and 1*b*. These truncated sequences contain/encode for only extracellular domains D1 and D2 of ILT-2. (SEQ ID No: 3 and SEQ ID NO: 4 respectively)

FIG. 3 provides the full DNA sequence inserted into the pGMT7-based vector in order to express the soluble two domain form of the wild-type ILT-2 polypeptide of FIG. 2*a*. The HindIII and NdeI restriction enzyme recognition sequences are underlined.

FIGS. 4*a* to 4*d* (SEQ ID Nos 6-9) provide the amino acid sequences of soluble two domain high affinity ILT-like polypeptides. The residues which have been mutated relative to those of FIG. 2*a* are highlighted FIGS. 5*a* to 5*d* (SEQ ID Nos 10-13) provide the DNA sequences inserted a pGMT7-derived vector in order to express the soluble two domain high affinity ILT-like polypeptides shown in FIGS. 4*a* to 4*d* respectively. The codons which have been mutated relative to those of FIG. 3 are highlighted, and the HindIII and NdeI restriction enzyme recognition sequences are underlined.

FIG. 6 provides the DNA sequence of a pGMT7-derived vector into which the DNA sequences of FIGS. 5*a* to 5*d* can be inserted.

FIG. 7 provides the plasmid map of a pGMT7-derived vector into which the DNA sequences of FIGS. 5*a* to 5*d* can be inserted.

FIG. 8*a* provides the amino acid sequence of a soluble two domain (c20) high affinity ILT-like polypeptide.

FIG. 8*b* provides the amino acid sequence of a soluble two domain (c50) high affinity ILT-like polypeptide.

FIG. 8*c* provides the amino acid sequence of a soluble two domain (c50) high affinity ILT-like polypeptide which has a cysteine residue added to the C-terminus thereof.

FIG. 9*a* provides the DNA sequence encoding a soluble two domain (c20) high affinity ILT-like polypeptide which has a cysteine encoding codon added to the 5' end thereof. This DNA sequence has been optimised for expression in *Pichia Pastoris* and incorporates SnaBI and NotI restriction enzyme recognition sites which are underlined.

FIG. 9*b* provides the amino acid sequence of soluble two domain (c20) high affinity ILT-like polypeptide which has a cysteine residue added to the C-terminus thereof encoded by the DNA sequence of FIG. 9*a*.

Figure 10:
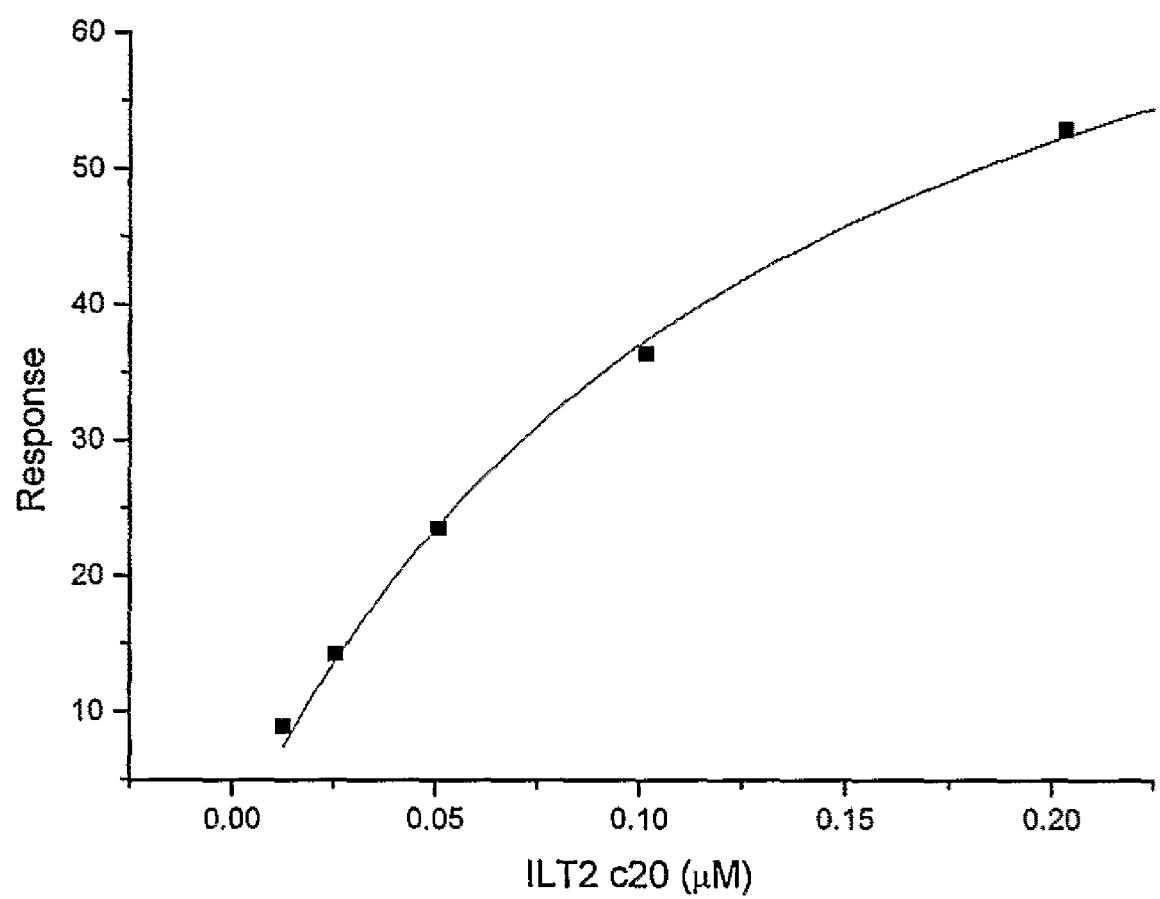

FIG. 10 provides the Biacore response curve generated for the interaction of a *Pichia Pastoris* expressed soluble two domain (c20) high affinity ILT-like polypeptide and Class I MHC.

Figure 11:
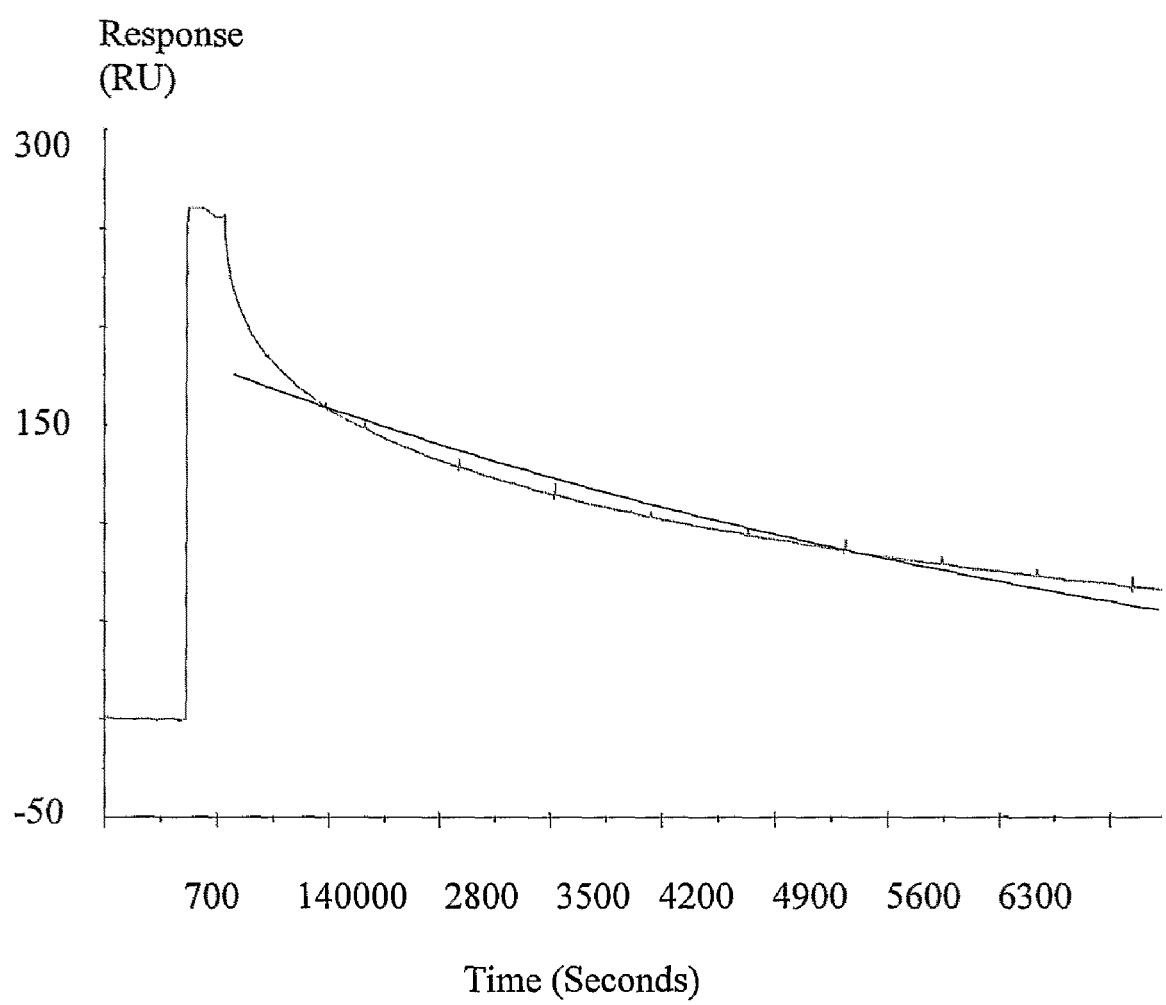

FIG. 11 provides the Biacore response curve generated for the interaction of a soluble two domain (c20) high affinity ILT-like polypeptide dimer and Tax-HLA-A*0201.

Figure 12:
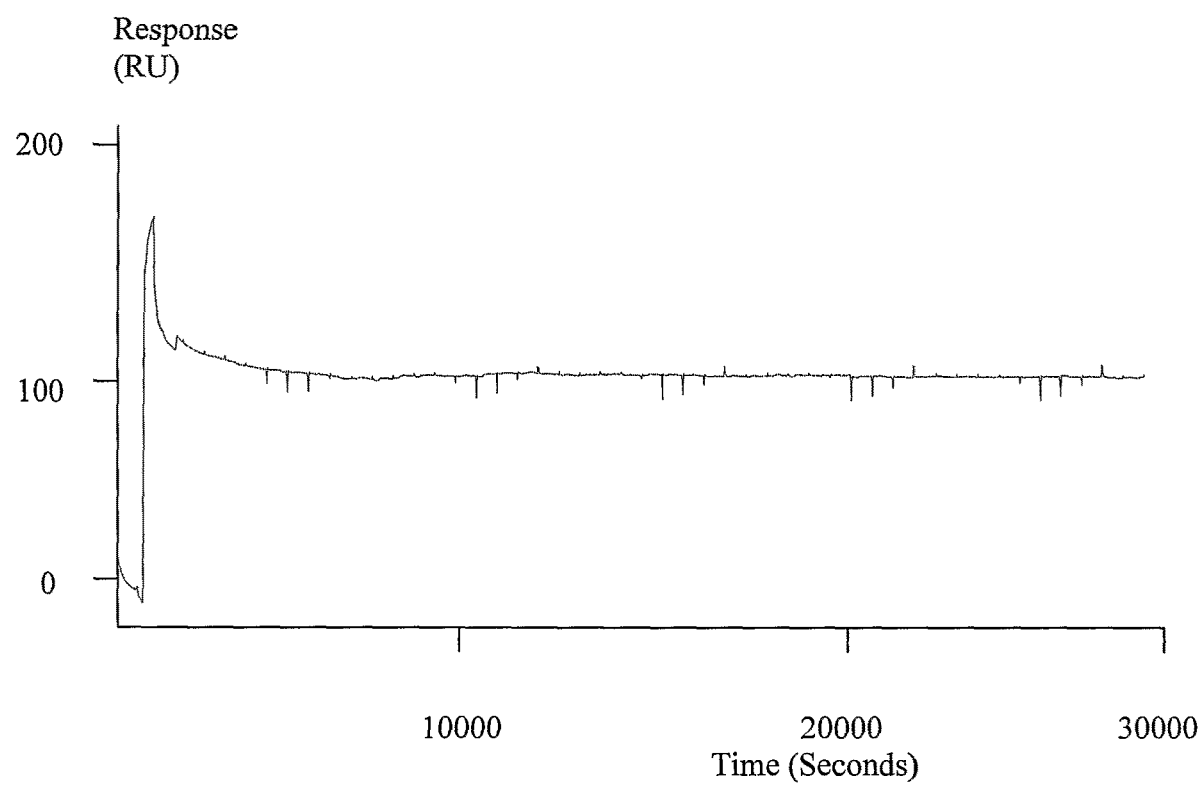

FIG. 12 provides the Biacore response curve generated for the interaction of soluble two domain (c20) high affinity ILT-like polypeptide tetramer and Tax-HLA-A*0201.

FIGS. 13*a*-13*bh* provide the amino acid sequences of further two domain high affinity ILT-like polypeptides.

Figure 14:
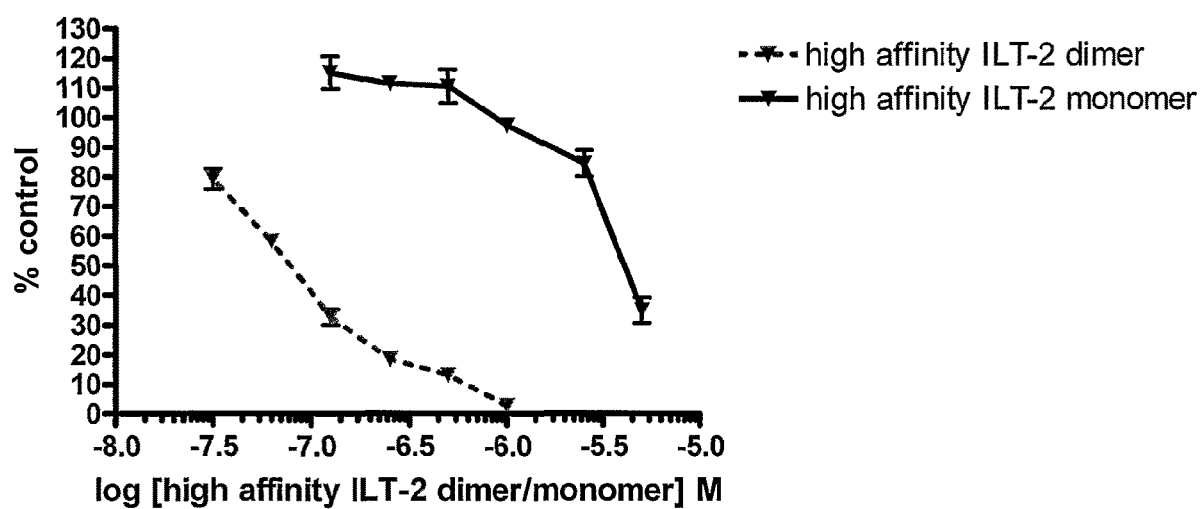

FIG. 14 provides ELISPOT data showing inhibition of CTL activation by high affinity (c50) ILT-like monomers and dimers.

Figure 15:
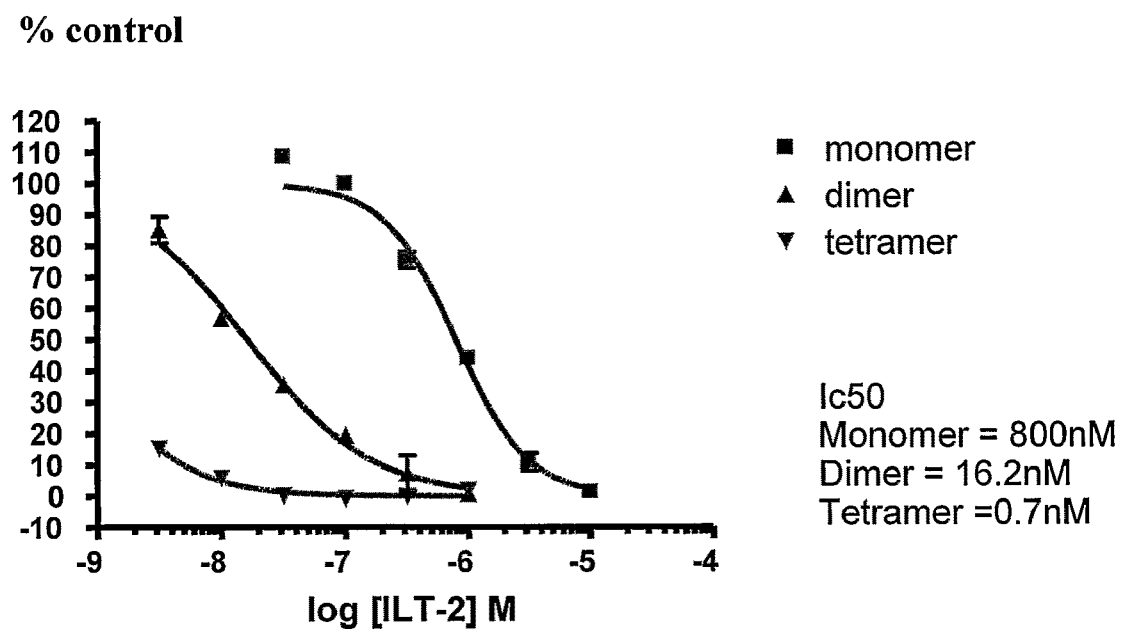

FIG. 15 provides ELISPOT data showing inhibition of CTL activation by high affinity (c50) ILT-like monomers, dimers and tetramers.

EXAMPLE 1

Production of a Soluble Wild-Type ILT-2 Molecule Comprising Domains 1 and 2

FIG. 3 (SEQ ID NO: 5) provides the DNA sequence used to express a soluble w

D1 and D2. This DNA sequence was synthesised de-novo by a contract research companies, GeneArt (Germany). Restriction enzyme recognition sites (NdeI and HindIII) have been introduced into this DNA sequence in order to facilitate ligation of the DNA sequence into a pGMT7-based expression plasmid, which contains the T7 promoter for high level expression in *E. coli* strain BL21-DE3(pLysS) (Pan et al., *Biotechniques* (2000) 29 (6): 1234-8)

This DNA sequence is ligated into a pGMT7 vector cut with NdeI and HindIII. (See FIG. 6 for the DNA sequence of this vector and FIG. 7 for the plasmid map of this vector). Restriction Enzyme Recognition Sites as Introduced into DNA Encoding the Soluble Wild-Type ILT-2 Polypeptide

```
NdeI-      CATATG
HindIII-   AAGCTT
```

Ligation

The cut ILT-2 DNA and cut vector are ligated using a rapid DNA ligation kit (Roche) following the manufacturers instructions.

Ligated plasmids are transformed into competent *E. coli* strain XL1-blue cells and plated out on LB/agar plates containing 100 mg/ml ampicillin. Following incubation overnight at 37° C., single colonies are picked and grown in 10 ml LB containing 100 mg/ml ampicillin overnight at 37° C. with shaking. Cloned plasmids are purified using a Miniprep kit (Qiagen) and the insert is sequenced using an automated DNA sequencer (Lark Technologies).

FIG. 2a shows the amino acid sequence of the soluble wild-type ILT-2 polypeptide produced from the DNA sequence of FIG. 2b.

EXAMPLE 2

Production of High Affinity Variants of the Soluble Wild-Type ILT-2 Polypeptide

The soluble wild-type ILT-2 polypeptide produced as described in Example 1 can be used a template from which to produce the polypeptides of the invention which have an increased affinity and/or slower off-rate for class I pMHC molecules.

As is known to those skilled in the art the necessary codon changes required to produce these mutated chains can be introduced into the DNA encoding the soluble wild-type ILT-2 polypeptide by site-directed mutagenesis. (QuickChange™ Site-Directed Mutagenesis Kit from Stratagene)

Briefly, this is achieved by using primers that incorporate the desired codon change(s) and the plasmids containing the DNA encoding the soluble wild-type ILT-2 polypeptide as a template for the mutagenesis:

Mutagenesis was carried out using the following conditions: 50 ng plasmid template, 1 µl of 10 mM dNTP, 5 µl of 10×Pfu DNA polymerase buffer as supplied by the manufacturer, 25 pmol of fwd primer, 25 pmol of rev primer, 1 µl pfu DNA polymerase in total volume 50 µl. After an initial denaturation step of 2 mins at 95 C, the reaction was subjected to 25 cycles of denaturation (95 C, 10 secs), annealing (55 C 10 secs), and elongation (72 C, 8 mins). The resulting product was digested with DpnI restriction enzyme to remove the template plasmid and transformed into *E. coli* strain XL1-blue. Mutagenesis was verified by sequencing.

The amino sequences of the mutated ILT-like polypeptides which demonstrate high affinity for the YLSGANLNL (SEQ ID NO: 15)-HLA-A*0201 complex are listed in FIGS. 4a to 4d (SEQ ID Nos: 6 to 9), and FIGS. 13a to 13bh (SEQ ID NOs: 21 to 80). As is known to those skilled in the art the necessary codon changes required to produce these mutated polypeptides can be introduced into the DNA encoding the wild-type soluble ILT-2 polypeptide by site-directed mutagenesis. (QuickChange™ Site-Directed Mutagenesis Kit from Stratagene)

EXAMPLE 3

Expression, Refolding and Purification of Soluble Polypeptides

The expression plasmid containing the ILT polypeptides as prepared in Examples 1 or 2 are transformed separately into *E. coli* strain rosetta DE3pLysS, and single ampicillin/chloramphenicol-resistant colonies are grown at 37° C. in TYP (ampicillin 100 µg/ml, chloramphenicol 15 µg/ml) medium for 7 hours before inducing protein expression with 0.5 mM IPTG. Cells are harvested 15 hours post-induction by centrifugation for 30 minutes at 4000 rpm in a Beckman J-6B. Cell pellets are re-suspended in a buffer, re-suspended cells are sonicated in 1 minute bursts for a total of around 10 minutes in a Milsonix XL2020 sonicator using a standard 12 mm diameter probe. Inclusion body pellets are recovered by centrifugation for 10 minutes at 400 rpm in a Beckman J2-21 centrifuge. Three detergent washes are then carried out to remove cell debris and membrane components. Each time the inclusion body pellet is homogenised in a Triton buffer (50 mM Tris-HCl, 0.5% Triton-X100, 200 mM NaCl, 10 mM NaEDTA, 0.1% (w/v) NaAzide, 2 mM DTT, pH 8.0) before being pelleted by centrifugation for 15 minutes at 4000 rpm in a Beckman J2-21. Detergent and salt is then removed by a similar wash in the following buffer: 50 mM Tris-HCl, 1 mM NaEDTA, 0.1% (w/v) NaAzide, 2 mM DTT, pH 8.0. Finally, the inclusion bodies are divided into 60 mg aliquots and frozen at −70° C. Inclusion body protein yield is quantitated by solubilising with 6M guanidine-HCl and measurement using a UV spectrometer.

Approximately 60 mg of ILT polypeptide solubilised inclusion bodies are thawed from frozen stocks and diluted into 15 ml of a guanidine solution (6 M Guanidine-hydrochloride, 10 mM Sodium Acetate, 10 mM EDTA), to ensure complete chain de-naturation. The guanidine solution containing fully reduced and denatured ILT polypeptide is then injected into 1 litre of the following refolding buffer: 100 mM Tris pH 8.5, 400 mM L-Arginine, 2 mM EDTA, 5 mM reduced Cystaeimine, 0.5 mM 2-mercaptoethylamine, 5M urea. The redox couple (2-mercaptoethylamine and cystamine (to final concentrations of 6.6 mM and 3.7 mM, respectively) are added approximately 5 minutes before addition of the denatured ILT polypeptide. The solution is left for 30 minutes. The refolded ILT polypeptide was dialysed in Spectrapor 1 membrane (Spectrum; Product No. 132670) against 10 L 10 mM Tris pH 8.1 at 5° C.±3° C. for 18-20 hours. After this time, the dialysis buffer is changed to fresh 10 mM Tris pH 8.1 (10 L) and dialysis is continued at 5° C.±3° C. for another 20-22 hours.

Soluble ILT polypeptide is separated from degradation products and impurities by loading the dialysed refold onto a POROS 50HQ anion exchange column and eluting bound protein with a gradient of 0-500 mM NaCl over 50 column volumes using an Akta purifier (Pharmacia). Peak fractions are stored at 4° C. and analysed by Coomassie-stained SDS-PAGE before being pooled and concentrated. Finally, the soluble ILT polypeptide is purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 27 kDa is pooled and concentrated prior to characterisation by Biacore surface plasmon resonance analysis.

EXAMPLE 4

Biacore Surface Plasmon Resonance Characterisation of the Binding of Soluble ILT Molecules to PMHC Molecules A surface plasmon resonance biosensor (Biacore 3000™) was used to analyse the binding of soluble ILT molecules to class I pMHC. This was facilitated by producing soluble biotinylated pMHC (described below) which were immobilised to a streptavidin-coated binding surface in a semi-oriented fashion, allowing efficient testing of the binding of a soluble ILT molecule to up to four different pMHC (immobilised on separate flow cells) simultaneously. Injection of the pMHC allows the precise level of immobilised class I molecules to be manipulated easily.

Soluble biotinylated class I HLA-A*0201 loaded with a CEA-derived YLSGANLNL (SEQ ID NO: 15) peptide were refolded in vitro from bacterially-expressed inclusion bodies containing the constituent subunit proteins and synthetic peptide, followed by purification and in vitro enzymatic biotinylation (O'Callaghan et al. (1999) *Anal. Biochem.* 266: 9-15). MHC-heavy chain was expressed with a C-terminal biotinylation tag which replaces the transmembrane and cytoplasmic domains of the protein in an appropriate construct. Inclusion body expression levels of 75 mg/litre bacterial culture were obtained. The MHC light-chain or β2-microglobulin was also expressed as inclusion bodies in *E. coli* from an appropriate construct, at a level of 500 mg/litre bacterial culture.

The *E. coli* cells were lysed and inclusion bodies are purified to approximately 80% purity. Protein from inclusion bodies was denatured in 6 M guanidine-HCl, 50 mM Tris pH 8.1, 100 mM NaCl, 10 mM DTT, 10 mM EDTA, and was refolded at a concentration of 30 mg/litre heavy chain, 30 mg/litre β2 m into 0.4 M L-Arginine-HCl, 100 mM Tris pH 8.1, 3.7 mM cystamine, 6.6 mM β-cysteamine, 4 mg/ml of the peptide required to be loaded by the MHC, by addition of a single pulse of denatured protein into refold buffer at <5° C. Refolding was allowed to reach completion at 4° C. for at least 1 hour.

Buffer was exchanged by dialysis in 10 volumes of 10 mM Tris pH 8.1. Two changes of buffer were necessary to reduce the ionic strength of the solution sufficiently. The protein solution was then filtered through a 1.5 μm cellulose acetate filter and loaded onto a POROS 50HQ anion exchange column (8 ml bed volume). Protein was eluted with a linear 0-500 mM NaCl gradient. The soluble biotinylated HLA-A2-peptide complex eluted at approximately 250 mM NaCl, and peak fractions were collected, a cocktail of protease inhibitors (Calbiochem) was added and the fractions were chilled on ice.

Biotinylation tagged pMHC were buffer exchanged into 10 mM Tris pH 8.1, 5 mM NaCl using a Pharmacia fast desalting column equilibrated in the same buffer. Immediately upon elution, the protein-containing fractions were chilled on ice and protease inhibitor cocktail (Calbiochem) was added. Biotinylation reagents were then added: 1 mM biotin, 5 mM ATP (buffered to pH 8), 7.5 mM MgCl$_2$, and 5 μg/ml BirA enzyme (purified according to O'Callaghan et al. (1999) *Anal. Biochem.* 266: 9-15). The mixture was then allowed to incubate at room temperature overnight.

Biotinylated pMHC were purified using gel filtration chromatography. A Pharmacia Superdex 75 HR 10/30 column was pre-equilibrated with filtered PBS and 1 ml of the biotinylation reaction mixture was loaded and the column was developed with PBS at 0.5 ml/min. Biotinylated pMHC eluted as a single peak at approximately 15 ml. Fractions containing protein were pooled, chilled on ice, and protease inhibitor cocktail was added. Protein concentration was determined using a Coomassie-binding assay (PerBio) and aliquots of biotinylated pMHC were stored frozen at −20° C. Streptavidin was immobilised by standard amine coupling methods.

Such immobilised pMHC are capable of binding soluble T-cell receptors and the co-receptor CD8αα, as well as ILT molecules, and these interactions can be used to ensure that the immobilised pMHC are correctly refolded.

The interactions between a soluble ILT molecule and CEA-derived YLSGANLNL (SEQ ID NO: 15)-HLA-A*0201, the production of which is described above, were analysed on a Biacore 3000™ surface plasmon resonance (SPR) biosensor. SPR measures changes in refractive index expressed in response units (RU) near a sensor surface within a small flow cell, a principle that can be used to detect receptor ligand interactions and to analyse their affinity and kinetic parameters. The probe flow cells were prepared by immobilising the pMHC complexes in flow cells via biotin-tag binding. The assay was then performed by passing soluble ILT over the surfaces of the different flow cells at a constant flow rate, measuring the SPR response in doing so.

To Measure Equilibrium Binding Constant

Serial dilutions of soluble ILT molecules were prepared and injected at constant flow rate of 5 μl min-1 over two different flow cells; one coated with ~500 RU of the specific -HLA-A*0201 complex, the second cell was left blank as a control. Response was normalised for each concentration using the measurement from the control cell. Normalised data response was plotted versus concentration of ILT sample and fitted to a hyperbola in order to calculate the equilibrium binding constant, $K_D$. (Price & Dwek, Principles and Problems in Physical Chemistry for Biochemists ($2^{nd}$ Edition) 1979, Clarendon Press, Oxford).

To Measure Kinetic Parameters

For high affinity soluble ILTs $K_D$ was determined by experimentally measuring the dissociation rate constant, kd, and the association rate constant, ka. The equilibrium constant $K_D$ was calculated as kd/ka.

High affinity ILT-like molecules were injected over two different cells one coated with ~300 RU of CEA-derived YLSGANLNL (SEQ ID NO: 15)-HLA-A*0201 complex, the second was left blank as a control Flow rate was set at 50 μl/min. Typically 250 μl of ILT polypeptide at ~3 μM was injected. Buffer was then flowed over until the response had returned to baseline. Kinetic parameters were calculated using Biaevaluation software. The dissociation phase was also fitted to a single exponential decay equation enabling calculation of half-life.

Results

The interaction between a soluble variant of wild-type ILT-2 and the CEA-derived YLSGANLNL-HLA-A*0201 complex was analysed using the above methods and demonstrated a $K_D$ of approximately 6 μM. The ILT-like molecules having the amino acid sequences provided in FIGS. 4a to 4d (SEQ ID Nos: 6 to 9), and FIGS. 13a to 13bh (SEQ ID NOs: 21 to 80) have a $K_D$ of less than or equal to 1 μM and/of 2 $S^{-1}$ or slower.

EXAMPLE 5

Biacore Surface Plasmon Resonance Analysis of Soluble ILT-Mediated Inhibition of the PMHC/CD8 Interaction A surface plasmon resonance biosensor (Biacore 3000™) is used to analyse soluble ILT-mediated inhibition of the pMHC/CD8 interaction. This is facilitated by producing soluble pMHC complexes (described below) and biotinylated soluble CD8αα molecules (also described below). The biotinylated soluble CD8αα molecules are immobilised to a streptavidin-coated binding surface "Biacore chip" in a semi-oriented fashion, allowing efficient testing of the binding of soluble pMHC complexes to the immobilised soluble CD8αα. Injection of the biotinylated soluble CD8ααmolecules allows the precise level of immobilised CD8 molecules to be manipulated easily.

Soluble HLA-A*0201 pMHC loaded with a CEA-derived YLSGANLNL (SEQ ID NO: 15) peptide are produced using the methods substantially as described in (Garboczi et. al., (1992) *PNAS USA* 89 3429-3433). The soluble pMHC molecules are refolded in vitro from *E. coli* expressed inclusion bodies containing the constituent subunit proteins and synthetic peptide and then purified. The MHC light-chain or β2-microglobulin is also expressed as inclusion bodies in *E. coli* from an appropriate construct, at a level of ~500 mg/litre bacterial culture.

*E. coli* cells are lysed and inclusion bodies are purified, and the over-expressed proteins are refolded and purified using the methods detailed in Example 4 except that the biotinylation steps are omitted.

Biotinylated soluble CD8 molecules are produced as described in Examples 1 and 6 of EP 1024822. Briefly, the soluble CD8α containing a C-terminal biotinylation tag is expressed as inclusion bodies in *E. coli* and then purified and refolded to produce CD8αα homodimers containing a tag sequence that can be enzymatically biotinylated. (Schatz, (1993) *Biotechnology N Y* 11: 1138-43). Biotinylation of the tagged CD8α molecules is then achieved using the BirA enzyme (O'Callaghan, et al. *Anal Biochem* 266(1): 9-15 (1999) Biotinylation reagents are: 1 mM biotin, 5 mM ATP (buffered to pH 8), 7.5 mM MgCl$_2$, and 5 μg/ml BirA enzyme (purified according to O'Callaghan et al. (1999) *Anal. Biochem.* 266: 9-15). The mixture is then allowed to incubate at room temperature overnight.

The biotinylated sCD8αα is immobilised on the surface of a Biacore streptavidin-coated chip producing a change in the refractive index of 1000 response units. Such immobilised CD8αα molecules are capable of binding soluble pMHC complexes which may be injected in the soluble phase.

The ability of the ILT molecules to inhibit the pMHC/CD8 interaction on a Biacore 3000™ surface plasmon resonance (SPR) biosensor is analysed as follows:

SPR measures changes in refractive index expressed in response units (RU) near a sensor surface within a small flow cell, a principle that can be used to detect receptor ligand interactions and to analyse their affinity and kinetic parameters. The chips are prepared by immobilising the soluble biotinylated CD8αα molecules to streptavidin coated chips as described above. Serial dilutions of wild-type ILT or high affinity ILT-like molecules are prepared and injected at constant flow rate of 5 μl min$^{-1}$ over a flow cell coated with 1000 RU of biotinylated CD8αα in the presence of a suitable concentration of soluble YLSGANLNL (SEQ ID NO: 15)-HLA-A*0201. The inhibition of the SPR responses for the CD8αα/pMHC interaction produce a dose response curve which is used to calculate an IC50 value for the polypeptide being assayed for this interaction.

EXAMPLE 6

Comparison of Polypeptide Sequence Identity and Similarity

The protein-protein comparison algorithm used to generate identity and similarity data for this application is available via the following website: http://fasta.bioch.virginia.edu/fasta_www/cgi/search_frm2.cgi The "FASTA: protein: protein DNA: DNA" programme available on this website was used to carry out these comparisons. The following (default) settings were used:

| | |
|---|---|
| Ktup: | Ktup = 2 |
| Scoring matrix: | Blosum 50 |
| Gap: | −10 |
| Ext: | −2 |

In order to run the required comparisons the soluble ILT-2 fragment amino acid sequence in single letter code as provided in FIG. 4b (SEQ ID NO: 7) is entered as the first (query) sequence and the amino acid sequence for comparison thereto is entered as the second (library) sequence. The algorithm can then be run and will provide percentage identity and similarity scores for the pair of sequences compared.

As will be obvious to those skilled in the art there are a number of sources of FASTA protein: protein comparisons which could be used for this analysis.

EXAMPLE 7

Production of *Pichia pastoris* Vectors for the Expression of Soluble High Affinity c20 ILT-Like Polypeptide FIG. 9a (SEQ ID NO: 19) provides the DNA sequence used to express a soluble c20 high affinity ILT-like polypeptide containing only domains D1 and D2 in *Pichia pastoris*. This DNA sequence which was optimised for *Pichia* expression was synthesised de-novo by a contract research companies, GeneArt (Germany). A cysteine-encoding codon was added to the 3' prime end of this DNA in order to provide a "tag" on the C-terminus of the expressed ILT-like polypeptide to facilitate multimerisation if required. Restriction enzyme recognition sites (SnaBI and NotI) were introduced into this DNA sequence in order to facilitate ligation of the DNA sequence into a pPIC9K expression plasmid. (Invitrogen)

Restriction Enzyme Recognition Sites as Introduced into DNA Encoding the Soluble High Affinity c20 ILT-Like Polypeptide:

| | |
|---|---|
| SnaBI- | tacgta |
| NotI- | gcggccgc |

Ligation

The high affinity ILT-like polypeptide encoding DNA sequence was ligated into a pPIC9K vector (Invitrogen) cut with SnaBI and NotI restriction enzymes using a rapid DNA ligation kit (Roche).

Plasmid Amplification

Ligated plasmids are transformed into competent XL1 blue, (Stratagene, Country) and plated out on LB/agar plates containing 100 mg/ml Kanamycin. Following incubation overnight at 37° C., single colonies are picked and grown in 100 ml LB containing 100 mg/ml Kanamycin overnight at 37° C. with shaking. Cloned plasmids are purified using a Midiprep kit (Qiagen) and the insert is sequenced using an automated DNA sequencer (Lark Technologies).

FIG. 9b (SEQ ID NO: 20) shows the amino acid sequence of the two domain high affinity ILT-like (c20) polypeptide encoded by the DNA sequence of FIG. 9a (SEQ ID NO: 19).

EXAMPLE 8

Expression and Purification of Soluble High Affinity ILT-Like Polypeptides in *Pichia pastoris*

The *Pichia pastoris* expression plasmid containing the affinity ILT-like polypeptide-encoding DNA as prepared in Example 7 were transformed into *Pichia pastoris* strain GS115 (Invitrogen, USA) as follows;

GS115 *Pichia pastoris* cells were made competent using a *Pichia* EasyComp Kit (Invitrogen). This kit uses PEG1000 to make the cells chemically competent.

The ILT-like polypeptide DNA containing vector was linearised using Sal I and transformed into the GS115 strain as described in the Invitrogen manual.

Transformants containing the high affinity ILT-like polypeptide encoding DNA were selected by growing cells on RDB agar plates (Invitrogen). The RDB agar lacks histidine, ensuring that only yeast cells which have been successfully transformed with the pPIC9K plasmid will grow. The pPIC9K plasmid imparts the ability of growing on histidine⁻ agar by providing a copy of the HIS4 gene which allows growth on His-media.

Single colonies were picked from the agar plate and grown at 30° C. in BMGY medium (Invitrogen) overnight before inducing protein expression. Protein expression was induced by spinning the cells (2000×g, 10 min) and resuspending in 200 ml BMMY induction media (Invitrogen). Cells are harvested 6 days post-induction by centrifugation for 30 minutes at 2000×g. The supernatant was concentrated down via tangential flow filtration (Sartorious 10 kDa cut off) to 10 ml and purified using SEC (S200HR GE Healthcare)

Peak fractions are stored at 4° C. and analysed by Coomassie-stained SDS-PAGE before being pooled and concentrated. Finally, the soluble high affinity ILT-like polypeptide is purified and characterised using a Superdex 200HR gel filtration column pre-equilibrated in HBS-EP buffer (10 mM HEPES pH 7.4, 150 mM NaCl, 3.5 mM EDTA, 0.05% nonidet p40). The peak eluting at a relative molecular weight of approximately 27 kDa is pooled and concentrated prior to characterisation by Biacore surface plasmon resonance analysis using the methods detailed in Example 4.

Results

*Pichia pastoris* expressed high affinity c20 ILT-like polypeptide had a $K_D$ of approximately 100-150 DM for Class I MHC as determined by the Biacore-based method of Example 4. (See FIG. 10 for the Biacore curve generated using the *Pichia* produced high affinity c20 ILT-like polypeptide. This compares to a $K_D$ of approximately 25-85 nM determined for the corresponding *E. coli*-produced high affinity c20 ILT-like polypeptide.

EXAMPLE 9

Dimerisation of ILT-Like Polypeptides Using a 3.4 KdMal-PEG-Mal Linker

Soluble c50 High affinity ILT-like polypeptides containing an additional cysteine residue at the C-terminus were prepared using the methods detailed in Examples 1 to 3. (See FIG. 8b (SEQ ID NO: 17) for amino acid sequence of this polypeptide) The ILT-like polypeptides were cross-linked using non-branched bifunctional maleimide-PEG (MAL-PEG-MAL, MW 3.4 KD, NOF Corporation, Japan). The maleimide groups on the termini of this linker confer free thiol binding specificity to the linker. Prior to cross-linking the ILT-like polypeptide was pre-treated with a reducing agent, 0.1 mM DTT (room temperature, overnight), in order to liberate the free cysteine on the soluble ILT-like polypeptide. This low concentration of reducing agent was used to selectively reduce the exposed C-terminal cysteine residue. The soluble ILT-like polypeptide was then re-purified by gel-filtration chromatography (Superdex 75) in PBS buffer. The ILT-like polypeptide was then re-concentrated using a 10 kDa cut-off centrifugal membrane concentrator (VivaScience, Satorius). Cross-linking was achieved by the stepwise addition of MAL-PEG-MAL (10 mM in DMF) at an approximately 2:1 (protein to cross-linker) molar ratio and subsequently incubating for 2 hours at room temperature. The product was then purified using Superdex 75 HR10/30 gel-filtration column pre-equilibrated in PBS. Three peaks were observed after cross-linking; of which one corresponded with the position of intact "monomeric" ILT-like polypeptides corresponded with higher molecular mass species. The material in the peaks was further analysed by SDS-PAGE.

Samples from the three peaks were pre-treated with standard SDS sample buffer (BioRad) without DTT (non-reducing) or with 15 mM DTT (reducing), and were run on a gradient 4-20% PAGE and stained with Coomassie blue stain. Under non-reducing conditions, the material in the three peaks appeared as the cross-linked (ILT--PEG-ILT) species, an intermediate species (ILT--PEG) and the non-modified ILT-2 respectively.

The ability of these soluble high affinity c50 ILT-like polypeptide dimers to bind Class I pMHC was confirmed using the Biacore-based method detailed in Example 4. The soluble high affinity c50 ILT-like dimers demonstrated a half-time for dissociation of approximately 30-86 minutes. By comparison, the Biacore determined half-time for disassociation of the corresponding soluble c50 ILT-2 monomeric polypeptide was approximately 6 secs. This clearly demonstrates the enhanced affinity obtained by dimerisation. FIG. 11 provides the Biacore curve for the interaction of the soluble high affinity c50 ILT-like polypeptide dimer and Tax-HLA-A*0201. This Biacore curve also has the regression line added which was used to calculate the half-time for dissociation for this particular run f86 minutes).

EXAMPLE 10

Tetramerisation of ILT-2Polypeptides

Soluble high affinity c50 ILT-like polypeptides containing an additional cysteine residue at the C-terminus were tetramerised using a tetrameric maleimide-PEG (4arm MAL-PEG, MW 20 KD, Shearwater Corporation). The maleimide groups on the termini of this linker confer free thiol binding specificity to the linker. Prior to cross-linking the soluble high affinity c50 ILT-like polypeptides were pre-treated with a reducing agent, 0.1 mM DTT (room temperature, overnight), in order to liberate the free cysteine on the soluble ILT-2 polypeptides. This low concentration of reducing agent was used to selectively reduce the exposed C-terminal cysteine residue. The soluble high affinity c50 ILT-like polypeptides were then re-purified by gel-filtration chromatography (Superdex 75) in PBS buffer. The soluble high affinity c50 ILT-like polypeptides were then re-concentrated using a 10 kDa cut-off centrifugal membrane concentrator (VivaScience, Satorius). Tetramerisaton was achieved by the stepwise addition of the 4arm MAL-PEG (10 mM in DMF) at an approximately 4:1 (protein to cross-linker) molar ratio and subsequent incubation for 2 hours at room temperature. The product was then purified using Superdex 75 HR10/30 gel-filtration column pre-equilibrated in PBS. The eluted fractions were further analysed by SDS-PAGE.

Samples from the fractions were pre-treated with standard SDS sample buffer (BioRad) without DTT (non-reducing) or with 15 mM DTT (reducing), and were run on a gradient 4-20% PAGE and stained with Coomassie blue stain. The SDS PAGE gels demonstrated that the tetrameric soluble high affinity c50 ILT-like polypeptide species made up approximately 50% of the protein present.

The ability of these tetramers to bind Class I pMHC was confirmed using the Biacore-based method detailed in Example 4. The soluble c50 ILT-like tetramers bound so strongly to Tax-HLA*0201 that it was impossible to determine the apparent $K_D$ or half time for disassociation for the interaction. By comparison, the Biacore determined half time for disassociation for the interaction of the corresponding soluble c50 ILT-2 dimeric and monomeric polypeptides were 30-86 minutes and approximately 6 seconds respectively. This clearly demonstrates the enhanced affinity obtained by tetranierisation. FIG. 12 provides the Biacore curve for the interaction of the soluble high affinity c50 ILT-like polypeptide tetramer and Tax-HLA*A0201.

EXAMPLE 11

ELISPOT Assay for Assessing In-Vitro Inhibition of Cyto-Toxic T Cell (CTL) Activation by High Affinity c50 ILT-Like Monomers, Dimers and Tetramers The following method provides a means of assessing the ability of soluble high affinity c50 ILT-like polypeptide monomers and multivalent complexes to inhibit CD8 co-receptor mediated T cell activation.
Reagents:
Assay media: 10% FCS (heat-inactivated, Gibco, cat#10108-165), 88% RPMI 1640 (Gibco, cat#42401-018), 1% glutamine (Gibco, cat#25030-024) and 1% penicillin/streptomycin (Gibco, cat#15070-063).
Wash buffer: 0.01 M PBS/0.05% Tween 20 (1 sachet of Phosphate buffered saline with Tween 20, pH7.4 from Sigma, Cat. # P-3563 dissolved in 1 litre distilled water gives final composition 0.01 M PBS, 0.138 M NaCl, 0.0027 M KCl, 0.05% Tween 20).
PBS (Gibco, cat#10010-015).
Diaclone EliSpot kit (IDS) EliSpot kit contains all other reagents required i.e. capture and detection antibodies, skimmed milk powder, BSA, streptavidin-alkaline phosphatase, BCIP/NBT solution (Human IFN-γ PVDF Eli-spot 20×96 wells with plates (IDS cat# DC-856.051.020, DC-856.000.000.
The following method is based on the manufacturers instructions supplied with each kit but contains some alterations.

Method
100 µl capture antibody was diluted in 10 ml sterile PBS per plate. 100 µl diluted capture antibody was aliquoted into each well and left overnight at 4° C., or for 2 hr at room temperature. The plates were then washed three times with 450 µl wash buffer, Ultrawash 96-well plate washer, (Thermo Life Sciences) to remove excess capture antibody. 100 µl of 2% skimmed milk was then added to each well. (One vial of skimmed milk powder as supplied with the EliSpot kit was dissolved in 50 ml sterile PBS). The plates were then incubated at room temperature for two hours before washing washed a further three times with 450 µl wash buffer, Ultrawash 96-well plate washer, (Thermo Life Sciences)

Mel 624 and MeI 526 target cells were detached from their tissue culture flasks using trypsin, washed once by centrifugation (280×g for 10 minutes) in assay media and resuspended at $1\times10^6$/ml in the same media. 50 ul of this suspension was then added to the assay plate to give a total target cell number of 50,000 cells/well.

A MART-1 specific T cell clone (KA/C5) (effector cell line) was harvested by centrifugation (280×g for 10 min) and resuspended at $1\times10^4$/ml in assay media to give 500 cells/well when 50 µl was added to the assay plate.

Soluble high affinity c50 ILT-like polypeptide monomer, dimer and tetramer were diluted in assay media at a 3× concentration to give a 1× final when 50 ul was added to the plate in a final volume of 150 µl. The concentration range of ILT-2 monomer tested was 10 µM-0.03 µM. The concentration range of ILT-2 dimer and tetramer tested was 1 µM-0.003 µM.

Wells containing the following were then prepared, (the final reaction volume in each well was 100 µl):
Test Samples (Added in Order)
50 µl MeI 624 or MeI 526 target cells
50 ul of the desired concentration of ILT-like monomer, tetramer or dimer.
50 ul T cell clone effector cells.
Negative Controls
50 µl target cells
50 ul of the highest concentration of ILT-like monomer, dimer or tetramer
50 µl assay media
OR
50 µl effector cells
50 µl of the highest concentration of ILT-like monomer, dimer or tetramer
50 µl assay media
Positive Controls
50 µl MeI 624 or MeI 526 target cells
50 µl effector cells
50 µl assay media
OR
To Show CD8 Dependency
50 µl MeI 624 or MeI 526 target cells
50 µl effector cells
50 µl containing 100 µg/ml HB230 anti CD8 antibody The plates were then incubated overnight at 37° C./5% $CO_2$. The plates were then washed six times with wash buffer before tapping out excess buffer. 550 µl distilled water was then added to each vial of detection antibody supplied with the ELISPOT kit to prepare a diluted solution. 100 µl of the diluted detection antibody solution was then further diluted in 10 ml PBS/1% BSA per plate and 100 µl of the diluted detection antibody solution was aliquoted into each well. The plates were then incubated at room temperature for 90 minutes.

After this time the plates were washed three times with wash buffer (three times with 450 µl wash buffer, Ultrawash 96-well plate washer (Thermo Life Sciences) and tapped dry. 10 μl streptavidin-Alkaline phosphatase was then diluted with 10 ml with PBS/1% BSA per plate and 100 μl of the diluted streptavidin was added to each well and incubated at room temperature for 1 hr. The plates were then washed again three times with 450 μl wash buffer and tapped dry.

100 μl of the BCIP/NBT supplied solution was added to each well and the plates are covered in foil and left to develop for 5-15 min. The plates were checked regularly during this period for spot formation in order to decide when to terminate the reaction.

The plates were then washed thoroughly in tap water and shaken before being taken apart and left to dry on the bench.

Once dry the plates were read using an ELISPOT reader (Autoimmune Diagnotistika, Germany).

The number of spots that appeared in each well is proportional to the number of T cells activated. Therefore, any decrease in the number of spots in the wells containing the soluble high affinity c50 ILT-like polypeptide monomer, dimer or tetramer indicates inhibition of CD8 co-receptor-mediated CTL activation.

Results

As shown in FIG. 14 the high affinity c50 ILT-2 polypeptide is effective at inhibiting CTL activation in both monomeric and dimeric forms. The high affinity c50 ILT-like dimer is considerably more effective at inhibiting CTL activation than the corresponding monomer. The high affinity c50 ILT-like tetramer is more effective still. (See FIG. 15) The $IC_{50}$ values calculated from the data shown in FIG. 15 for the inhibition of CTLs by the monomeric, dimeric and tetrameric ILT-like polypeptides were 800 nM, 16.2 nM and 0.7 nM respectively.

SEQUENCE LISTING

<160> NUMBER OF SEQ ID NOS: 80

<210> SEQ ID NO 1
<211> LENGTH: 650
<212> TYPE: PRT
<213> ORGANISM: Homo sapiens

<400> SEQUENCE: 1

```
Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Gly Gln Glu Thr Gln Glu Tyr Arg Leu Tyr Arg Glu Lys
    50                  55                  60

Lys Thr Ala Pro Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

Ala Gln Pro Ser Pro Val Val Asn Ser Gly Gly Asn Val Thr Leu Gln
    130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255
```

```
Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540

Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ser Glu Ala
        595                 600                 605

Pro Gln Asp Val Thr Tyr Ala Gln Leu His Ser Leu Thr Leu Arg Arg
    610                 615                 620

Lys Ala Thr Glu Pro Pro Pro Ser Gln Glu Gly Pro Ser Pro Ala Val
625                 630                 635                 640

Pro Ser Ile Tyr Ala Thr Leu Ala Ile His
                645                 650

<210> SEQ ID NO 2
<211> LENGTH: 2984
<212> TYPE: DNA
<213> ORGANISM: Homo sapiens
```

```
<400> SEQUENCE: 2
gaggaggaac agaaaagaaa agaaaagaaa aagtgggaaa caaataatct aagaatgagg      60
agaaagcaag aagagtgacc cccttgtggg cactccattg gttttatggc gcctctactt     120
tctggagttt gtgtaaaaca aaatatattat ggtctttgtg cacatttaca tcaagctcag    180
cctgggcggc acagccagat gcgagatgcg tctctgctga tctgagtctg cctgcagcat    240
ggacctgggt cttccctgaa gcatctccag ggctggaggg acgactgcca tgcaccgagg    300
gctcatccat ccacagagca gggcagtggg aggagacgcc atgaccccca tcctcacggt    360
cctgatctgt ctcgggctga gtctgggccc ccggacccac gtgcaggcag ggcacctccc    420
caagcccacc ctctgggctg aaccaggctc tgtgatcacc caggggagtc ctgtgaccct    480
caggtgtcag gggggccagg agacccagga gtaccgtcta tatagagaaa agaaaacagc    540
accctggatt acacggatcc cacaggagct tgtgaagaag gccagttcc ccatcccatc     600 catcacctgg gaacatgcag ggcggtatcg ctgttactat ggtagcgaca ctgcaggccg    660
ctcagagagc agtgaccccc tggagctggt ggtgacagga gcctacatca acccaccct    720 ctcagcccag cccagccccg tggtgaactc aggaggaat gtaaccctcc agtgtgactc     780
acaggtggca tttgatggct tcattctgtg taaggaagga gaagatgaac acccacaatg    840
cctgaactcc cagcccatg cccgtgggtc gtcccgcgcc atcttctccg tgggccccgt     900
gagcccgagt cgcaggtggt ggtacaggtg ctatgcttat gactcgaact ctccctatga    960
gtggtctcta cccagtgatc tcctggagct cctggtccta ggtgtttcta agaagccatc    1020
actctcagtg cagccaggtc ctatcgtggc ccctgaggag accctgactc tgcagtgtgg    1080
ctctgatgct ggctacaaca gatttgttct gtataaggac ggggaacgtg acttccttca    1140
gctcgctggc gcacagcccc aggctgggct ctcccaggcc aacttcaccc tgggccctgt    1200
gagccgctcc tacggggggcc agtacagatg ctacggtgca cacaacctct cctccgagtg    1260
gtcggccccc agcgaccccc tggacatcct gatcgcagga cagttctatg acagagtctc    1320
cctctcggtg cagccgggcc ccacggtggc ctcaggagag aacgtgaccc tgctgtgtca    1380
gtcacaggga tggatgcaaa ctttccttct gaccaaggag ggggcagctg atgacccatg    1440
gcgtctaaga tcaacgtacc aatctcaaaa ataccaggct gaattcccca tgggtcctgt    1500
gacctcagcc catgcgggga cctacagatg ctacggctca cagagctcca accctacct     1560 gctgactcac cccagtgacc ccctggagct cgtggtctca ggaccgtctg ggggccccag    1620
ctccccgaca acaggcccca cctccacatc tggccctgag gaccagcccc tcaccccac     1680 cgggtcggat cccagagtg gtctgggaag gcacctgggg gttgtgatcg gcatcttggt    1740
ggccgtcatc ctactgctcc tcctcctcct cctcctcttc ctcatcctcc gacatcgacg    1800
tcagggcaaa cactggacat cgacccagag aaaggctgat ttccaacatc ctgcaggggc    1860
tgtggggcca gagcccacag acagaggcct gcagtgagg tccagcccag ctgccgatgc    1920
ccaggaagaa aacctctatg ctgccgtgaa gcacacacag cctgaggatg gggtggagat    1980
ggacactcgg agcccacacg atgaagaccc ccaggcagtg acgtatgccg aggtgaaaca    2040
ctccagacct aggagagaaa tggcctctcc tccttcccca ctgtctgggg aattcctgga    2100
cacaaaggac agacaggcgg aagaggacag gcagatggac actgaggctg ctgcatctga    2160 agcccccag gatgtgacct acgcccagct gcacagcttg acccttagac ggaaggcaac    2220
tgagcctcct ccatcccagg aagggccctc tccagctgtg cccagcatct acgccactct    2280
ggccatccac tagcccaggg ggggacgcag accccacact ccatggagtc tggaatgcat    2340
```

-continued

| | |
|---|---|
| gggagctgcc cccccagtgg acaccattgg accccaccca gcctggatct accccaggag | 2400 |
| actctgggaa cttttagggg tcactcaatt ctgcagtata ataactaat gtctctacaa | 2460 |
| ttttgaaata aagcaacaga cttctcaata atcaatgaag tagctgagaa aactaagtca | 2520 |
| gaaagtgcat taaactgaat cacaatgtaa atattacaca tcaagcgatg aaactggaaa | 2580 |
| actacaagcc acgaatgaat gaattaggaa agaaaaaaag taggaaatga atgatcttgg | 2640 |
| cttccctata agaaatttag ggcagggcac ggtggctcac gcctgtaatt ccagcacttt | 2700 |
| gggaggccga ggcgggcaga tcacgagttc aggagatcga gaccatcttg gccaacatgg | 2760 |
| tgaaaccctg tctctcctaa aaatacaaaa attagctgga tgtggtggca gtgcctgtaa | 2820 |
| tcccagctat ttgggaggct gaggcaggag aatcgcttga accagggagt cagaggtttc | 2880 |
| agtgagccaa gatcgcacca ctgctctcca gcctggcgac agagggagac tccatctcaa | 2940 |
| attaaaaaaa aaaaaaaaa agaaagaaaa aaaaaaaaaa aaaa | 2984 |

<210> SEQ ID NO 3
<211> LENGTH: 198
<212> TYPE: PRT
<213> ORGANISM: Homo sapiens

<400> SEQUENCE: 3

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ala Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 4
<211> LENGTH: 690
<212> TYPE: DNA
<213> ORGANISM: Homo sapiens

<400> SEQUENCE: 4

| | |
|---|---|
| atggggcacc tccccaagcc caccctctgg gctgaaccag gctctgtgat cacccagggg | 60 |
| agtcctgtga ccctcaggtg tcagggggc caggagaccc aggagtaccg tctatataga | 120 |

```
gaaaagaaaa cagcaccctg gattacacgg atcccacagg agcttgtgaa gaagggccag      180
ttccccatcc catccatcac ctgggaacat gcagggcggt atcgctgtta ctatggtagc      240
gacactgcag gccgctcaga gagcagtgac cccctggagc tggtggtgac aggagcctac      300
atcaaaccca ccctctcagc ccagcccagc ccgtggtga actcaggagg gaatgtaacc       360
ctccagtgtg actcacaggt ggcatttgat ggcttcattc tgtgtaagga aggagaagat      420
gaacacccac aatgcctgaa ctcccagccc catgcccgtg gtcgtcccg cgccatcttc       480 tccgtgggcc ccgtgagccc gagtcgcagg tggtggtaca ggtgctatgc ttatgactcg      540 aactctcccct atgagtggtc tctacccagt gatctcctgg agctcctggt cctagcggcc     600
gcaggtggcg gtactagtac tgttgaaagt tgtttagcaa accccatac agaaaattca       660 tttactaacg tctggaaaga cgacaaaact                                      690

<210> SEQ ID NO 5
<211> LENGTH: 615
<212> TYPE: DNA
<213> ORGANISM: Artificial Sequence
<220> FEATURE:
<223> OTHER INFORMATION: DNA encoding two domain truncation of ILT-2
      and restricition enzyme recogniton sites as interted into pGMT7-
      based expression vector

<400> SEQUENCE: 5
tatacatatg ggtcatcttc caaaaccaac tctctgggct gaaccaggct ctgtgatcac       60
ccaggggagt cctgtgaccc tcaggtgtca gggggggccag gagacccagg agtaccgtct     120
atatagagaa aagaaaacag caccctggat tacacggatc ccacaggagc ttgtgaagaa     180
gggccagttc cccatcccat ccatcacctg gaacatgca gggcggtatc gctgttacta       240
tggtagcgac actgcaggcc gctcagagag cagtgacccc ctggagctgg tggtgacagg      300
agcctacatc aaacccaccc tctcagccca gcccagcccc gtggtgaact caggagggaa      360
tgtaaccctc cagtgtgact cacaggtggc atttgatggc ttcattctgt gtaaggaagg      420
agaagatgaa cacccacaat gcctgaactc ccagccccat gcccgtgggt cgtcccgcgc      480
catcttctcc gtgggccccg tgagcccgag ccgcaggtgg tggtacaggt gctatgctta      540
tgactcgaac tctccctatg agtggtctct acccagtgat ctcctggagc tcctggtcct      600
ataagcttga attcc                                                      615

<210> SEQ ID NO 6
<211> LENGTH: 198
<212> TYPE: PRT
<213> ORGANISM: Artificial Sequence
<220> FEATURE:
<223> OTHER INFORMATION: Mutated two-domain ILT-2

<400> SEQUENCE: 6

Met Gly His Leu Pro Lys Pro Thr Leu Trp Ala Glu Pro Gly Ser Val
1               5                   10                  15

Ile Thr Met Gly Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80
```

Asp Thr Ala Gly Arg Ser Glu Ser Ser Asp Pro Leu Glu Leu Val Val
            85                  90                  95

Thr Gly Ala Tyr Ile Lys Pro Thr Leu Ser Ala Gln Pro Ser Pro Val
        100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 7
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 7

Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
            85                  90                  95

Thr Gly Val Tyr Ile Lys Pro Thr Leu Ser Ala Gln Pro Ser Pro Val
        100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 8
<211> LENGTH: 198
<212> TYPE: PRT
<213> ORGANISM: Artificial Sequence
<220> FEATURE:
<223> OTHER INFORMATION: Mutated two-domain ILT-2 polypeptide

```
<400> SEQUENCE: 8

Met Gly His Leu Pro Lys Pro Thr Leu Trp Ala Glu Pro Gly Ser Val
1               5                   10                  15

Ile Thr Leu Met Gln Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ala Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 9
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 9

Met Gly His Leu Pro Lys Pro Thr Leu Trp Ala Glu Pro Gly Ser Val
1               5                   10                  15

Ile Thr Met Gln Arg Pro Val Thr Leu Arg Cys Gln Gly Gly Gln Glu
                20                  25                  30

Thr Gln Glu Tyr Arg Leu Tyr Arg Glu Arg Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ala Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
130                 135                 140

Cys Leu Ser Ser Gln Pro His Ala Arg Gly Ser Ser Arg Ala Ile Phe
```

```
                  145                 150                 155                 160
Ser Val Gly Pro Val Ser Pro Ser Arg Arg Trp Trp Tyr Arg Cys Tyr
                165                 170                 175
Ala Tyr Asp Ser Asn Ser Pro Tyr Glu Trp Ser Leu Pro Ser Asp Leu
            180                 185                 190
Leu Glu Leu Leu Val Leu
        195

<210> SEQ ID NO 10
<211> LENGTH: 615
<212> TYPE: DNA
<213> ORGANISM: Artificial Sequence
<220> FEATURE:
<223> OTHER INFORMATION: DNA encoding a mutated two-domain ILT-2
      polypeptide and restriction enzyme recognition sites

<400> SEQUENCE: 10
tatacatatg ggtcatcttc caaaaccaac tctctgggct gaaccaggct ctgtgatcac     60
catggggcag cctgtgaccc tcaggtgtca gggggggccag gagacccagg agtaccgtct   120
atatagagaa aagaaaacag caccctggat tacacggatc ccacaggagc ttgtgaagaa   180
gggccagttc cccatcccat ccatcacctg gaacatgca gggcggtatc gctgttacta   240
tggtagcgac actgcaggcc gctcagagag cagtgacccc ctggagctgg tggtgacagg   300
agcctacatc aaacccaccc tctcagccca gcccagcccc gtggtgaact caggagggaa   360 tgtaacccctc cagtgtgact cacaggtggc atttgatggc ttcattctgt gtaaggaagg   420
agaagatgaa cacccacaat gcctgaactc ccagcccccat gcccgtgggt cgtcccgcgc   480
catcttctcc gtgggccccg tgagcccgag tcgcaggtgg tggtacaggt gctatgctta   540
tgactcgaac tctccctatg agtggtctct acccagtgat ctcctggagc tcctggtcct   600
ataagcttga attcc                                                     615

<210> SEQ ID NO 11
<211> LENGTH: 615
<212> TYPE: DNA
<213> ORGANISM: Artificial Sequence
<220> FEATURE:
<223> OTHER INFORMATION: DNA encoding a mutated two-domain ILT-2
      polypeptide and restriction enzyme recognition sites

<400> SEQUENCE: 11
tatacatatg ggtcatcttc caaaaccaac tctctgggct gaaccaggct ctgtgatcac     60
catggatcaa cctgtgaccc tcaggtgtca gggggggccag gagacccagg agtaccgtct   120
atatagagaa aagaaaacag caccctggat tacacggatc ccacaggagc ttgtgaagaa   180
gggccagttc cccatcccat ccatcacctg gaacatgca gggcggtatc gctgttacta   240
tggtagcgac actgcaggcc gctcagagag cagtgacccc ctggagctgg tggtgacagg   300
agtctacatc aaacccaccc tctcagccca gcccagcccc gtggtgaact caggagggaa   360 tgtaacccctc cagtgtgact cacaggtggc atttgatggc ttcattctgt gtaaggaagg   420
agaagatgaa cacccacaat gcctgaactc ccagcccccat gcccgtgggt cgtcccgcgc   480
catcttctcc gtgggccccg tgagcccggg tcgcaggtgg tggtacaggt gctatgctta   540
tgactcgaac tctccctatg agtggtctct acccagtgat ctcctggagc tcctggtcct   600
ataagcttga attcc                                                     615

<210> SEQ ID NO 12
<211> LENGTH: 615
```

```
<212> TYPE: DNA
<213> ORGANISM: Artificial Sequence
<220> FEATURE:
<223> OTHER INFORMATION: DNA encoding a mutated two-domain ILT-2
      polypeptide and restriction enzyme recognition sites

<400> SEQUENCE: 12
tatacatatg ggtcatcttc caaaaccaac tctctgggct gaaccaggct ctgtgatcac    60
cctgatgcaa cctgtgaccc tcaggtgtca ggggggccag gagacccagg agtaccgtct   120
atatagagaa aagaaaacag caccctggat tacacggatc ccacaggagc ttgtgaagaa   180
gggccagttc cccatcccat ccatcacctg ggaacatgca gggcggtatc gctgttacta   240
tggtagcgac actgcaggcc gctcagagag cagtgacccc ctggagctgg tggtgacagg   300
agcctacatc aaacccaccc tctcagccca gccagccccc gtggtgaact caggagggaa   360
tgtaaccctc cagtgtgact cacaggtggc atttgatggc ttcattctgt gtaaggaagg   420
agaagatgaa cacccacaat gcctgaactc cagccccat gccgtgggt cgtcccgcgc    480 catcttctcc gtgggccccg tgagcccgag ccgcaggtgg tggtacaggt gctatgctta   540
tgactcgaac tctccctatg agtggtctct acccagtgat ctcctggagc tcctggtcct   600
ataagcttga attcc                                                    615

<210> SEQ ID NO 13
<211> LENGTH: 615
<212> TYPE: DNA
<213> ORGANISM: Artificial Sequence
<220> FEATURE:
<223> OTHER INFORMATION: DNA encoding a mutated two-domain ILT-2
      polypeptide and restriction enzyme recognition sites

<400> SEQUENCE: 13
tatacatatg ggtcatcttc caaaaccaac tctctgggct gaaccaggct ctgtgatcac    60
catgcagcgg cctgtgaccc tcaggtgtca ggggggccag gagacccagg agtaccgtct   120
atatagagaa aggaaaacag caccctggat tacacggatc ccacaggagc ttgtgaagaa   180
gggccagttc cccatcccat ccatcacctg ggaacatgca gggcggtatc gctgttacta   240
tggtagcgac actgcaggcc gctcagagag cagtgacccc ctggagctgg tggtgacagg   300
agcctacatc aaacccaccc tctcagccca gccagccccc gtggtgaact caggagggaa   360
tgtaaccctc cagtgtgact cacaggtggc atttgatggc ttcattctgt gtaaggaagg   420
agaagatgaa cacccacaat gcctgagctc cagccccat gccgtgggt cgtcccgcgc    480 catcttctcc gtgggccccg tgagcccgag tcgcaggtgg tggtacaggt gctatgctta   540
tgactcgaac tctccctatg agtggtctct acccagtgat ctcctggagc tcctggtcct   600
ataagcttga attcc                                                    615

<210> SEQ ID NO 14
<211> LENGTH: 3111
<212> TYPE: DNA
<213> ORGANISM: Artificial Sequence
<220> FEATURE:
<223> OTHER INFORMATION: DNA encoding pGMT7-based expression vector

<400> SEQUENCE: 14
gatctcgatc ccgcgaaatt aatacgactc actataggga ccacaacg gtttccctct      60 agaaataatt tgtttaact ttaagaagga gatatacata tgggatccat ggtaagcttg    120
aattccgatc cggctgctaa caaagcccga aggaagctg agttggctgc tgccaccgct   180
gagcaataac tagcataacc ccttggggcc tctaaacggg tcttgagggg ttttttgctg   240
```

```
aaaggaggaa ctatatccgg ataattcttg aagacgaaag ggcctcgtga tacgcctatt      300
tttataggtt aatgtcatga taataatggt ttcttagacg tcaggtggca cttttcgggg      360
aaatgtgcgc ggaacccta tttgtttatt tttctaaata cattcaaata tgtatccgct       420
catgagacaa taaccctgat aaatgcttca ataatatttt gttaaaattc gcgttaaatt      480
tttgttaaat cagctcattt tttaaccaat aggccgaaat cggcaaaatc ccttataaat      540
caaaagaata gaccgagata gggttgagtg ttgttccagt ttggaacaag agtccactat      600
taaagaacgt ggactccaac gtcaaagggc gaaaaaccgt ctatcagggc gatggcccac      660
tacgtgaacc atcaccctaa tcaagttttt tggggtcgag gtgccgtaaa gcactaaatc      720
ggaaccctaa agggagcccc cgatttagag cttgacgggg aaagccggcg aacgtggcga      780
gaaaggaagg gaagaaagcg aaaggagcgg gcgctagggc gctggcaagt gtagcggtca      840
cgctgcgcgt aaccaccaca cccgccgcgc ttaatgcgcc gctacagggc gcgtcaggtg      900
gcacttttcg gggaaatgtg cgcggaaccc ctatttgttt attttttctaa atacattcaa     960 atatgtatcc gctcatgaga caataacccct gataaatgct tcaataatat tgaaaaagga    1020
agagtatgag tattcaacat ttccgtgtcg cccttattcc cttttttgcg cattttgcc      1080 ttcctgtttt tgctcaccca gaaacgctgg tgaaagtaaa agatgctgaa gatcagttgg     1140
gtgcacgagt gggttacatc gaactggatc tcaacagcgg taagatcctt gagagttttc     1200
gccccgaaga acgttttcca atgatgagca cttttaaagt tctgctatgt ggcgcggtat     1260
tatcccgtgt tgacgccggg caagagcaac tcggtcgccg catacactat tctcagaatg     1320
acttggttga gtactcacca gtcacagaaa agcatcttac ggatggcatg acagtaagag    1380
aattatgcag tgctgccata accatgagtg ataacactgc ggccaactta cttctgacaa    1440
cgatcggagg accgaaggag ctaaccgctt ttttgcacaa catgggggat catgtaactc    1500
gccttgatcg ttgggaaccg gagctgaatg aagccatacc aaacgacgag cgtgacacca    1560
cgatgcctgc agcaatggca acaacgttgc gcaaactatt aactggcgaa ctacttactc    1620
tagcttcccg gcaacaatta atagactgga tggaggcgga taaagttgca ggaccacttc    1680
tgcgctcggc ccttccggct ggctggttta ttgctgataa atctggagcc ggtgagcgtg    1740
ggtctcgcgg tatcattgca gcactggggc cagatggtaa gccctcccgt atcgtagtta    1800
tctacacgac ggggagtcag gcaactatgg atgaacgaaa tagacagatc gctgagatag    1860
gtgcctcact gattaagcat tggtaactgt cagaccaagt ttactcatat atactttaga    1920
ttgatttaaa acttcatttt taatttaaaa ggatctaggt gaagatcctt tttgataatc    1980
tcatgaccaa aatcccttaa cgtgagtttt cgttccactg agcgtcagac cccgtagaaa    2040
agatcaaagg atcttcttga gatccttttt ttctgcgcgt aatctgctgc ttgcaaacaa    2100
aaaaaccacc gctaccagcg gtggtttgtt tgccggatca agagctacca actctttttc    2160
cgaaggtaac tggcttcagc agagcgcaga taccaaatac tgtccttcta gtgtagccgt    2220
agttaggcca ccacttcaag aactctgtag caccgcctac atacctcgct ctgctaatcc    2280
tgttaccagt ggctgctgcc agtggcgata agtcgtgtct taccgggttg gactcaagac    2340
gatagttacc ggataaggcg cagcggtcgg gctgaacggg gggttcgtgc acacagccca    2400
gcttggagcg aacgacctac accgaactga gatacctaca gcgtgagcta tgagaaagcg    2460
ccacgcttcc cgaagggaga aaggcggaca ggtatccggt aagcggcagg gtcggaacag    2520
gagagcgcac gagggagctt ccaggggaaa acgcctggta tctttatagt cctgtcgggt    2580
ttcgccacct ctgacttgag cgtcgatttt tgtgatgctc gtcaggggg cggagcctat     2640
```

```
ggaaaaacgc cagcaacgcg gccttttac ggttcctggc cttttgctgg ccttttgctc    2700
acatgttctt tcctgcgtta tccctgatt ctgtggataa ccgtattacc gcctttgagt    2760
gagctgatac cgctcgccgc agccgaacga ccgagcgcag cgagtcagtg agcgaggaag    2820
cggaagagcg cctgatgcgg tattttctcc ttacgcatct gtgcggtatt tcacaccgca    2880
atggtgcact ctcagtacaa tctgctctga tgccgcatag ttaagccagt atacactccg    2940
ctatcgctac gtgactgggt catggctgcg ccccgacacc cgccaacacc cgctgacgcg    3000
ccctgacggg cttgtctgct cccggcatcc gcttacagac aagctgtgac cgtctccggg    3060
agctgcatgt gtcagaggtt ttcaccgtca tcaccgaaac gcgcgaggca g            3111
```

<210> SEQ ID NO 15
<211> LENGTH: 9
<212> TYPE: PRT
<213> ORGANISM: Homo sapiens

<400> SEQUENCE: 15

Tyr Leu Ser Gly Ala Asn Leu Asn Leu
1               5

<210> SEQ ID NO 16
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 16

Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Ser
65                  70                  75                  80

Asp Thr Ser Gln Trp Ser Ala Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 17
<211> LENGTH: 198

```
<212> TYPE: PRT
<213> ORGANISM: Artificial Sequence
<220> FEATURE:
<223> OTHER INFORMATION: Mutated two-domain ILT-2 polypeptide

<400> SEQUENCE: 17

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
            180                 185                 190

Glu Leu Asp Val Asp Gly
        195

<210> SEQ ID NO 18
<211> LENGTH: 199
<212> TYPE: PRT
<213> ORGANISM: Artificial Sequence
<220> FEATURE:
<223> OTHER INFORMATION: Mutated two-domain ILT-2 polypeptide

<400> SEQUENCE: 18

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125
```

```
Asp Gly Phe Ile Leu Cys Lys Glu Gly Glu Asp Glu His Pro Gln Cys
        130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly Cys
            195
```

<210> SEQ ID NO 19
<211> LENGTH: 614
<212> TYPE: DNA
<213> ORGANISM: Artificial Sequence
<220> FEATURE:
<223> OTHER INFORMATION: DNA encoding a mutated two-domain ILT-2
      polypeptide with a terminal Cys codon and restriction enzyme
      recognition sites

<400> SEQUENCE: 19

```
tacgtaatgg gtcatcttcc aaaaccaact ctctgggctg aaccaggctc tgtgatcacc    60
atggatcagc ctgtgaccct caggtgtcag gggggccagg agacccagga gtaccgtcta   120
tatagagaaa agaaaacagc accctggatt acacggatcc acaggagct  tgtgaagaag   180
ggccagttcc ccatcccatc catcacctgg gaacatgcag ggcggtatcg ctgttactat   240
ggtagcgaca ctagtcaatg gtcggcgagc agtgaccccc tggagctggt ggtgacagga   300
gtctacatca aacccaccct ctcagcccag cccagccccg tggtgaactc aggagggaat   360
gtaaccctcc agtgtgactc acaggtggca tttgatggct tcattctgtg taaggaagga   420
gaagatgaac acccacaatg cctgaactcc agccccatg  cccgtgggtc gtcccgcgcc   480
atcttctccg tgggccccgt gagcccgagt cgcaggtggt ggtacaggtg ctatgcttat   540
gactcgaact ctccctatga gtggtctcta cccagtgatc tcctggagct cctggtccta   600
tgttaagcgg ccgc                                                      614
```

<210> SEQ ID NO 20
<211> LENGTH: 199
<212> TYPE: PRT
<213> ORGANISM: Artificial Sequence
<220> FEATURE:
<223> OTHER INFORMATION: Mutated two-domain ILT-2 polypeptide with a
      C-terminal Cys residue

<400> SEQUENCE: 20

```
Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ser Gln Trp Ser Ala Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110
```

```
Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
                180                 185                 190

Leu Glu Leu Leu Val Leu Cys
        195
```

<210> SEQ ID NO 21
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 21

```
Met Gly His Leu Pro Lys Pro Thr Leu Trp Ala Glu Pro Gly Ser Val
1               5                   10                  15

Ile Thr Leu Phe Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ala Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
                180                 185                 190

Leu Glu Leu Leu Val Leu
        195
```

<210> SEQ ID NO 22
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 22

```
Met Gly His Leu Pro Lys Pro Thr Leu Trp Ala Glu Pro Gly Ser Val
1               5                   10                  15
```

```
Ile Thr Leu Ser Gln Pro Val Thr Leu Arg Cys Gln Gly Gly Gln Glu
             20                  25                  30

Thr Gln Glu Tyr Arg Leu Tyr Arg Glu Lys Lys Thr Ala Pro Trp Ile
         35                  40                  45

Thr Arg Ile Pro Gln Glu Leu Val Lys Lys Gly Gln Phe Pro Ile Pro
     50                  55                  60

Ser Ile Thr Trp Glu His Ala Gly Arg Tyr Arg Cys Tyr Tyr Gly Ser
 65                  70                  75                  80

Asp Thr Ala Gly Arg Ser Glu Ser Ser Asp Pro Leu Glu Leu Val Val
                 85                  90                  95

Thr Gly Val Tyr Ile Lys Pro Thr Leu Ser Ala Gln Pro Ser Pro Val
                100                 105                 110

Val Asn Ser Gly Gly Asn Val Thr Leu Gln Cys Asp Ser Gln Val Ala
             115                 120                 125

Phe Asp Gly Phe Ile Leu Cys Lys Glu Gly Glu Asp Glu His Pro Gln
         130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 23
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 23

Met Gly His Leu Pro Lys Pro Thr Leu Gln Ala Glu Pro Gly Ser Val
 1               5                  10                  15

Ile Thr Gln Gly Ser Pro Val Thr Leu Arg Cys Gln Gly Gly Gln Glu
             20                  25                  30

Thr Gln Glu Tyr Arg Leu Tyr Arg Glu Lys Lys Thr Ala Pro Trp Ile
         35                  40                  45

Thr Arg Ile Pro Gln Glu Leu Val Lys Lys Gly Gln Phe Pro Ile Pro
     50                  55                  60

Ser Ile Thr Trp Glu His Ala Gly Arg Tyr Arg Cys Val Ile Gln Arg
 65                  70                  75                  80

Gly Thr Ala Gly Arg Ser Glu Ser Ser Asp Pro Leu Glu Leu Val Val
                 85                  90                  95

Thr Gly Val Tyr Ile Lys Pro Thr Leu Ser Ala Gln Pro Ser Pro Val
                100                 105                 110

Val Asn Ser Gly Gly Asn Val Thr Leu Gln Cys Asp Ser Gln Val Ala
             115                 120                 125

Phe Asp Gly Phe Ile Leu Cys Lys Glu Gly Glu Asp Glu His Pro Gln
         130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175
```

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 24
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 24

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Gln Gly Leu Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 25
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 25

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Thr
65                  70                  75                  80

```
Gln Thr Ala Gly Arg Ser Glu Ser Ser Asp Pro Leu Glu Leu Val Val
            85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 26
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 26

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
50                  55                  60

Ser Ile Thr Trp Glu His Ala Gly Arg Tyr Arg Cys Met Gln Tyr Thr
65                  70                  75                  80

Leu Thr Ala Gly Arg Ser Glu Ser Ser Asp Pro Leu Glu Leu Val Val
            85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 27
<211> LENGTH: 198
<212> TYPE: PRT
<213> ORGANISM: Artificial Sequence
<220> FEATURE:
<223> OTHER INFORMATION: Mutated two-domain ILT-2 polypeptide
```

<400> SEQUENCE: 27

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ser Gln Trp Ser Ala Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 28
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 28

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Gln Gly Gly Leu Arg Ser Glu Ser Ser Asp Pro Leu Glu Leu Val Val
                85                  90                  95

Thr Gly Ala Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe

```
                  145                 150                 155                 160
Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
                180                 185                 190

Leu Glu Leu Leu Val Leu
                195

<210> SEQ ID NO 29
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 29

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Thr
65                  70                  75                  80

Gln Thr Ala Gly Arg Ser Glu Ser Ser Asp Pro Leu Glu Leu Val Val
                85                  90                  95

Thr Gly Ala Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
                180                 185                 190

Leu Glu Leu Leu Val Leu
                195

<210> SEQ ID NO 30
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 30

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
```

```
                     50                  55                  60

Ser Ile Thr Trp Glu His Ala Gly Arg Tyr Arg Cys Met Gln Tyr Thr
 65                  70                  75                  80

Leu Thr Ala Gly Arg Ser Glu Ser Ser Asp Pro Leu Glu Leu Val Val
                 85                  90                  95

Thr Gly Ala Tyr Ile Lys Pro Thr Leu Ser Ala Gln Pro Ser Pro Val
             100                 105                 110

Val Asn Ser Gly Gly Asn Val Thr Leu Gln Cys Asp Ser Gln Val Ala
         115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 31
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 31

Met Gly His Leu Pro Lys Pro Thr Leu Trp Ala Glu Pro Gly Ser Val
 1               5                  10                  15

Ile Thr Met Asp Gln Pro Val Thr Leu Arg Cys Gln Gly Gly Gln Glu
                 20                  25                  30

Thr Gln Glu Tyr Arg Leu Tyr Arg Glu Lys Lys Thr Ala Pro Trp Ile
             35                  40                  45

Thr Arg Ile Pro Gln Glu Leu Val Lys Lys Gly Gln Phe Pro Ile Pro
         50                  55                  60

Ser Ile Thr Trp Glu His Ala Gly Arg Tyr Arg Cys Tyr Tyr Gly Ser
 65                  70                  75                  80

Gln Gly Gly Leu Arg Ser Glu Ser Ser Asp Pro Leu Glu Leu Val Val
                 85                  90                  95

Thr Gly Val Tyr Ile Lys Pro Thr Leu Ser Ala Gln Pro Ser Pro Val
             100                 105                 110

Val Asn Ser Gly Gly Asn Val Thr Leu Gln Cys Asp Ser Gln Val Ala
         115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 32
```

```
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 32

Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Thr
65                  70                  75                  80

Gln Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 33
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 33

Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Val Ile Gln Arg
65                  70                  75                  80

Gly Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125
```

-continued

```
Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 34
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 34

Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Met Gln Tyr Thr
65                  70                  75                  80

Leu Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 35
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 35

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30
```

```
Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Arg Gln Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195
```

<210> SEQ ID NO 36
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 36

```
Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Leu Ala Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190
```

```
Leu Glu Leu Leu Val Leu
        195

<210> SEQ ID NO 37
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 37

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Lys Ala Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 38
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 38

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95
```

```
Thr Gly Ile Tyr Gln Ala Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
            130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                    165                 170                 175

Ala Tyr Asp Ser Asn Ser Pro Tyr Glu Trp Ser Leu Pro Ser Asp Leu
                180                 185                 190

Leu Glu Leu Leu Val Leu
            195

<210> SEQ ID NO 39
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 39

Met Gly His Leu Pro Lys Pro Thr Leu Trp Ala Glu Pro Gly Ser Val
1               5                   10                  15

Ile Thr Gln Gly Ala Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
            130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                    165                 170                 175

Ala Tyr Asp Ser Asn Ser Pro Tyr Glu Trp Ser Leu Pro Ser Asp Leu
                180                 185                 190

Leu Glu Leu Leu Val Leu
            195

<210> SEQ ID NO 40
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 40
```

```
Met Gly His Leu Pro Lys Pro Thr Leu Trp Ala Glu Pro Gly Ser Val
1               5                   10                  15

Ile Thr Gln Gly Arg Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 41
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 41

Met Gly His Leu Pro Lys Pro Thr Leu Trp Ala Glu Pro Gly Ser Val
1               5                   10                  15

Ile Thr Val Gly Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
```

```
                        165                 170                 175
Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 42
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 42

Met Gly His Leu Pro Lys Pro Thr Leu Trp Ala Glu Pro Gly Ser Val
1               5                   10                  15

Ile Thr Leu Gly Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 43
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 43

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
```

```
                65                  70                  75                  80
Asp Thr Ala Gly Arg Ser Glu Ser Ser Asp Pro Leu Glu Leu Val Val
                    85                  90                  95

Thr Gly Val Tyr Ile Lys Pro Thr Leu Ser Ala Gln Pro Ser Pro Val
                100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
        130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 44
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 44

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Val Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                    85                  90                  95

Thr Gly Val Tyr Ile Lys Pro Thr Leu Ser Ala Gln Pro Ser Pro Val
                100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
        130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 45
<211> LENGTH: 198
<212> TYPE: PRT
<213> ORGANISM: Artificial Sequence
```

```
<220> FEATURE:
<223> OTHER INFORMATION: Mutated two-domain ILT-2 polypeptide

<400> SEQUENCE: 45

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Val Gly Trp Ala
65                  70                  75                  80

Val Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 46
<211> LENGTH: 198
<212> TYPE: PRT
<213> ORGANISM: Artificial Sequence
<220> FEATURE:
<223> OTHER INFORMATION: Mutated two-domain ILT-2 polypeptide
<220> FEATURE:
<221> NAME/KEY: misc_feature
<222> LOCATION: (170)..(170)
<223> OTHER INFORMATION: Xaa can be any naturally occurring amino acid

<400> SEQUENCE: 46

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Ile Gly Arg Ser
65                  70                  75                  80

Gln Thr Ala Gly Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
```

```
            115                 120                 125
Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Xaa Trp Trp Tyr Arg Cys Tyr
                165                 170                 175

Ala Tyr Asp Ser Asn Ser Pro Tyr Glu Trp Ser Leu Pro Ser Asp Leu
                180                 185                 190

Leu Glu Leu Leu Val Leu
        195

<210> SEQ ID NO 47
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 47

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Gly
65                  70                  75                  80

Gln Glu Gly Ala Arg Ser Glu Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
                180                 185                 190

Leu Glu Leu Leu Val Leu
        195

<210> SEQ ID NO 48
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 48

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
```

```
            20                  25                  30
Thr Gln Glu Tyr Arg Leu Tyr Arg Glu Lys Lys Thr Ala Pro Trp Ile
                35                  40                  45
Thr Arg Ile Pro Gln Glu Leu Val Lys Lys Gly Gln Phe Pro Ile Pro
             50                  55                  60
Ser Ile Thr Trp Glu His Ala Gly Arg Tyr Arg Cys Gln Gly Val Ser
 65                  70                  75                  80
Gln Thr Ala Gly Arg Ser Glu Ser Ser Asp Pro Leu Glu Leu Val Val
                 85                  90                  95
Thr Gly Val Tyr Ile Lys Pro Thr Leu Ser Ala Gln Pro Ser Pro Val
                100                 105                 110
Val Asn Ser Gly Gly Asn Val Thr Leu Gln Cys Asp Ser Gln Val Ala
                115                 120                 125
Phe Asp Gly Phe Ile Leu Cys Lys Glu Gly Glu Asp Glu His Pro Gln
                130                 135                 140
Cys Leu Asn Ser Gln Pro His Ala Arg Gly Ser Ser Arg Ala Ile Phe
145                 150                 155                 160
Ser Val Gly Pro Val Ser Pro Ser Arg Arg Trp Trp Tyr Arg Cys Tyr
                165                 170                 175
Ala Tyr Asp Ser Asn Ser Pro Tyr Glu Trp Ser Leu Pro Ser Asp Leu
                180                 185                 190
Leu Glu Leu Leu Val Leu
                195

<210> SEQ ID NO 49
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 49

Met Gly His Leu Pro Lys Pro Thr Leu Trp Ala Glu Pro Gly Ser Val
 1               5                  10                  15
Ile Thr Gln Gly Ser Pro Val Thr Leu Arg Cys Gln Gly Gly Gln Glu
                20                  25                  30
Thr Gln Glu Tyr Arg Leu Tyr Arg Glu Lys Lys Thr Ala Pro Gln Ile
                35                  40                  45
Thr Arg Ile Pro Gln Glu Leu Val Lys Lys Gly Gln Phe Pro Ile Pro
             50                  55                  60
Ser Ile Thr Trp Glu His Ala Gly Arg Tyr Arg Cys Tyr Tyr Gly Ser
 65                  70                  75                  80
Asp Thr Ala Gly Arg Ser Glu Ser Ser Asp Pro Leu Glu Leu Val Val
                 85                  90                  95
Thr Gly Val Tyr Val Ala Pro Thr Leu Ser Ala Gln Pro Ser Pro Val
                100                 105                 110
Val Asn Ser Gly Gly Asn Val Thr Leu Gln Cys Asp Ser Gln Val Ala
                115                 120                 125
Phe Asp Gly Phe Ile Leu Cys Lys Glu Gly Glu Asp Glu His Pro Gln
                130                 135                 140
Cys Leu Asn Ser Gln Pro His Ala Arg Gly Ser Ser Arg Ala Ile Phe
145                 150                 155                 160
Ser Val Gly Pro Val Ser Pro Gly Arg Arg Trp Trp Tyr Arg Cys Tyr
                165                 170                 175
Ala Tyr Asp Ser Asn Ser Pro Tyr Glu Trp Ser Leu Pro Ser Asp Leu
                180                 185                 190
```

```
Leu Glu Leu Leu Val Leu
        195

<210> SEQ ID NO 50
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 50

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Lys Ala Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 51
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 51

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95
```

```
Thr Gly Ile Tyr Gln Arg Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
        130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
            165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 52
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 52

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Gln Ala Pro Thr Leu Ser Ala Gln Pro Ser Pro Val
            100                 105                 110

Val Asn Ser Gly Gly Asn Val Thr Leu Gln Cys Asp Ser Gln Val Ala
            115                 120                 125

Phe Asp Gly Phe Ile Leu Cys Lys Glu Gly Glu Asp Glu His Pro Gln
        130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
            165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 53
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 53
```

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Leu Gln Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Gly Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 54
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 54

Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
                20                  25                  30

Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Lys Gln Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

```
Ser Val Gly Pro Val Ser Pro Gly Arg Arg Trp Trp Tyr Arg Cys Tyr
            165                 170                 175

Ala Tyr Asp Ser Asn Ser Pro Tyr Glu Trp Ser Leu Pro Ser Asp Leu
            180                 185                 190

Leu Glu Leu Leu Val Leu
            195
```

<210> SEQ ID NO 55
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 55

```
Met Gly His Leu Pro Lys Pro Thr Leu Trp Ala Glu Pro Gly Ser Val
1               5                   10                  15

Ile Thr Gln Gly Ser Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ala Gly Arg Ser Glu Ser Ser Asp Pro Leu Glu Leu Val Val
                85                  90                  95

Thr Gly Ile Tyr Gln Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195
```

<210> SEQ ID NO 56
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 56

```
Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60
```

```
Ser Ile Thr Trp Glu His Ala Gly Arg Tyr Arg Cys Tyr Tyr Gly Ser
 65                  70                  75                  80

Asp Thr Ala Gly Arg Ser Glu Ser Ser Asp Pro Leu Glu Leu Val Val
                 85                  90                  95

Thr Gly Ile Tyr Leu Ala Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 57
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 57

Met Gly His Leu Pro Lys Pro Thr Leu Trp Ala Glu Pro Gly Ser Val
  1               5                  10                  15

Ile Thr Leu Gly Gln Pro Val Thr Leu Arg Cys Gln Gly Gly Gln Glu
             20                  25                  30

Thr Gln Glu Tyr Arg Leu Tyr Arg Glu Lys Lys Thr Ala Pro Trp Ile
         35                  40                  45

Thr Arg Ile Pro Gln Glu Leu Val Lys Lys Gly Gln Phe Pro Ile Pro
 50                  55                  60

Ser Ile Thr Trp Glu His Ala Gly Arg Tyr Arg Cys Tyr Tyr Gly Ser
 65                  70                  75                  80

Asp Thr Ala Gly Arg Ser Glu Ser Ser Asp Pro Leu Glu Leu Val Val
                 85                  90                  95

Thr Gly Ile Tyr Leu Ala Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
            195

<210> SEQ ID NO 58
<211> LENGTH: 198
<212> TYPE: PRT
```

<213> ORGANISM: Artificial Sequence
<220> FEATURE:
<223> OTHER INFORMATION: Mutated two-domain ILT-2 polypeptide

<400> SEQUENCE: 58

```
Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ser Gln Trp Ser Ala Ser Ser Asp Pro Leu Glu Leu Val Val
                85                  90                  95

Thr Gly Ile Tyr Leu Ala Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195
```

<210> SEQ ID NO 59
<211> LENGTH: 198
<212> TYPE: PRT
<213> ORGANISM: Artificial Sequence
<220> FEATURE:
<223> OTHER INFORMATION: MGHLPKPTLWAEPGSVITMDQPVTLRCQGGQETQEYRLYREKKTAP
      WITRIPQELVKKGQFPIPSITWEHAGRYRCYYGSDTSQWSASSDPLELVVTGIYLAPTLSAQPSP
      VVNSGGNVTLQCDSQVAFDGFILCKEGEDEHPQCLNSQPHARGSSRAIFSVGPVSPSRRWWYRCY
      AYDSNSPYEWSLPSDLLELLVL

<400> SEQUENCE: 59

```
Met Gly His Leu Pro Lys Pro Thr Leu Trp Ala Glu Pro Gly Ser Val
1               5                   10                  15

Ile Thr Leu Gly Gln Pro Val Thr Leu Arg Cys Gln Gly Gly Gln Glu
            20                  25                  30

Thr Gln Glu Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Ser Gln Trp Ser Ala Ser Ser Asp Pro Leu Glu Leu Val Val
                85                  90                  95

Thr Gly Ile Tyr Leu Ala Pro Thr Leu Ser Ala Gln Pro Ser Pro Val
            100                 105                 110

Val Asn Ser Gly Gly Asn Val Thr Leu Gln Cys Asp Ser Gln Val Ala
```

```
                    115                 120                 125
Phe Asp Gly Phe Ile Leu Cys Lys Glu Gly Glu Asp Glu His Pro Gln
    130                 135                 140
Cys Leu Asn Ser Gln Pro His Ala Arg Gly Ser Ser Arg Ala Ile Phe
145                 150                 155                 160
Ser Val Gly Pro Val Ser Pro Ser Arg Arg Trp Trp Tyr Arg Cys Tyr
                    165                 170                 175
Ala Tyr Asp Ser Asn Ser Pro Tyr Glu Trp Ser Leu Pro Ser Asp Leu
                180                 185                 190
Leu Glu Leu Leu Val Leu
        195

<210> SEQ ID NO 60
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 60

Met Gly His Leu Pro Lys Pro Thr Leu Trp Ala Glu Pro Gly Ser Val
1               5                   10                  15
Ile Thr Met Asp Gln Pro Val Thr Leu Arg Cys Gln Gly Gly Gln Glu
                20                  25                  30
Thr Gln Glu Tyr Arg Leu Tyr Arg Glu Lys Lys Thr Ala Pro Trp Ile
            35                  40                  45
Thr Arg Ile Pro Gln Glu Leu Val Lys Lys Gly Gln Phe Pro Ile Pro
        50                  55                  60
Ser Ile Thr Trp Glu His Ala Gly Arg Tyr Arg Cys Ile Gly Arg Ser
65                  70                  75                  80
Gln Thr Ser Gln Trp Ser Ala Ser Ser Asp Pro Leu Glu Leu Val Val
                85                  90                  95
Thr Gly Ile Tyr Leu Ala Pro Thr Leu Ser Ala Gln Pro Ser Pro Val
            100                 105                 110
Val Asn Ser Gly Gly Asn Val Thr Leu Gln Cys Asp Ser Gln Val Ala
        115                 120                 125
Phe Asp Gly Phe Ile Leu Cys Lys Glu Gly Glu Asp Glu His Pro Gln
    130                 135                 140
Cys Leu Asn Ser Gln Pro His Ala Arg Gly Ser Ser Arg Ala Ile Phe
145                 150                 155                 160
Ser Val Gly Pro Val Ser Pro Ser Arg Arg Trp Trp Tyr Arg Cys Tyr
                    165                 170                 175
Ala Tyr Asp Ser Asn Ser Pro Tyr Glu Trp Ser Leu Pro Ser Asp Leu
                180                 185                 190
Leu Glu Leu Leu Val Leu
        195

<210> SEQ ID NO 61
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 61

Met Gly His Leu Pro Lys Pro Thr Leu Trp Ala Glu Pro Gly Ser Val
1               5                   10                  15
Ile Thr Leu Gly Gln Pro Val Thr Leu Arg Cys Gln Gly Gly Gln Glu
```

```
                        20                  25                  30
Thr Gln Glu Tyr Arg Leu Tyr Arg Glu Lys Lys Thr Ala Pro Trp Ile
            35                  40                  45

Thr Arg Ile Pro Gln Glu Leu Val Lys Lys Gly Gln Phe Pro Ile Pro
        50                  55                  60

Ser Ile Thr Trp Glu His Ala Gly Arg Tyr Arg Cys Ile Gly Arg Ser
65                  70                  75                  80

Gln Thr Ser Gln Trp Ser Ala Ser Asp Pro Leu Glu Leu Val Val
                85                  90                  95

Thr Gly Ile Tyr Leu Ala Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Trp Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Leu Val Leu
        195

<210> SEQ ID NO 62
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 62

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
            180                 185                 190
```

```
Glu Leu Asp Val Asp Gly
        195

<210> SEQ ID NO 63
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 63

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
                20                  25                  30

Gln Glu Tyr Arg Leu Tyr Arg Glu Lys Lys Thr Ala Pro Trp Ile Thr
            35                  40                  45

Arg Ile Pro Gln Glu Leu Val Lys Lys Gly Gln Phe Pro Ile Pro Ser
        50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Arg Tyr Arg Cys Tyr Ala
                165                 170                 175

Tyr Asp Ser Asn Ser Pro Tyr Glu Trp Ser Leu Pro Ser Asp Leu Leu
            180                 185                 190

Glu Leu Asp Val Asp Gly
        195

<210> SEQ ID NO 64
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 64

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
                20                  25                  30

Gln Glu Tyr Arg Leu Tyr Arg Glu Lys Lys Thr Ala Pro Trp Ile Thr
            35                  40                  45

Leu Ile Pro Gln Glu Leu Val Lys Lys Gly Gln Phe Pro Ile Pro Ser
        50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95
```

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Gly His Pro Gln Cys
    130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Trp Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
        195

<210> SEQ ID NO 65
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 65

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Arg Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
        195

<210> SEQ ID NO 66
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 66

```
Met His Leu Pro Lys Pro Thr Leu Trp Ala Glu Pro Gly Ser Val Ile
1               5                   10                  15

Thr Leu Gly Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
50                      55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
            180                 185                 190

Glu Leu Asp Val Asp Gly
            195

<210> SEQ ID NO 67
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 67

Met His Leu Pro Lys Pro Thr Leu Trp Ala Glu Pro Gly Ser Val Ile
1               5                   10                  15

Thr Leu Gly Ser Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
50                      55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
130                 135                 140

Leu Asn Ser Gln Pro His Ala Arg Gly Ser Ser Arg Ala Ile Phe Ser
145                 150                 155                 160
```

-continued

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
            180                 185                 190

Glu Leu Asp Val Asp Gly
        195

<210> SEQ ID NO 68
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 68

Met His Leu Pro Lys Pro Thr Leu Trp Ala Glu Pro Gly Ser Val Ile
1               5                   10                  15

Thr Leu Arg Ser Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
            180                 185                 190

Glu Leu Asp Val Asp Gly
        195

<210> SEQ ID NO 69
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 69

Met His Leu Pro Lys Pro Thr Leu Trp Ala Glu Pro Gly Ser Val Ile
1               5                   10                  15

Thr Leu Gln Ser Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

```
Ile Thr Trp Glu His Ala Gly Arg Tyr Arg Cys Tyr Tyr Gly Ser Asp
 65                  70                  75                  80

Thr Ser Gln Trp Ser Ala Ser Asp Pro Leu Glu Leu Val Val Thr
             85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
            115                 120                 125

Asp Gly Phe Ile Leu Cys Lys Glu Gly Glu Asp Glu His Pro Gln Cys
            130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
            165                 170                 175

Tyr Asp Ser Asn Ser Pro Tyr Glu Trp Ser Leu Pro Ser Asp Leu Leu
            180                 185                 190

Glu Leu Asp Val Asp Gly
            195

<210> SEQ ID NO 70
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 70

Met His Leu Pro Lys Pro Thr Leu Trp Ala Glu Pro Gly Ser Val Ile
  1               5                  10                  15

Thr Leu Glu Ser Pro Val Thr Leu Arg Cys Gln Gly Gly Gln Glu Thr
             20                  25                  30

Gln Glu Tyr Arg Leu Tyr Arg Glu Lys Lys Thr Ala Pro Trp Ile Thr
             35                  40                  45

Arg Ile Pro Gln Glu Leu Val Lys Lys Gly Gln Phe Pro Ile Pro Ser
 50                  55                  60

Ile Thr Trp Glu His Ala Gly Arg Tyr Arg Cys Tyr Tyr Gly Ser Asp
 65                  70                  75                  80

Thr Ser Gln Trp Ser Ala Ser Asp Pro Leu Glu Leu Val Val Thr
             85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
            115                 120                 125

Asp Gly Phe Ile Leu Cys Lys Glu Gly Glu Asp Glu His Pro Gln Cys
            130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
            165                 170                 175

Tyr Asp Ser Asn Ser Pro Tyr Glu Trp Ser Leu Pro Ser Asp Leu Leu
            180                 185                 190

Glu Leu Asp Val Asp Gly
            195

<210> SEQ ID NO 71
<211> LENGTH: 198
<212> TYPE: PRT
```

<213> ORGANISM: Artificial Sequence
<220> FEATURE:
<223> OTHER INFORMATION: Mutated two-domain ILT-2 polypeptide

<400> SEQUENCE: 71

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Thr Gln
65                  70                  75                  80

Thr Ala Gly Arg Ser Glu Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
    130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
            180                 185                 190

Glu Leu Asp Val Asp Gly
        195

<210> SEQ ID NO 72
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 72

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Met Gln Tyr Thr Leu
65                  70                  75                  80

Thr Ala Gly Arg Ser Glu Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys

```
                130                 135                 140
Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
                195

<210> SEQ ID NO 73
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 73

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
                20                  25                  30

Gln Glu Tyr Arg Leu Tyr Arg Glu Lys Lys Thr Ala Pro Trp Ile Thr
            35                  40                  45

Arg Ile Pro Gln Glu Leu Val Lys Lys Gly Gln Phe Pro Ile Pro Ser
        50                  55                  60

Ile Thr Trp Glu His Ala Gly Arg Tyr Arg Cys Val Ile Gln Arg Gly
65                  70                  75                  80

Thr Ala Gly Arg Ser Glu Ser Ser Asp Pro Leu Glu Leu Val Val Thr
                85                  90                  95

Gly Val Tyr Ile Lys Pro Thr Leu Ser Ala Gln Pro Ser Pro Val Val
                100                 105                 110

Asn Ser Gly Gly Asn Val Thr Leu Gln Cys Asp Ser Gln Val Ala Phe
            115                 120                 125

Asp Gly Phe Ile Leu Cys Lys Glu Gly Glu Asp Glu His Pro Gln Cys
        130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
                195

<210> SEQ ID NO 74
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 74

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
                20                  25                  30

Gln Glu Tyr Arg Leu Tyr Arg Glu Lys Lys Thr Ala Pro Trp Ile Thr
```

```
                    35                  40                  45
Arg Ile Pro Gln Glu Leu Val Lys Lys Gly Gln Phe Pro Ile Pro Ser
 50                  55                  60

Ile Thr Trp Glu His Ala Gly Arg Tyr Arg Cys Tyr Tyr Gly Gly Gln
 65                  70                  75                  80

Glu Gly Ala Arg Ser Glu Ser Asp Pro Leu Glu Leu Val Val Thr
                 85                  90                  95

Gly Val Tyr Ile Lys Pro Thr Leu Ser Ala Gln Pro Ser Pro Val Val
                100                 105                 110

Asn Ser Gly Gly Asn Val Thr Leu Gln Cys Asp Ser Gln Val Ala Phe
                115                 120                 125

Asp Gly Phe Ile Leu Cys Lys Glu Gly Glu Asp Glu His Pro Gln Cys
                130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
        195
```

<210> SEQ ID NO 75
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 75

```
Met His Leu Pro Lys Pro Thr Leu Trp Ala Glu Pro Gly Ser Val Ile
 1               5                  10                  15

Thr Met Asp Gln Pro Val Thr Leu Arg Cys Gln Gly Gly Gln Glu Thr
                 20                  25                  30

Gln Glu Tyr Arg Leu Tyr Arg Glu Lys Lys Thr Ala Pro Trp Ile Thr
             35                  40                  45

Arg Ile Pro Gln Glu Leu Val Lys Lys Gly Gln Phe Pro Ile Pro Ser
 50                  55                  60

Ile Thr Trp Glu His Ala Gly Arg Tyr Arg Cys Tyr Tyr Gly Thr Gln
 65                  70                  75                  80

Thr Ser Gln Trp Ser Ala Ser Ser Asp Pro Leu Glu Leu Val Val Thr
                 85                  90                  95

Gly Val Tyr Ile Lys Pro Thr Leu Ser Ala Gln Pro Ser Pro Val Val
                100                 105                 110

Asn Ser Gly Gly Asn Val Thr Leu Gln Cys Asp Ser Gln Val Ala Phe
                115                 120                 125

Asp Gly Phe Ile Leu Cys Lys Glu Gly Glu Asp Glu His Pro Gln Cys
                130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
        195
```

-continued

<210> SEQ ID NO 76
<211> LENGTH: 199
<212> TYPE: PRT
<213> ORGANISM: Artificial Sequence
<220> FEATURE:
<223> OTHER INFORMATION: Mutated two-domain ILT-2 polypeptide

<400> SEQUENCE: 76

```
Met Gly His Leu Pro Lys Pro Thr Leu Trp Ala Glu Pro Gly Ser Val
1               5                   10                  15

Ile Thr Met Asp Gln Pro Val Thr Leu Arg Cys Gln Gly Gly Gln Glu
            20                  25                  30

Thr Gln Gln Tyr Arg Leu Tyr Arg Glu Lys Lys Thr Ala Pro Trp Ile
        35                  40                  45

Thr Arg Ile Pro Gln Glu Leu Val Lys Lys Gly Gln Phe Pro Ile Pro
    50                  55                  60

Ser Ile Thr Trp Glu His Ala Gly Arg Tyr Arg Cys Tyr Tyr Gly Ser
65                  70                  75                  80

Asp Thr Arg Gln Trp Ser Ala Ser Ser Asp Pro Leu Glu Leu Val Val
                85                  90                  95

Thr Gly Val Tyr Ile Lys Pro Thr Leu Ser Ala Gln Pro Ser Pro Val
            100                 105                 110

Val Asn Ser Gly Gly Asn Val Thr Leu Gln Cys Asp Ser Gln Val Ala
        115                 120                 125

Phe Asp Gly Phe Ile Leu Cys Lys Glu Gly Glu Asp Glu His Pro Gln
    130                 135                 140

Cys Leu Asn Ser Gln Pro His Ala Arg Gly Ser Ser Arg Ala Ile Phe
145                 150                 155                 160

Ser Val Gly Pro Val Ser Pro Ser Arg Arg Trp Arg Tyr Arg Cys Tyr
                165                 170                 175

Ala Tyr Asp Ser Asn Ser Pro Tyr Glu Trp Ser Leu Pro Ser Asp Leu
            180                 185                 190

Leu Glu Leu Asp Val Asp Gly
        195
```

<210> SEQ ID NO 77
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 77

```
Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110
```

Asn Ser Gly Gly Asn Val Thr Leu Gln Cys Asp Ser Gln Val Ala Phe
            115                 120                 125

Asp Gly Phe Ile Leu Cys Lys Glu Gly Glu Asp Glu His Pro Gln Cys
        130                 135                 140

Asp Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
        195

<210> SEQ ID NO 78
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 78

Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
    50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
            115                 120                 125

Asp Gly Phe Ile Leu Cys Lys Glu Gly Glu Asp Glu His Pro Gln Cys
        130                 135                 140

Leu Asn Ser Gln Pro His Ala Arg Gly Ser Ser Arg Ala Glu Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
                180                 185                 190

Glu Leu Asp Val Asp Gly
        195

<210> SEQ ID NO 79
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 79

```
Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Cys Lys Glu Gly Glu Asp Glu His Pro Gln Cys
130                 135                 140

Leu Asn Ser Gln Pro His Ala Arg Gly Ser Ser Arg Ala Ile Phe Ser
145                 150                 155                 160

Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Pro Ser Asp Leu Leu
            180                 185                 190

Glu Leu Asp Val Asp Gly
            195
```

<210> SEQ ID NO 80
<211> LENGTH: 198
<212> TYPE: PRT
<213> ORGANISM: Artificial Sequence
<220> FEATURE:
<223> OTHER INFORMATION: Mutated two-domain ILT-2 polypeptide

<400> SEQUENCE: 80

```
Met His Leu Pro Lys Pro Thr Leu Trp Ala Glu Pro Gly Ser Val Ile
1               5                   10                  15

Thr Met Asp Gln Pro Val Thr Leu Arg Cys Gln Gly Gly Gln Glu Thr
            20                  25                  30

Gln Glu Tyr Arg Leu Tyr Arg Glu Lys Lys Thr Ala Pro Trp Ile Thr
        35                  40                  45

Arg Ile Pro Gln Glu Leu Val Lys Lys Gly Gln Phe Pro Ile Pro Ser
50                  55                  60

Ile Thr Trp Glu His Ala Gly Arg Tyr Arg Cys Tyr Tyr Gly Ser Asp
65                  70                  75                  80

Thr Ser Gln Trp Ser Ala Ser Ser Asp Pro Leu Glu Leu Val Val Thr
                85                  90                  95

Gly Val Tyr Ile Lys Pro Thr Leu Ser Ala Gln Pro Ser Pro Val Val
            100                 105                 110

Asn Ser Gly Gly Asn Val Thr Leu Gln Cys Asp Ser Gln Val Ala Phe
        115                 120                 125

Asp Gly Phe Ile Leu Ser Lys Glu Gly Glu Asp Glu His Pro Gln Ser
130                 135                 140

Leu Asn Ser Gln Pro His Ala Arg Gly Ser Ser Arg Ala Ile Phe Ser
145                 150                 155                 160
```

-continued

```
Val Gly Pro Val Ser Pro Ser Arg Arg Trp Trp Tyr Arg Cys Tyr Ala
                165                 170                 175

Tyr Asp Ser Asn Ser Pro Tyr Glu Trp Ser Leu Pro Ser Asp Leu Leu
            180                 185                 190

Glu Leu Asp Val Asp Gly
        195
```

The invention claimed is:

1. A polypeptide which has an amino acid sequence at least 90% identical to SEQ ID NO:7, wherein said polypeptide comprises a mutation at one or more amino acid positions corresponding to amino acids 19Q, 20G, 21S, 47W, 50R, 661, 78Y, 80S, 82T, 87E, 99A, 102K, 141E, 146L, 147N, and 174R of SEQ ID NO: 3, whereby the polypeptide binds to a class I pMHC with a $K_D$ of less than or equal to 1 μM or slower and inhibits CD8 binding to the pMHC to a greater extent than the polypeptide SEQ ID NO:3.

2. A polypeptide as claimed in claim 1 comprising one or more of the following mutations 10W→L, 19Q→M, 19Q→L, 19Q→V, 20G→D, 20G→M, 20G→Q, 20G→F, 20G→S, 20G→E, 20G→R, 21S→Q, 21S→R, 21S→A, 42K→R, 47W→Q, 50R→L, 66I→V, =77Y→V, 77Y→M, 78Y→Q, 78Y→I, 78Y→G, 79G→Q, 79G→W, 79G→R, 79G→V, 80S→R, 80S→T, 80S→G, 81D→G, 81D→Q, 81D→L, 81D→V, 82T→G, 82T→E, 83A→S, 83A→G, 83A→R, 84G→L, 84G→Q, 84G→A, 87E→A, 99A→I, 99A→V, 101I→L, 101I→K, 101I→Q, 101I→V 102K→Q, 102K→A, 102K→R, 141E→G, 141E→D, 146L→D, 147N→S, 159I→E, 168S→G, 172W→R, 174R→W or 188L→D using the numbering of SEQ ID NO:3.

3. A polypeptide as claimed in claim 1 comprising mutations corresponding to 19Q→M and 21S→Q using the numbering of SEQ ID NO:3.

4. A polypeptide as claimed in claim 1 which comprises any of SEQ ID NOS:6 to 9 or 21 to 61.

5. A polypeptide as claimed in claim 1 wherein amino acids corresponding to 196L and/or 198L of NO:3 are mutated to 196D and 198D respectively.

6. A polypeptide as claimed in claim 1 which comprises any of SEQ ID NOS:63 to 80.

7. A polypeptide as claimed in claim 1 which comprises a tag on the C-terminal thereof, wherein said tag is a cysteine residue.

8. A polypeptide as claimed in claim 1 associated with a therapeutic agent.

9. A polypeptide as claimed in claim 8 wherein the therapeutic agent is IL-4, IL-10 or IL-13.

10. A polypeptide as claimed in claim 1 which is soluble.

11. An isolated cell or a particle presenting at least one polypeptide as defined in claim 1.

12. A pharmaceutical composition comprising:

a polypeptide as claimed in claim 1; or a plurality of cells or particles presenting at least one polypeptide as defined in claim 1, together with a pharmaceutically acceptable carrier.

13. A pharmaceutical composition according to claim 12 in a form suitable for parenteral administration, wherein the polypeptide is soluble.

14. A method of producing a polypeptide as claimed in claim 1, comprising:

(i) transforming a host cell with a vector incorporating a nucleic acid encoding a polypeptide as claimed in claim 1; and (ii) culturing the transformed cells under conditions suitable for the expression of the polypeptide; and (iii) recovering the expressed polypeptide.

15. A polypeptide as claimed in claim 1, further comprising a detectable label.

16. A polypeptide as claimed in claim 1 comprising one or more of the following mutations: 19Q→M, 20G→D, 21S→Q, 83A→R, 84G→Q, 87E→A, 99A→N, 141E→D, or 172W→R using the numbering of SEQ ID NO:3.

* * * * *